US009403866B2

(12) United States Patent
Harley et al.

(10) Patent No.: US 9,403,866 B2
(45) Date of Patent: *Aug. 2, 2016

(54) COMPOSITIONS AND METHODS FOR INCREASING TELOMERASE ACTIVITY

(71) Applicant: Telomerase Activation Sciences, Inc., New York, NY (US)

(72) Inventors: Calvin Bruce Harley, Murphys, CA (US); Soo-Peang Khor, Saratoga, CA (US); Mahesh Ramaseshan, Sunnyvale, CA (US); Premchandran H. Ramiya, San Ramon, CA (US); Zhu Z. Pirot, Redwood City, CA (US); Steven Fauce, Mountain View, CA (US); Tong Lin, Palo Alto, CA (US)

(73) Assignee: TELOMERASE ACTIVATION SCIENCES, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/936,823

(22) Filed: Jul. 8, 2013

(65) Prior Publication Data

US 2014/0088055 A1    Mar. 27, 2014

Related U.S. Application Data

(63) Continuation of application No. 12/781,515, filed on May 17, 2010, now Pat. No. 8,481,721.

(60) Provisional application No. 61/179,305, filed on May 18, 2009.

(51) Int. Cl.
*A61K 31/56* (2006.01)
*C07J 53/00* (2006.01)
*C07J 17/00* (2006.01)

(52) U.S. Cl.
CPC ............ *C07J 17/00* (2013.01); *A61K 31/56* (2013.01); *C07J 53/004* (2013.01)

(58) Field of Classification Search
None
See application file for complete search history.

(56) References Cited

U.S. PATENT DOCUMENTS

| 4,738,957 | A | 4/1988 | Laurent et al. |
|---|---|---|---|
| 5,629,154 | A | 5/1997 | Kim et al. |
| 5,663,160 | A | 9/1997 | Meybeck et al. |
| 5,770,578 | A | 6/1998 | Binder et al. |
| 5,785,977 | A | 7/1998 | Breithbarth |
| 5,786,343 | A | 7/1998 | Ber |
| 5,891,639 | A | 4/1999 | Harley et al. |
| 5,916,565 | A | 6/1999 | Rose et al. |
| 5,942,233 | A | 8/1999 | Chang |
| 6,007,989 | A | 12/1999 | West et al. |
| 6,126,942 | A | 10/2000 | Yang |
| 6,153,208 | A | 11/2000 | McAtee et al. |
| 6,162,459 | A | 12/2000 | Hu |
| 6,171,604 | B1 | 1/2001 | Mousa |
| 6,190,678 | B1 | 2/2001 | Hasenoehrl et al. |
| 6,277,396 | B1 | 8/2001 | Dente |
| 6,346,539 | B1 | 2/2002 | Raman et al. |
| 6,689,767 | B2 | 2/2004 | Krasutsky et al. |
| 6,696,094 | B2 | 2/2004 | Wu |
| 6,855,344 | B2 | 2/2005 | Chou |
| 7,846,904 | B2 | 12/2010 | Harley et al. |
| 8,481,721 | B2 * | 7/2013 | Harley et al. ............... 540/94 |
| 2002/0013260 | A1 | 1/2002 | Jia |
| 2002/0044977 | A1 | 4/2002 | Close |
| 2002/0164387 | A1 | 11/2002 | Wei et al. |
| 2002/0182272 | A1 | 12/2002 | Halstead |
| 2003/0108629 | A1 | 6/2003 | Chou |
| 2004/0241192 | A1 | 12/2004 | Valiante |
| 2005/0014730 | A1 | 1/2005 | Carlson et al. |
| 2007/0154435 | A1 | 7/2007 | Harley |
| 2008/0113925 | A1 * | 5/2008 | Harley et al. ............... 514/26 |

FOREIGN PATENT DOCUMENTS

| CN | 1283462 | 2/2001 |
|---|---|---|
| CN | 1079265 | 2/2002 |
| CN | 1383853 | 12/2002 |
| CN | 1406585 | 4/2003 |
| CN | 1793132 | 6/2006 |
| EP | 1403252 | 3/2004 |
| GB | 1392902 | 5/1975 |
| JP | 62-12791 | 1/1987 |
| JP | 8-503931 | 4/1996 |
| JP | 8-510474 | 11/1996 |
| JP | 10-36388 | 2/1998 |

(Continued)

OTHER PUBLICATIONS

"Amino Acid Ester Prodrugs of Floxuridine: Synthesis and Effects of Structure, Stereochemistry, and Site of Esterification on the Rate of Hydrolysis" by Vig et al., Pharma. Res. 20, 1381-88 (2003).*
"Salt Selection and Optimization Procedures for Pharmaceutical New Chemical Entities" by Bastin et al., Org. Proc. Res. Dev. 4, 427-35 (2000).*
"Astragalus", www.drugs.com/npp/astragalus.html, (Oct. 20, 2008), 7 pages.
Abdallah, R., et al., "Astragalosides from Egyptian asragalus spinosus vahl", Die Pharmazie, vol. 48(6), pp. 452-454 (1993).
Alder, J. et al., "Short telomeres are a Risk factor for idiopathic pulmonary fibrosis", Proc. Natl. Acad. Sci. USA, vol. 105(35), pp. 13051-13056 (2008).
Bastin et al., "Salt Selection and Optimization Procedures for Pharmaceutical New Chemical Entities," Org. Proc. Res. Dev., vol. 4, pp. 427-435 (2000).
Bedir, E. et al, "Immunostimulatory effects of cycloartane-type triterpene glycosides from *Astragalus* species", Biol. Pharm. Bull., vol. 23(7), pp. 834-837 (2000).

(Continued)

*Primary Examiner* — Theodore R West
(74) *Attorney, Agent, or Firm* — Wilmer Cutler Pickering Hale and Dorr LLP

(57) ABSTRACT

The present invention relates to methods and compositions for increasing telomerase activity in cells. Such compositions include pharmaceutical formulations. The methods and compositions are useful for treating diseases subject to treatment by an increase in telomerase activity in cells or tissue of a patient. They are also useful for enhancing replicative capacity of cells in culture, as in ex vivo cell therapy and for enhancing proliferation of stem and progenitor cells.

13 Claims, 2 Drawing Sheets

(56) References Cited

FOREIGN PATENT DOCUMENTS

| JP | 2000-204091 | 7/2000 |
|---|---|---|
| JP | 2000-229827 | 8/2000 |
| JP | 2000-229834 | 8/2000 |
| JP | 2003-089687 | 3/2003 |
| JP | 2003-160497 | 6/2003 |
| WO | WO-99/35243 | 7/1999 |
| WO | WO-00/08135 | 2/2000 |
| WO | WO-00/31238 | 6/2000 |
| WO | WO-01/01996 | 1/2001 |
| WO | WO-02/07732 | 1/2002 |
| WO | WO-02/26761 | 4/2002 |
| WO | WO-02/091999 | 11/2002 |
| WO | WO-2004/112724 | 12/2004 |
| WO | WO-2005/000245 | 1/2005 |
| WO | WO-2005/044179 | 5/2005 |
| WO | WO-2008/149353 | 12/2008 |

OTHER PUBLICATIONS

Bedir, E. et al., "Cyoloartane triterpene glycosides from the roots of Astragalus brachypterus and Astragalus microcephalus", J. Nat. Prod., vol. 61, pp. 1469-1472 (1998).
Bender, D. et al., "Cyclopropanecarboxylic acid esters as potential prodrugs with enhanced hydrolytic stability", Organic Lett., vol. 19(3), pp. 509-511 (2008).
Beutner, K. et al., "Valacyclovir: a review of its antiviral activity, pharmacokinetic properties, and clinical efficacy", Antiviral Res., vol. 28, pp. 281-290 (1995).
Blackburn, E. "Telomerases", Annu. Rev. Biochem, vol. 61, pp. 113-129 (1992).
Bodnar, A. et al., "Extension of life-span by introduction of telomerase into normal human cells", Science, vol. 279, pp. 349-352 (1998).
Calzada, L. et al., "Effect of tetracyclic triterpenes (argentatins A, B and D) on the estradiol receptor of hormone-dependent tumors of human breast", Med. Sci. Res., vol. 23(12), pp. 815-816 (1995).
Chen, J. et al., "Huang Qi (Radix Astragali)", Chinese Medical Herbology and Pharmacology, Ch. 17 Tonic Herbs, Art of Medicine Press, pp. 847-852 (2004).
Chiu, C. et al., "Replicative senescence and cell immortality: the role of telomeres and telomerase", Proc. Sco. Exp. Biol. Med., vol. 214, pp. 99-106 (1997).
Choi, S. "Epidermis proliferative effect of the Panax ginseng ginsenoside Rb2", Arch. Pharm. Res., vol. 25(1), pp. 71-76 (2002).
Chu, D-T. et al., "Fractionated extract of Astragalus membranaceus, a Chinese medicinal herb, potentiates lak cell cytotoxicity generated by a low dose of recombinant interleukein-2", J. Clin. Lab. Immunol., vol. 26, pp. 183-187 (1988).
Chu, D-T. et al., "Immunotherapy with Chinese medicinal herbs. II Reversal of cyclophosphamide-induced immune suppression by administration of fractionated Astragalus membranaceus in vivo", J. Clin. Lab. Immunol., vol. 25, pp. 125-129 (1998).
Colla, L. et al., "Synthesis and antiviral activity of water-soluble esters of acyclovir [9-[(2-hydroxyethoxy)methyl]guanine]", J. Med. Chem., vol. 26, pp. 602-604 (1983).
Dagarag, M. et al., "Differential impairment of lytic and cytokine functions in senescent human immunodeficienty virus type 1 specific T lymphocytes", J. Virology, vol. 77(5), pp. 3077-3083 (2003).
Das, U. "Essential fatty acids and their metabolites could function as endogenous HMG-CoA reductase and ACE enzyme inhibitos, anti-arrhythmic, anti-hypertensive, anti-atherosclerotic, anti-inflammatory, cytoprotective, and cardioprotective molecules", Lipids in Health and Disease, vol. 7, (2008), 18 pages.
Farwell, D. et al., "Genetic and epigenetic changes in human epithelial cells immortalized by telomerase", Am. J. Pathol., vol. 156, pp. 1537-1547 (2000).
Fauce, S. et al., "Telomerase-based pharmacologic enhancement of antiviral function of human CD8+T lymphocytes", J. Immunol., vol. 181, pp. 7400-7406 (2008).

Franzese, O. et al., "Effect of saquinavir on proliferation and telomerase activity of human peripheral blood mononuclear cells", Life Sci., vol. 69(13), pp. 1509-1520 (2001).
Fujimoto, R, et al., "Expression of telomerase components in oral keratinocytes and squamous cell carcinomas", Oral. Oncol., vol. 37, pp. 132-140 (2001).
Funk, W. et al,, "Telomerase expression restores dermal integrity to in vitro-aged fibroblasts in a reconstituted skin model", Exp. Cell Res., vol. 258, pp. 270-280 (2000).
Greene, "Protection for the Amino Group," Chapter 7, Protecting Groups in Organic Synthesis, Third Edition, Wiley New York, 1999, 172 pages.
Harle-Bachor, C. et al "Telomerase activity in the regenerative basal layer of the epidermis in human skin and in immortal and carcinoma-derived skin keratinocytes", Proc. Natl. Acad. Sci. USA, vol. 93, pp. 6476-6481 (1996).
Harley, C. et al., "Telomeres shorten during ageing of human fibroblasts", Nature, vol. 345, pp. 458-460 (1990).
Hasegawa, H. et al., "Inhibitory effect of some trierpenoid saponins on glucose transport in tumor cells and its application to in vitro cytotoxic and antiviral activities", Planta Medica, vol. 60(3), pp. 240-243 (1994).
Henderson, S. et al., "In situ analysis of changes in telomere size during replicative aging and cell transformation", J. Cell Biol., vol. 134(1), pp. 1-12 (1996).
Huang, Y. et al., "Selected non-timber forest products with medicinal applications from Jilin province in China", Forest Communities in the Third Millenium: Linking Research, Business, and Policy Toward a Sustainable Non-Timber Forest Product Sector, Kenora, Ontario, Canada, Oct. 1-4, 1999, General Technical Report—North Central Research Station, USDA Forest Service, pp. 93-101 (2000).
Ionkova, I. "Astragalus species (Milk Vetch): in Vitro culture and the production of saponins, astragaline, and other biologically active compounds", Biotechnology in Agriculture and Forestry, vol. 33, Medicinal and Aromatic Plants VIII, Y. Bajaj, Ed., Spring Verlag, Berlin, pp. 97-138 (1995).
Ionkova, I. et al., "Cycloartane saponin production in hairy root cultures of Astralagus mongholicus", Phytochemistry, vol. 45(8), pp. 1597-1600 (1997).
Kaneko, M. et al., "Accelerated Recovery from cyclophosphamide-induced leukopenia in mice administered a Japanese ethical herbal drug, Hochu-ekki-to", Immunopharmacol., vol. 44(3), pp. 223-231 (1999).
Kang, M. et al., "Replicative senescence of normal human oral keratinocytes is associated with the loss of telomerase activity without shortening of telomeres", Cell Growth Diff., vol. 9, pp. 85-95 (1998).
Khushbaktova, Z. et al., "influence of cycloartanes from plants of the genus Astralagus and their synthetic analogs on the contractive function of the myocarbium and the activity of Na, K-ATPase", Chem. Natural Compounds, vol. 30(4), pp. 469-473 (1994).
Kinjo, J. et al., "Anti-herpes virus activity of fabaceous triterpenoidal saponins", Biol. Pharm. Bull., vol. 23(7), pp. 887-889 (2000).
Kitagawa, I. et al., "Saponin and sapogenol XXXIV. Chemical constituents of astragil radix, the root of astralagus membranaceus bunge (1) Cycloastragenol, the 9,19-cyclolanostane-type aglycone of astragalosides, and the artifact aglycone astragenol", Chem. Pharm. Bull., vol. 31(2), pp. 689-697 (1983).
Kitagawa, I. et al., "Saponin and Sapogenol XXXV. Chemical constituents of Astragali radix, the root of astragalus membranaceus bunge (2). Astragalosides I, II and IV. Acetylastragaloside I and isoastragalosides I and II", Chem. Pharm. Bull., vol. 31(2), pp. 698-708 (1983).
Kitagawa, I. et al., "Saponin and sapogenol. XXXVI. Chemical constituents of Astragali radix, the root of Astragalus membranaceous BUNGE. Astragalosides III, V, and VI", Chem. Pharm. Bull., vol. 31(2), pp. 709-715 (1983).
Lee, K et al., "Immortalization with telomerase of the Nestin-positive cells of the human pancreas", Biochem. Biophys. Res. Commun., vol. 301(4), (2003),pp. 1038-1044.
Li, C-X. et al., "Effects of Buyang Huanwu decoction and its active constituents on teh fluidity of brain cell membrane in vitro", Chinese Pharmaceutical Journal, vol. 36(8), pp. 528-531 (2001).

(56) References Cited

OTHER PUBLICATIONS

Li, J. et al., "Effect of retinoic acid and genseng on the telomerase activity in the liver cancer cell", J. Tropical Med., vol. 2(1), pp. 39-40 (2002).

Li, Z.-P. et al., "Effects of astragaloside IV on myocardial calcium transport and cardiac function in ischemic rats", Acta Pharmacol. Sinica, vol. 23(10), pp. 898-904 (2002).

Luo, H. et al., "Nuclear cardiology study on effective ingredients of Astralagus membranaceus in treating heart failure", Chin. J. Integrated Traditional and Western Med., vol. 15(12), pp. 707-709 (1995).

Mattson, M. "Emerging neuroprotective strategies for Alzheimer's disease: dietary restriction, telomerase activation, and stem cell therapy", Exp. Gerontol., vol. 35(4), pp. 489-502 (2000).

Morales, C. et al., "Absence of cancer-associated changes in human fibroblasts after immortalization with telomerase", Nature Genet., vol. 21(1), pp. 115-118 (1999).

Oda, K. et al., "Adjuvant and haemolytic activities of 47 saponins derived from medicinal and food plants", Biol. Chem., vol. 381(1), pp. 67-74 (2000).

Oh, H. "the emerging role of telomerase in cardiac muscle growth and survival", J. Mol. Cell. Cardiol., vol. 34(7), pp. 717-724 (2002).

Pan, F. et al., "Studies on triterpenoids of Astragalus floridus", Acta Botanica Sinica, vol. 38, pp. 836-838 (1996).

Papadopoulos, G. et al., "Antioxidant effect of natural phenols on olive oil", JAOCS, vol. 68(9), pp. 669-671 (1991).

Parra-Delgado, H. et al,. "Synthesis of argentatin A derivatives as growth inhibitors of human cancer cell lines in vitro", Bioorganic & Med. Chem. Lett., vol. 15, pp. 1005-1008 (2005).

Pistelli, L. et al., "Antimicrobial and antifungal activity of crude extracts and isolated saponins from Astralagus verrucosus", Fitoterapia, vol. 73(4), pp. 336-339 (2002).

Polat, E. et al., "Cycloartane-type glycosides from Astralagus ambiolepis", Phytochemistry, vol. 70, pp. 6208-6634 (2009).

Remington, "The Science and Practice of Pharmacy," vol. 1, Mack Publishing Company, Easton, Pennsylvania, 1995, ISBN 0-912734-04-3, 433 pages.

Remington: The Science and Practice of Pharmacy, vol. II, 19th Edition, 1995, Mack Publishing Company, Easton, Pennsylvania, ISBN 0-912734-04-3, 581 pages.

Simonsen, J. et al., "Telomerase expression extends the proliferative life-span and maintains the osteogenic potential of human bone marrow stromal cells", Nature Biotech., vol. 20(6), pp. 592-596 (2002).

Song, X. et al., "Amino acid ester prodrugs of the antiviral agent 2-Bromo-5,6-dichloro-1-(B-D-ribofuranosyl)benzimidazole as potential substrates of hPEPT1 transporter", J. Med. Chem., vol. 48, pp. 1274-1277 (2005).

Stanczak, A. et al., "Prodrugs and soft drugs", Pharmacological Rep., vol. 58, pp. 599-613 (2006).

Stella V. et al. "Prodrugs, Challenges and Rewards", Table of Contents, Springer (2007), 7 pages.

Thomas, M. et al., "Formation of functional tissue from transplanted adrenocortical cells expressing telomerase reverse transcriptase", Nature Biotechnol., vol. 18(1), pp. 39-42 (2000).

Valcavi, U. "Synthesis and biological activity of digitoxigenin aminoesters", Il Farmaco Ed. Sc., vol. 36, pp. 971-982 (1981).

Vasa, M. et al., "Nitric oxide activates telomerase and delays endothelial cell senescence", Circ. Res., vol. 87(7), pp. 540-542 (2000).

Vig et al., "Amino Acid Ester Prodrugs of Floxuridine: Synthesis and Effects of Structure, Stereochemistry, and Site of Esterification on the Rate of Hydrolysis," Pharma. Res., vol. 20, 1381-1388 (2003).

Wang et al., "An Improved Oxidative Cleavage Method for Large Scale Preparation of Some Acid-labile Aglycones from Glycosides," Journal of the Chinese Chemical Society, 2002, vol. 49, pp. 103-106.

Wang, D. et al., "Simultaneous analysis of seven astragalosides in Radix astragali and related preparations by liquid chromatography coupled with electrospray ionization time-of-flight mass spectrometry", J. Sep. Sci., vol. 29, pp. 2012-2022 (2006).

Wang, Y-P. et al., "Effect of astragaloside IV in T, B lymphocyte proliferation and peritoneal macrophage function in mice", Acta Pharmalogica Sinica, vol. 23(3), pp. 263-266 (2002).

Xiao, H. et al., "Total analytical method for Radix astragali extract using two-binary multi-segment gradient elution liquid chromatography", J. Sep. Sci., vol. 24, pp. 186-196 (2001).

Yang, J. et al., "Human endothelial cell life extension by telomerase expression", J. Biol. Chem. vol. 274, pp. 26141-26148 (1999).

Yang, J. et al., "Telomerized human microvasculature is functional in vivo", Nat. Biotechnol., vol. 19, pp. 219-224 (2001).

Yasukawa, K. et al., "Sterol and triterpene derivatives from plants inhibit the effects of a tumor promoter, and sitosterol and betulinic acid inhibit tumor formation in mouse skin two-stage carcinogensesis", Oncology, vol. 48(1), pp. 72-76 (1991).

Yokogawa, K. "Pharmacokinetic advantage of an intranasal preparation of a novel anti-osteoporosis drug, L-Asp-hexapeptide-conjugated estradiol", Biol. Pharm. Bull., vol. 29(6), pp. 1229-1233 (2006).

Yudoh, K. et al., "Reconstituting telomerase activity using the telomerase catalytic subunit prevents the telomere shorting and replicative senescence in human osteoblasts", J. Bone Mineral Res., vol. 16(8), pp. 1453-1464 (2001).

Zhang, J. et al., "New drugs derived from medicinal plants", Therapie, vol. 57(2), pp. 137-150 (2002).

Zhang, W. et al., "Regulation of the fibrinolytic potential of cultured human umbilical vein endothelial cells: astragaloside IV downregulates plasminogen activator inhibitor 1 and upregulates tissue-type plasminogen activator expression", J. Vasc. Res., vol. 34(4), pp. 273-280 (1997).

Zhao, K. et al., "Enhancement of the immune response in mice by Astragalus membranaceus extracts", Immunopharmacol., vol. 20, pp. 225-234 (1990).

Zheng, Z, et al., "Studies on chemical constituents and immunological function activity of hairy root of Astragalus membranaceus", Chinese J, Biotech., vol. 14(2), pp. 93-97 (1998).

\* cited by examiner

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aatccgtcga gcagagtt                                                 18

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgcggctta cccttaccct taccctaacc                                    30

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aatccgtcga gcagagttaa aaggccgaga agcgat                             36

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atcgcttctc ggccttttt                                                18

COMPOSITIONS AND METHODS FOR INCREASING TELOMERASE ACTIVITY

REFERENCE TO PRIOR APPLICATIONS

This application is a continuation of and claims the benefit to U.S. application Ser. No. 12/781,515 filed May 17, 2010, which claims the benefit of U.S. Provisional Application No. 61/179,305 filed May 18, 2009, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 26, 2013, is named 2208534.00122US3_SL.txt and is 1,381 bytes in size.

FIELD OF THE INVENTION

The present invention relates to methods and compositions for increasing telomerase activity in cells.

BACKGROUND OF THE INVENTION

Telomerase is a ribonucleoprotein that catalyzes the addition of telomeric repeats to the ends of telomeres. Telomeres are long stretches of repeated sequences that cap the ends of chromosomes and are believed to stabilize the chromosome. In humans, telomeres are typically 7-10 kb in length and comprise multiple repeats of the sequence -TTAGGG-. Telomerase is not expressed in most adult cells, and telomere length decreases with successive rounds of replication. After a certain number of rounds of replication, the progressive shortening of the telomeres results in the cells entering a telomeric crisis stage, which in turn leads to cellular senescence. Certain diseases are associated with rapid telomeric loss, resulting in premature cell senescence. Expression of the gene encoding the human telomerase protein in human cells has been shown to confer an immortal phenotype, presumably through bypassing the cells' natural senescence pathway. In addition, expression of the telomerase gene in aging cells with short telomeres has been shown to produce an increase in telomere length and restore a phenotype typically associated with younger cells.

Somatic cells, in contrast to tumor cells and certain stem cells, have little or no telomerase activity and stop dividing when the telomeric ends of at least some chromosomes have been shortened to a critical length, leading to programmed cellular senescence (cell death). Since the loss of telomeric repeats in somatic cells, leading to senescence, is augmented by low telomerase activity, induction of telomerase activity, which has the effect of adding arrays of telomeric repeats to telomeres, thereby imparts to mortal somatic cells increased replicative capacity, and imparts to senescent cells the ability to proliferate and appropriately exit the cell cycle upon repair of damaged tissue.

Methods of increasing telomerase activity therapeutically have been investigated by, for example, Bodnar *Science* 279 (5349):349-52 (Jan. 16, 1998)); White, PCT Int. Appl. Pubn. No. WO 2000/08135 (February 2000)); Hannon et al. PCT Int. appl. Pubn. WO 99/35243 (July 1999) and PCT Int. Appl. Pubn. No. WO 2000/0312238 (June 2000)); Franzese et al. *Lifescience* 69(13) 1509-20 (2001), and Yudoh et al. *J. Bone and Mineral Res.* 16(8):1453-1464 (2001). In these reports, telomerase activity is generally increased by overexpression of hTERT, the gene encoding the protein component of human telomerase, or by expression of proteins which mediate assembly of telomerase, e.g. heat shock proteins (White, PCT No. WO2000/08135). Franzese et al. reported that Saquinavir, a protease inhibitor prescribed for treatment of HIV infection, increased telomerase activity in peripheral blood mononuclear cells; Vasa et al. *Circ Res*, 87(7) 540-2 (2000) described activation of telomerase, and a resulting delay in endothelial senescence, by administration of a nitric oxide (NO) precursor.

Various saponins of the astragaloside family have been reported as having various biological effects including increasing telomerase activity, Harley et al. PCT Int Appl. Pubn. No. WO2005/000245. It would be beneficial to develop a compound which was an effective telomerase activator.

SUMMARY OF THE INVENTION

The invention described herein is generally related to compounds and methods for increasing telomerase activity in cells and compositions for use in such methods. Such methods and compositions may be used on cells in cell culture, i.e. in vitro or ex vivo, or in vivo, such as cells growing in tissues of a subject, including human subjects and non-human mammals.

Various saponins of the astragaloside family had previously been reported as having various biological effects including increasing telomerase activity, Harley et al. PCT Int Appl. Pubn. No. WO2005/000245. However, the inventors have found that the bioavailability of the naturally occurring compounds described therein including cycloastragenol is very limited when administered orally to certain mammalian species. It was not clear whether the limited bioavailability was attributable to low uptake of the compounds by the mammals, or high metabolism of the compounds in certain species of mammals or a combination of both. Such low bioavailability means that the compounds previously described were very much less effective as an oral telomerase activator in certain mammalian species.

It was determined that there was a need for a new compounds which would be potent telomerase activators and which were also orally available across a number of mammalian species and which had an improved half life in representative mammalian species. The chemical compounds described herein possess these desired properties.

In particular embodiments, the compositions comprise a compound of formula I and pharmaceutical salts thereof as described below. Aspects of the invention include formulations of such compounds for use in pharmaceutical applications, in particular in applications where increasing telomerase activity in cells is shown to be, or expected to be, beneficial. Methods of using the compounds and formulations thereof for such applications are also provided, including methods for applying or administering such formulations after the need for, or advantage of, increasing telomerase activity in cells or tissues has been determined.

The present invention includes, in one aspect, a compound the formula I:

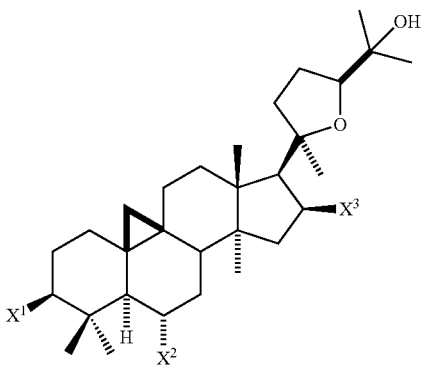

wherein $X^1$, is selected from keto (=O), hydroxy (—OH), and

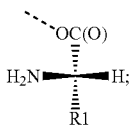

wherein $X^2$ is selected from keto (=O), hydroxy (—OH), and

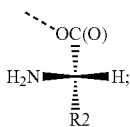

wherein $X^3$ is selected from keto (=O), hydroxy (—OH), and

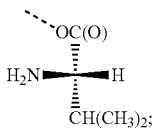

wherein at least one of $X^1$, $X^2$ or $X^3$ is

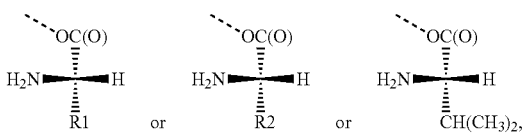

respectively;
wherein $R^1$ or $R^2$ are independently selected from —CH(CH$_3$)$_2$, and —CH(CH$_3$)CH$_2$CH$_3$;
and pharmaceutically acceptable salts thereof.

In one embodiment $X^1$ is —OC(O)CH(NH2)$R^1$ wherein $R^1$ is selected from the group consisting of —CH(CH$_3$)$_2$ or —CH(CH$_3$)$_2$CH$_3$ In another embodiment $X^2$ is —OC(O)CH(NH$_2$)$R^2$ wherein $R^2$ is selected from the group consisting of —CH(CH$_3$)$_2$ or —CH(CH$_3$)$_2$CH$_3$.

In one embodiment at least one of $X^1$, $X^2$ or $X^3$ is —OC(O)CH(NH$_2$)CH(CH$_3$)$_2$. In another embodiment both $X^1$ and $X^2$ are —OC(O)CH(NH$_2$)CH(CH$_3$)$_2$.

In one embodiment at least one of $X^1$ or $X^2$ is —OC(O)CH(NH$_2$)CH(CH$_3$)CH$_2$CH$_3$. In another embodiment both $X^1$ and $X^2$ are —OC(O)CH(NH$_2$)CH(CH$_3$)CH$_2$CH$_3$.

In selected embodiments of formula I, $X^1$ is a —OC(O)CH(NH$_2$)CH(CH$_3$)$_2$ and $X^2$ and $X^3$ are independently selected from hydroxy and keto. In further embodiments, $X^2$ is —OC(O)CH(NH$_2$)CH(CH$_3$)$_2$ and $X^1$ and $X^3$ are independently selected from hydroxy and keto. In further embodiments, $X^3$ is —OC(O)CH(NH$_2$)CH(CH$_3$)$_2$ and $X^1$ and $X^2$ are independently selected from hydroxy and keto. In further embodiments, $X^1$ and $X^2$ are both —OC(O)CH(NH$_2$)CH(CH$_3$)$_2$ and $X^3$ is OH. In still further embodiments, $X^1$ is —OC(O)CH(NH$_2$)CH(CH$_3$)$_2$ and each of $X^2$ and $X^3$ are OH. In still further embodiments, $X^2$ is —OC(O)CH(NH$_2$)CH(CH$_3$)$_2$ and each of $X^1$ and $X^3$ are OH.

In selected embodiments of formula I, $X^1$ is a —OC(O)CH(NH$_2$)CH(CH$_3$)CH$_2$CH$_3$ and $X^2$ and $X^3$ are independently selected from hydroxy and keto. In further embodiments, $X^2$ is —OC(O)CH(NH$_2$)CH(CH$_3$)CH$_2$CH$_3$ and $X^1$ and $X^3$ are independently selected from hydroxyl and keto. In further embodiments, $X^1$ and $X^2$ are both —OC(O)CH(NH$_2$)CH(CH$_3$)CH$_2$CH$_3$ and $X^3$ is OH. In still further embodiments, $X^1$ is —OC(O)CH(NH$_2$)CH(CH$_3$)CH$_2$CH$_3$ and each of $X^2$ and $X^3$ are OH. In still further embodiments, $X^2$ is —OC(O)CH(NH$_2$)CH(CH$_3$)CH$_2$CH$_3$ and each of $X^1$ and $X^3$ are OH.

In some embodiments of formula I, the pharmaceutically acceptable salt is a hydrochloride salt.

It is contemplated that the amino acid substituents are the L or naturally occurring stereoisomer.

Exemplary compounds of formula I include those designated herein as: 2-(L)-amino-3-methyl-butyric acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester (designated herein as 4); 2-(L)-amino-3-methyl-butyric acid 6α(2-amino-3-methyl-butyryloxy)-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester (designated herein as 7); 2-(L)-tert-butoxycarbonylamino-3-methyl-butyric acid 3b-acetoxy-16b-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-6a-yl ester (designated herein as 12) 2-(L),3-dimethyl-pentanoic acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester (designated herein as 14), 2-(L)-Amino-3-methyl-butyric acid, 16β-hydroxy-17-[5-(1-hydroxy-1-methyl-ethyl)-2-methyl-tetrahydro-furan-2-yl]-4,4,13,14-tetramethyl-3-oxo-tetradecahydro-cyclopropa[9,10]cyclopenta[a]phenanthren-6α-yl ester (designated herein as 30), 2-(L)-Amino-3-methyl-pentanoic acid 6α-(2-amino-3-methyl-pentanoyloxy)-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester (designated herein as 32); 2-(L)-Amino-3-methyl-butyric acid 3β,6α-dihydroxy-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-16β-yl ester (designated herein as 36) and pharmaceutically acceptable salts thereof.

Exemplary compounds of formulas I include those designated herein as: 2-(L)-amino-3-methyl-butyric acid 6α, 16β-dihydroxy-17-[5-(1-hydroxy-1-methyl-ethyl)-2-methyl-tetrahydro-furan-2-yl]-4,4,13,14-tetramethyl-tetradecahydrocyclopropa[9,10]cyclopenta[a]phenanthren-3β-yl ester hydrochloride salt; 2-(L)-amino-3-methyl-butyric acid 6α-(2-amino-3-methyl-butyryloxy)-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10] cyclopenta[a]phenanthren-3β-yl ester hydrochloride salt; 2-(L)-tert-butoxycarbonylamino-3-methyl-butyric acid 3b-acetoxy-16b-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a] phenanthren-6a-yl ester hydrochloride salt; 2-(L),3-dimethyl-pentanoic acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10] cyclopenta[a]phenanthren-3β-yl ester hydrochloride salt, 2-(L)-Amino-3-methyl-butyric acid, 16β-hydroxy-17-[5-(1-hydroxy-1-methyl-ethyl)-2-methyl-tetrahydro-furan-2-yl]-4,4,13,14-tetramethyl-3-oxo-tetradecahydro-cyclopropa[9,10]cyclopenta[a]phenanthren-6α-yl ester hydrochloride salt; 2-(L)-Amino-3-methyl-pentanoic acid, 6α-(2-amino-3-methyl-pentanoyloxy)-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a] phenanthren-3β-yl ester hydrochloride salt or 2-(L)-Amino-3-methyl-butyric acid, 3β, 6α-dihydroxy-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-16β-yl ester hydrochloride salt.

A compound of formula I above, when formulated in a solvent, is effective to produce a level of telomerase activity in keratinocytes or PBMCs, as measured in a TRAP assay, at least 50% greater, at least 70% greater, at least 80% greater, or at least 90% greater than the level in said cells treated with said solvent, as measured in a TRAP assay as described herein. In further embodiments, the compound is effective to produce a level of telomerase activity in keratinocytes or PBMCs, as measured in a TRAP assay, at least 100% greater than the level in said cells treated with said solvent, as measured in a TRAP assay as described herein.

The present invention includes, in one aspect, a method of increasing telomerase activity in a cell or tissue. The method comprises contacting the cell or tissue with an isolated compound of formula I. The method may further comprise the preliminary step of identifying a cell or tissue in which an increase in telomerase activity is desired.

The method of contacting an isolated compound of formula I with a cell or tissue may comprise, prior to said contacting, identifying a cell or tissue in which an increase in telomerase activity is desired. Benefits to be realized by increasing telomerase activity in a cell or tissue include, for example, enhancement of the replicative capacity and/or life span of said cell or cells within said tissue.

The method may include identifying, determining or diagnosing a condition in a subject such that increasing telomerase activity in the cells or tissue of the subjects is desired, and administering the compound to the subject. The subject is a mammalian subject, such as a domestic animal such as a dog, cat, mouse, rat, monkey or a human subject or patient.

Such conditions or diseases for prevention or treatment may include, for example, viral and opportunistic infections including HIV, various degenerative diseases, such as neurodegenerative disease, degenerative disease of the bones or joints, and connective tissues, macular degeneration, diabetic retinopathy, cardiovascular diseases including central and peripheral vascular disease, Crohn's disease and other immunological conditions, liver diseases including fibrosis and cirrhosis, lung diseases including pulmonary fibrosis, asthma, emphysema, and COPD, hematopoietic disorders (including anemia, thrombocytopenia, neutropenia and other cytopenias), chronic inflammatory gastrointestinal diseases such as Barretts esophagus, any disorder related to loss of proliferative capacity in stem cell or progenitor cell populations. Such conditions may include bone marrow failure syndrome, aplastic anemia, myelodysplastic anemia or myelodysplastic syndrome. Such conditions also include wounds or other acute or chronic conditions of the skin and its appendages, such as, for example, a burn, an abrasion, an incision, a graft, a lesion caused by an infectious agent, a chronic venous ulcer, a diabetic ulcer, a compression or decubitus ulcer, a mucosal ulcer, keloid formation, hair or pigment loss, and other structural aberrations of the skin and its appendages. Such conditions also include cancer and precancerous conditions in which low telomerase or shortened telomeres are associated with genomic instability, or increased mutation rates, or loss of tumor suppressor functions, and consequently subjects have an increased risk of tumor initiation, tumor progression, or tumor recurrence.

The invention provides methods of preventing or treating a condition in a patient, such as those noted above, by increasing telomerase activity in cells or tissue of the patient, the method comprising administering to a patient in need of such prevention or treatment, an isolated compound of formula I as defined above. The compositions may be administered by various routes, for example, orally, topically, parenterally, subcutaneously, inhalation and intravenously.

In a further embodiment, the invention provides a method of treating an acute or chronic condition of the epidermis, comprising contacting epidermal cells with a topical formulation of an isolated compound of formula I as defined above.

The cells with which the formulation is contacted may also include explant cells which are contacted ex vivo, e.g. for cell-based therapies, or other cells in culture. Accordingly, the invention provides a method of enhancing replicative capacity and improved functional capacity of cells in vitro or ex vivo, comprising contacting said cells with an effective amount of a composition comprising a compound of formula I as defined above, including selected embodiments of the compounds as defined above. In general, the cells are mammalian cells; in selected embodiments, the cells are stem cells, such as bone marrow stem or progenitor cells, bone marrow stromal cells, epidermal and epithelial stem cells from skin and other tissues including gut, liver, and pancreas, islet precursor cells, neurosphere cells, adrenocortical cells, muscle satellite cells, mesenchymal stem and progenitor cells including osteoblast precursors, retinal pigmented epithelial cells, endothelial precursor cells, pericytes, and immune cells capable of clonal expansion including memory and naive T (CD4 and CD8) and B cells.

In a further embodiment, the invention provides a method of enhancing transplantation of a tissue from a living donor or cadaver to a living patient comprising contacting the transplantation tissue with an isolated compound of formula I as defined above. In a further embodiment, the invention provides a method of enhancing transplantation of a tissue from a donor to a living patient comprising administering the isolated compound of formula I as defined above to the patient either before, simultaneous with, or for a period of time after the transplantation of the tissue. The transplanted tissue may be solid tissue, such as a kidney, heart, lungs etc., or hematopoietic tissue such as, without limitation, blood cells such as leukocytes, lymphocytes or hematopoietic precursor cells which may be derived fro bone marrow.

In one embodiment, the invention provides a pharmaceutical composition comprising, in a pharmaceutically acceptable vehicle, a compound of formula I as depicted above.

In another embodiment, the invention provides a topical pharmaceutical formulation of an isolated compound of formula I, as defined above. Selected embodiments of an isolated compounds are also defined above. The topical formulation typically comprises one or more components selected from the group consisting of an emulsifier, a carrier (e.g. liposomes), a thickener, and a skin emollient. Such compositions may be used for treatment of wounds or other acute or chronic conditions of the epidermis.

Use of an isolated compound of formula I as defined above, including selected embodiments as described above, in the manufacture of a medicament for preventing or treating disease or condition. Use of an isolated compound of formula I as defined above, including selected embodiments as described above, in the manufacture of a medicament for preventing or treating disease subject to prevention or treatment by increasing telomerase activity in a cell or tissue. Use of an isolated compound of formula I as defined above, including selected embodiments as described above, for preventing or treating a disease or condition. Use of an isolated compound of formula I as defined above, including selected embodiments as described above, for preventing or treating a disease subject to prevention or treatment by increasing telomerase activity in a cell or tissue The use may further comprise the preliminary step of identifying a cell or tissue in which an increase in telomerase activity is desired. Benefits to be realized by increasing telomerase activity in a cell or tissue include, for example, enhancement of the replicative capacity and/or life span of said cell or cells within said tissue and enhancement of functional capacity.

The use may include identifying, determining or diagnosing a condition or disease in a subject such that increasing telomerase activity in the cells or tissue of the subject is desired. Such conditions may include, for example, viral and opportunistic infections including HIV, various degenerative diseases, such as neurodegenerative disease, degenerative disease of the bones or joints and connective tissues, diabetic retinopathy, macular degeneration, cardiovascular diseases including central and peripheral vascular disease, Crohn's disease and other immunological conditions, liver diseases including fibrosis and cirrhosis, lung disease including pulmonary fibrosis, asthma, emphysema, and COPD, hematopoietic disorders (including anemia, thrombocytopenia, neutropenia and other cytopenias), chronic inflammatory gastrointestinal diseases such as Barretts esophagus, any disorder related to loss of proliferative capacity in stem cell or progenitor cell populations. Such conditions may include bone marrow failure syndrome, aplastic anemia, myelodysplastic anemia or myelodysplastic syndrome. Such conditions also include wounds or other acute or chronic conditions of the skin and its appendages, such as, for example, a burn, an abrasion, an incision, a graft, a lesion cause by an infections agent, a chronic venous ulcer, a diabetic ulcer, a compression or decubitus ulcer, a mucosal ulcer, keloid formation, hair or pigment loss, and other structural aberrations of the skin and its appendages. Such conditions also include cancer and precancerous conditions in which low telomerase or shortened telomeres are associated with genomic instability, or increased mutation rates, or loss of tumor suppressor functions, and consequently subjects have an increase risk of tumor initiation, tumor progression, or tumor recurrence.

Similarly, use of an isolated compound of formula I, as defined above, including selected embodiments as described above, for the manufacture of a medicament for treatment of a chronic or acute condition of the epidermis is contemplated. Another embodiment is the use of an isolated compound of formula I, as defined above, including selected embodiments as described above, for the treatment of a of a chronic or acute condition of the epidermis.

These and other objects and features of the invention will become more fully apparent when the following detailed description of the invention is read in conjunction with the accompanying drawings.

DETAILED DESCRIPTION OF THE INVENTION

I. Definitions

Figure 1:
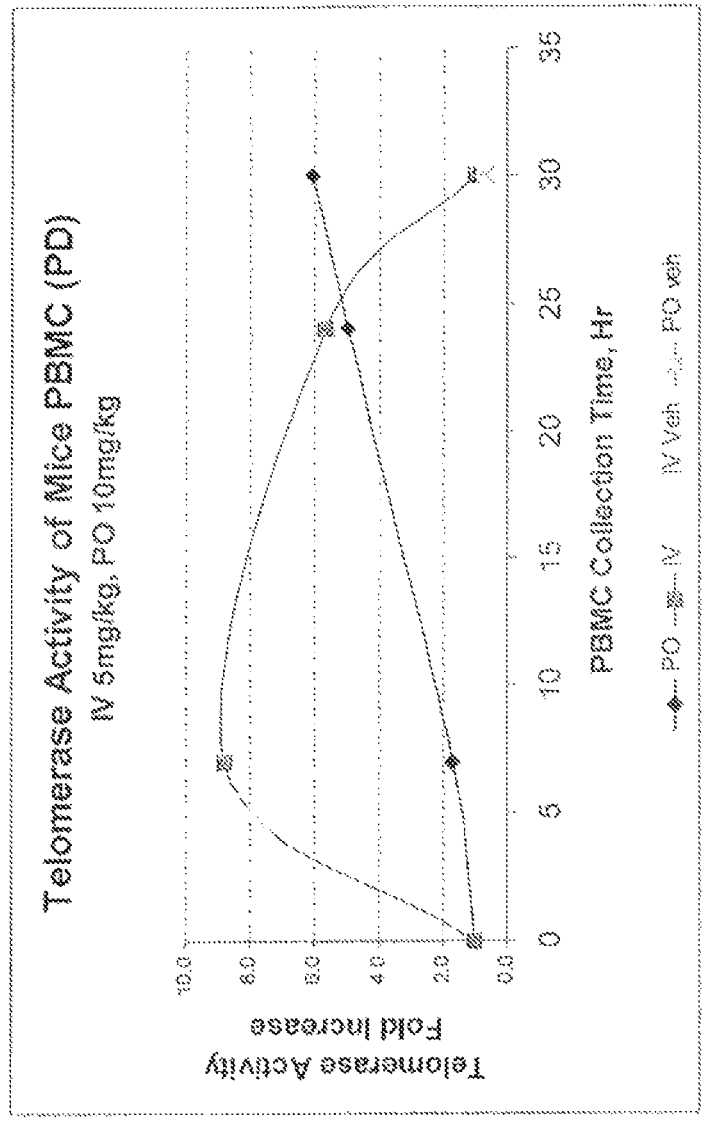
FIG. 1 shows an increase of telomerase activity in mice peripheral blood mononuclear cells (PBMC) after one dose of compound 4 C3-(L)-valyl-cycloastragenol, as measured in a TRAP assay.

The following terms, as used herein, have the meanings given below, unless indicated otherwise.

A general carbon atom numbering scheme used for nomenclature of compounds described herein is shown below.

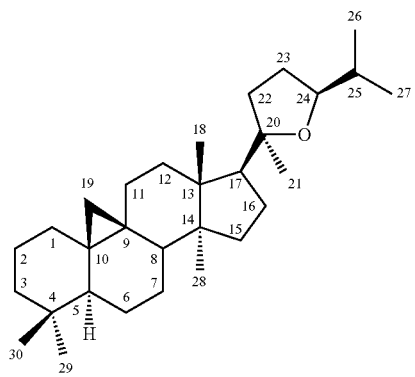

Thus C3-(L) valyl cycloastragenol refers to the (L) valine attached through an ester bond to carbon 3 of the compound structure.

"$C_{1-5}$ Alkyl" refers to a fully saturated acyclic monovalent radical containing carbon and hydrogen, which may be branched or linear having from 1 to 5 carbon atoms. Examples of alkyl groups are methyl, ethyl, n-propyl, n-butyl, isopropyl, iso-butyl, sec-butyl, tert-butyl.

"" means =O.

"Hydroxy" means —OH.

The term "amino acid" comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids. The term also comprises natural and unnatural amino acids bearing a conventional amino protecting group (e.g. acetyl or benzyloxycarbonyl). Other suitable protecting amino protecting groups are known to those skilled in the art (See for example, T. W. Green, *Protecting Groups in Organic Synthesis; Third Edition*, Wiley, New York 1999). Unless otherwise stated amino acid substituents are attached to the cycloastragenol through their carboxy groups via ester linkages. Thus C3-(L) valyl cycloastragenol is C3-(L) valyl cycloastragenol ester.

The term "isomer" includes, but is not limited to optical isomers and analogs, structural isomers and analogs, conformational isomers and analogs and the like.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form or mixtures thereof, of a compound of the invention which possess the useful properties described herein, it being well known in the art how to prepare optically active forms (for example, by resolution of the racemic form by recrystallization techniques, by synthesis form optically-active starting materials, by chiral synthesis, or by chromatographic separation using a chiral stationary phase) and how to determine the ability of the compounds to increase telomerase activity using the tests described herein. In one embodiment the amino acids are in the naturally occurring (L) form.

The invention includes "pharmaceutically acceptable salts" of the compounds of this invention, which may be produced, in one embodiment, to form alkali metal salts and to form free addition salts of free acids or free bases. Suitable pharmaceutically acceptable acid addition salts of compounds of this invention may be prepared from an inorganic acid or from an organic acid. In one embodiment, examples of inorganic acids are hydrochloric, hydrobromic, hydroiodic, nitric, carbonic, sulfuric and phosphoric acid. In one embodiment, organic acids may be selected from aliphatic, cycloaliphatic, aromatic, araliphatic, heterocyclic, carboxylic and sulfonic classes of organic acids, examples of which are formic acid, acetic, propionic, succinic, glycolic, gluconic, lactic, malic, tartaric, citric, ascorbic, glucornoic, maleic, fumaric, pyruvic, aspartic, glutamic, benzoic, antranilic, oxalic, mesylic, salicyclic, stearic and galacturonic acid. In one embodiment, suitable pharmaceutically-acceptable base addition salts of compounds of this invention include metallic salts made from aluminum, calcium, lithium, magnesium, potassium, sodium and zinc or organic salts made from N,N'-dibenzylethylenediamine, choline, chloroprocaine, ethanolamine, ethylenediamine, and procain. All of these salts may be prepared by conventional means from the corresponding compounds. Pharmaceutically acceptable salts can be prepared in other embodiments by treatment with inorganic bases, for example, sodium hydroxide. In another embodiment, esters of the compounds can be made with aliphatic and aromatic carboxylic acids, for example, acetic acid and benzoic acid esters.

"Stem cells" refer to relatively undifferentiated cells of a common lineage that retain the ability to divide and cycle throughout postnatal life, to provide cells that can differentiate further and become specialized (e.g., stem cells in basal layers of skin or in haematopoetic tissue, such as primitive cells in the bone marrow form which all the various types of blood cell are derived.

By "effective to increase telomerase activity in a cell", with reference to a compound, is meant that a composition containing the compound at a concentration of 10 μM or less is effective to produce a level of telomerase activity in a keratinocyte or fibroblast cell, as measured in a telomerase activity assay (e.g. TRAP) assay as described herein, which is greater, by a factor of at least 1.5 (i.e. at least 50% greater), than the level produced by a similar formulation not containing the compound, as measured in a TRAP assay. In some embodiments, the compound is effective, at a concentration of 10 μM or less, to produce a level of telomerase activity in such a cell, as measured in a TRAP assay as described herein, which is greater by a factor of at least 2 (i.e. at least 100% greater) than the level produced by a similar formulation not containing the compound.

A "subject" is a mammal. The subject may be a domestic mammal for example a dog, cat mouse, rat, monkey etc. The subject or patient may be a human.

In reference to administration of a compound to a patient, an "effective amount" refers to an amount effective to increase telomerase activity in the cells or tissue of the patient, such that a desired therapeutic result is achieved. In reference to treatment of cells in vitro or ex vivo, an "effective amount" refers to an amount effective to increase telomerase activity in the cells, thereby increasing the replicative capacity and/or life span of the cells.

In concentrations expressed herein as % (w/v), 100% (w/v) corresponds to 1 g solute/ml solvent. For example, 0.1% (w/v)=1 mg/ml.

A "formulation of an isolated compound" refers to a formulation prepared by combining the isolated compound with one or more other ingredients (which may be active or inactive ingredients) to produce the formulation. The phrase "isolated compound" refers to a compound that (prior to the formulation) has been produced by a process involving one or more chemical synthesis steps, resulting in a preparation of the compound that is of not less than 80% (w/w) purity.

II. Methods and Compositions for Increasing Telomerase Activity

In accordance with the present invention, compositions and methods are provided for increasing telomerase activity in a cell.

It has been found that the compounds of the present invention are able to increase telomerase activity in cells and are readily biologically available when administered to mammals either intravenously or orally.

In accordance with the method, a cell or tissue is contacted with an isolated compound of formula I as disclosed herein, in an amount effective to increase telomerase activity in the cell or tissue, relative to the level of telomerase activity in the cell or tissue in the absence of the compound. The method may also include a preliminary step of identifying a cell or tissue in which an increase in telomerase activity is desired.

The present invention includes, in one aspect, a compound of the formula I:

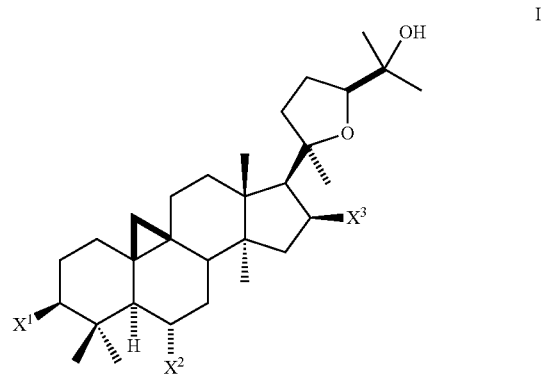

wherein $X^1$, is selected from keto (=O), hydroxy, and

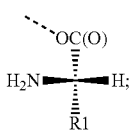

wherein $X^2$ is selected from keto (═O), hydroxy, and

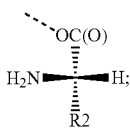

wherein $X^3$ is selected from keto (═O), hydroxy, and

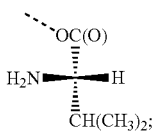

wherein at least one of $X^1$, $X^2$ or $X^3$ is

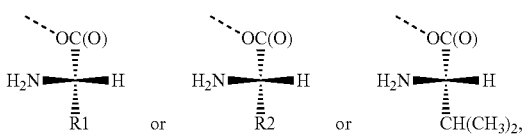

respectively;
wherein $R^1$ and $R^2$ are independently selected from —CH$(CH_3)_2$, and $CH(CH_3)CH_2CH_3$;
and pharmaceutically acceptable salts thereof.

In one embodiment $X^1$ is —OC(O)CH(NH$_2$)R$^1$ wherein R$^1$ is selected from the group consisting of —CH(CH$_3$)$_2$ or —CH(CH$_3$)$_2$CH$_3$ In another embodiment $X^2$ is —OC(O)CH(NH$_2$)R$^2$ wherein R$^2$ is selected from the group consisting of —CH(CH$_3$)$_2$ or —CH(CH$_3$)$_2$CH$_3$ In one embodiment at least one of $X^1$, $X^2$ or $X^3$ is —OC(O)CH(NH$_2$)CH(CH$_3$)$_2$. In another embodiment both $X^1$ and $X^2$ are —OC(O)CH(NH$_2$)CH(CH$_3$)$_2$.

In one embodiment at least one of $X^1$ or $X^2$ is —OC(O)CH(NH$_2$)CH(CH$_3$)CH$_2$CH$_3$. In another embodiment both $X^1$ and $X^2$ are —OC(O)CH(NH$_2$)CH(CH$_3$)CH$_2$CH$_3$.

In selected embodiments of formula I, $X^1$ is a —OC(O)CH(NH$_2$)CH(CH$_3$)$_2$ and $X^2$ and $X^3$ are independently selected from hydroxy and keto. In further embodiments, $X^2$ is —OC(O)CH(NH$_2$)CH(CH$_3$)$_2$ and $X^1$ and $X^3$ are independently selected from hydroxy and keto. In further embodiments, $X^3$ is —OC(O)CH(NH$_2$)CH(CH$_3$)$_2$ and $X^1$ and $X^2$ are independently selected from hydroxy and keto. In further embodiments, $X^1$ and $X^2$ are both —OC(O)CH(NH$_2$)CH(CH$_3$)$_2$ and $X^3$ is OH. In still further embodiments, $X^1$ is —OC(O)CH(NH$_2$)CH(CH$_3$)$_2$ and each of $X^2$ and $X^3$ are OH. In still further embodiments, $X^2$ is —OC(O)CH(NH$_2$)CH(CH$_3$)$_2$ and each of $X^1$ and $X^3$ are OH.

In selected embodiments of formula I, $X^1$ is a —OC(O)CH(NH$_2$)CH(CH$_3$)CH$_2$CH$_3$ and $X^2$ and $X^3$ are independently selected from hydroxy and keto. In further embodiments, $X^2$ is —OC(O)CH(NH$_2$)CH(CH$_3$)CH$_2$CH$_3$ and $X^1$ and $X^3$ are independently selected from hydroxyl and keto. In further embodiments, $X^1$ and $X^2$ are both —OC(O)CH(NH$_2$)CH(CH$_3$)CH$_2$CH$_3$ and $X^3$ is OH. In still further embodiments, $X^1$ is —OC(O)CH(NH$_2$)CH(CH$_3$)CH$_2$CH$_3$ and each of $X^2$ and $X^3$ are OH. In still further embodiments, $X^2$ is —OC(O)(NH$_2$)CH(CH$_3$)CH$_2$CH$_3$ and each of $X^1$ and $X^3$ are OH. In still further embodiments, $X^2$ is —OC(O)CH(NH$_2$)CH(CH$_3$)CH$_2$CH$_3$ and each of $X^1$ and $X^3$ are OH.

In some embodiments of formula I, the pharmaceutically acceptable salt is a hydrochloride salt.

Exemplary compounds of formula I include those designated herein as: 2-(L)-amino-3-methyl-butyric acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester (designated herein as 4); 2-(L)-amino-3-methyl-butyric acid 6α(2-3-methyl-butyryloxy)-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester (designated herein as 7); 2-(L)-tert-butoxycarbonylamino-3-methyl-butyric acid 3b-acetoxy-16b-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-6a-yl ester (designated herein as 12) 2-(L),3-dimethyl-pentanoic acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester (designated herein as 14); 2-(L)-Amino-3-methyl-butyric acid, 16β-dihydroxy-17-[5-(1-hydroxy-1-methyl-ethyl)-2-methyl-tetrahydro-furan-2-yl]-4,4,13,14-tetramethyl-3-oxo-tetradecahydro-cyclopropa[9,10]cyclopenta[a]phenanthren-6α-yl ester (designated herein as 30), 2-(L)-Amino-3-methyl-pentanoic acid 6α-(2-amino-3-methyl-pentanoyloxy)-16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester (designated herein as 32); 2-(L)-Amino-3-methyl-butyric acid 3β,6α-dihydroxy-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-16β-yl ester (designated herein as 36) and pharmaceutically acceptable salts thereof.

Exemplary compounds of formulas I include those designated herein as: 2-(L)-amino-3-methyl-butyric acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester hydrochloride salt; 2-(L)-amino-3-methyl-butyric acid 6α-(2-amino-3-methyl-butyryloxy)-16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester hydrochloride salt; 2-(L)-tert-butoxycarbonylamino-3-methyl-butyric acid 3b-acetoxy-16b-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-6a-yl ester hydrochloride salt; 2-(L),3-dimethyl-pentanoic acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester hydrochloride salt, 2-(L)-Amino-3-methyl-butyric acid, 16β-hydroxy-17-[5-(1-hydroxy-1-methyl-ethyl)-2-methyl-tetrahydro-furan-2-yl]-4,4,13,14-tetramethyl-3-oxo-tetradecahydro-cyclopropa[9,10]cyclopenta[a]phenanthren-6α-yl ester hydrochloride salt; 2-(L)-Amino-3-methyl-pentanoic acid, 6α-(2-amino-3-methyl-pentanoyloxy)-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester hydrochloride salt or 2-(L)-Amino-3-methyl-butyric acid, 3β,6α-dihydroxy-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-16β-yl ester hydrochloride salt.

In one embodiment, the compound is selected from the following compounds of formula I:

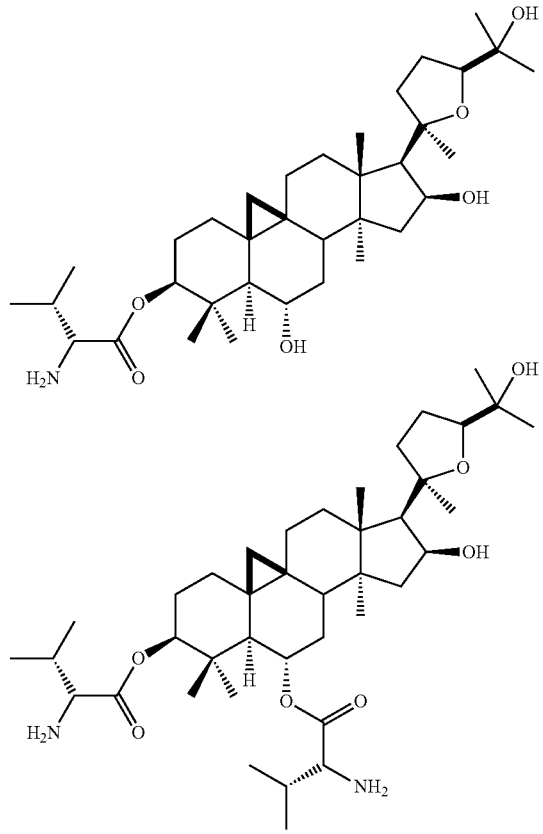

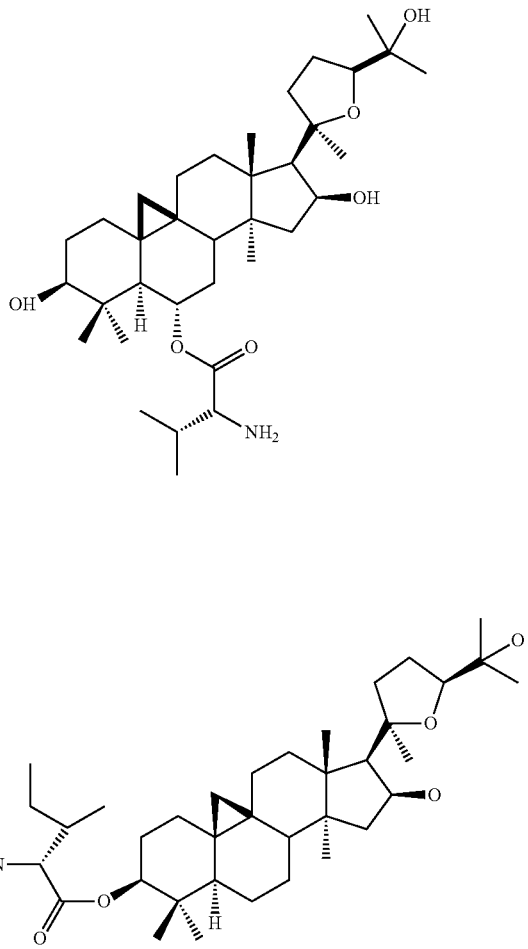

and pharmaceutically acceptable salts thereof.

Exemplary compounds of formula I include the compounds in the following table, with reference to formula I:

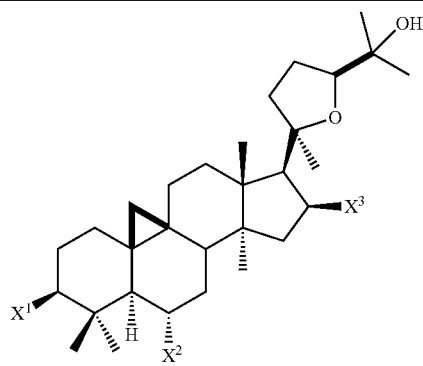

| Compound number | Name | $X^1$ | $X^2$ | $X^3$ |
|---|---|---|---|---|
| 4 | 2-(L)-amino-3-methyl-butyric acid 6α,16β-dihydroxy-17-[5-(1-hydroxy-1-methyl-ethyl)-2-methyl-tetrahydro-furan-2-yl]- | —OC(O)CH(NH$_2$)CH(CH$_3$)$_2$ | —OH | OH |

-continued

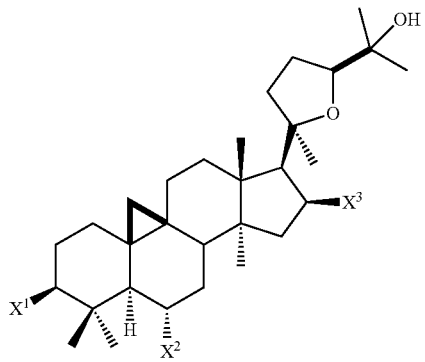

| Compound number | Name | $X^1$ | $X^2$ | $X^3$ |
|---|---|---|---|---|
| | 4,4,13,14-tetramethyl-tetradecahydro-cyclopropa[9,10]cyclopenta[a]phenanthren-3β-yl ester | | | |
| 7 | 2-(L)-Amino-3-methyl-butyric acid 6α-(2-amino-3-methyl-butyryloxy)-16β-hydroxy-17-[5-(1-hydroxy-1-methyl-ethyl)-2-methyl-tetrahydro-furan-2-yl]-4,4,13,14-tetramethyl-tetradecahydro-cyclopropa-[9,10]cyclopenta[a]penanthren-3β-yl ester | —OC(O)CH(NH$_2$)CH(CH$_3$)$_2$ | —OC(O)CH(NH$_2$)CH(CH$_3$)$_2$ | —OH |
| 12 | 2-(L)-tert-Butoxycarbonylamino-3-methyl-butyric acid 3b-acetoxy-16b-hydroxy-17-[5-(1-hydroxy-1-methyl-ethyl)-2-methyl-tetrahydro-furan-2-yl]-4,4,13,14-tetramethyl-tetradecahydro-cyclopropa-[9,10]cyclopenta[a]phenanthren-6a-yl ester | —OH | —OC(O)CH(NH$_2$)CH(CH$_3$)$_2$ | —OH |
| 14 | 2-(L),3-Dimethyl-pentanoic acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester | —OC(O)CH(NH$_2$)CH(CH$_3$)CH$_2$CH$_3$ | —OH | —OH |
| 30 | 2-(L)-Amino-3-methyl-butyric acid, 16β-hydroxy-17-[5-(1-hydroxy-1-methyl-ethyl)-2-methyl-tetrahydro-furan-2-yl]-4,4,13,14-tetramethyl-3-oxo-tetradecahydro-cyclopropa[9,10]cyclopenta[a]phenanthren-6α-yl ester | =O | —OC(O)CH(NH$_2$)CH(CH$_3$)$_2$ | —OH |
| 32 | 2-(L)-Amino-3-methyl-pentanoic acid 6α-(2-amino-3-methyl-pentanoyloxy)-16β-hydroxy-17-[5-(1-hydroxy-1-methyl-ethyl)-2-methyl-tetrahydro-furan-2-yl]-4,4,13,14-tetramethyl-tetradecahydro-cyclopropa-[9,10]cyclopenta[a]phenanthren-3β-yl ester | —OC(O)CH(NH$_2$)CH(CH$_3$)CH$_2$CH$_3$ | —OC(O)CH(NH$_2$)CH(CH$_3$)CH$_2$CH$_3$ | —OH |
| 36 | 2-(L)-Amino-3-methyl-butyric acid, 3β,6α-dihydroxy-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-16β-yl ester | —OH | —OH | —OC(O)CH(NH$_2$)CH(CH$_3$)$_2$ |

A compound of formula I above, when formulated in a solvent, is effective to produce a level of telomerase activity in keratinocytes or fibroblasts, as measured in a TRAP assay, at least 50% greater, at least 70% greater, at least 80% greater, or at least 90% greater than the level in said cells treated with said solvent, as measured in a TRAP assay as described herein. In further embodiments, the compound is effective to produce a level of telomerase activity in keratinocytes or fibroblasts, as measured in a TRAP assay, at least 100% greater than the level in said cells treated with said solvent, as measured in a TRAP assay as described herein.

The invention also provides pharmaceutical compositions comprising one or more compounds of formula I.

In a further aspect, the invention provides a method of increasing telomerase in a cell or tissue, by contacting the cell or tissue with an isolated compound of formula I. Again, the method may include the step of identifying a cell or tissue in which an increase in telomerase activity is desired.

III. Sources and Syntheses of Compounds of Formula I

The compounds of formula can be synthesized as follows.

Astragalosides I-VII can be isolated from *Astragalus membranaceus* root, as described, for example, in A. Kadota et al., JP Kokai No. 62012791 A2 (1987). As reported therein, the root tissue (8 kg), which is commercially available from various sources of beneficial herbs, is refluxed with MeOH, and the concentrated extract (200 g) is redissolved in MeOH and fractionated by column chromatography on silica gel, using CHCl$_3$/MeOH/H$_2$O mixtures as eluants. Each fraction is worked up by reverse chromatography on silica gel, using similar solvent mixtures, to give the following approximate quantities of isolated compounds: acetylastragalosie I (0.2 g), astragaloside I (3.5 g), isoastragaloside I (0.3 g), astragaloside II (2.3 g), astragaloside III (1.0 g), astragaloside IV (0.8 g), astragaloside V (0.1 g), astragaloside VI (0.3 g), and astragaloside VII (0.1 g), See also Kitagawa et al., *Chem. Pharm. Bull.* 31(2):698-708 (1983b).

Cycloastragenol (2) can be prepared by treatment of astragaloside IV (1) with methanolic HCl, followed by neutralization, standard workup, and purification by chromatography, as described in the Experimental section below (Example 1). Cycloastragenol can also be obtained by oxidative degradation (treatment with oxygen and elemental sodium) of a butanol extract of *Astragalus membranaceus*, as described by P-H Wang et al., *J. Chinese Chem. Soc.* 49:103-6 (2002).

Preparation of the various embodiments of formula I, e.g. compounds having varying degrees of esterification, alkylation or acylation, or keto groups, can be prepared according to known methods of organic synthesis, using naturally occurring and/or commercially available starting materials such as cycloastragenol, with separation of products as needed. Several examples are given in the Experimental section below.

IV Determination of Biological Activity

A. TRAP Assay Protocol

The ability of a compound to increase telomerase activity in a cell can be determined using TRAP (Telomeric Repeat Amplification Protocol) assay, which is known in the art (e.g. Kim et al., U.S. Pat. No. 5,629,154; Harley et al., U.S. Pat. No. 5,891,639). As used herein, "telomerase activity as measured in a TRAP assay" refers to telomerase activity as measured in keratinocytes or fibroblasts according to the following protocol. The activity is typically compared to the activity similarly measured in a control assay of such cells (e.g., a telomerase activity 50% greater than observed in a solvent control).

Cell lines suitable for use in the assay, normal human peripheral blood mononuclear cells (PBMCs) or Human Epidermal Keratinocytes (neonatal) (HEKs), can be obtained from commercial sources, such as Cascade Biologics, Portland, Oreg. or 4C Biotech, Seneffe, Belgium, or from the ATCC (American Type Culture Collection). ATCC normal human fibroblast cell lines, which can be located on the ATCC web site, include for example, CCL135, CCL137, and CCL151.

For example, neonatal human epidermal keratinocytes (HEKs) are plated into a 96-well microtiter plate at approx. 5000 cells/well, in growth medium (e.g. Epi-Life Medium+ keratinocyte Growth Supplement supplied by Cascade Biologics, Inc.) and incubated for one day. Test compositions in a suitable solvent, such as 95% ethanol or DMSO, are added to selected wells in a range of concentrations and incubated for a further 24+/−1 hours.

Compounds to be tested are first formulated at a 10× desired final concentration in 10% DMSO. The formulated compound is added to the 96-well culture along with a control of DMSO to provide various concentrations of the compound. The final DMSO concentration may be 1% in all wells. For other cell types or in other situations, higher or lower concentrations of DMSO may be desired.

A cytotoxicity assay may be performed in parallel with the telomerase TRAP testing by preparing a duplicate cell culture plate treated with the same compounds and using a metabolism responsive dye such as Alamar Blue to assess the number of cells at the beginning and the end of the incubations with the test compounds.

If cytotoxicity of the test compounds is not objectively measured, the morphology of treated cells can first be observed under a microscope, to verify that there are no visual signs of irregular growth.

To conduct the TARP assay, media is removed from the wells, and the cells are rinsed twice in PBS (Ca and Mg free). The dishes are chilled on ice, and Nonidet P40 cell lysis buffer is added (approx. 100 μl per well) and triturated by pipetting up and down several times. The cells are the incubated on ice for 1 hour.

Alternatively, cells may be harvested at 24 hr+/−1 hr by removing the growth medium and washing once with PBS (phosphate buffered saline) removing as much medium as possible. The cells are then lysed by adding 50 μL of M-Per buffer (Pierce Cat#78503 & 78501) and incubating on ice for 1 hr+/−15 min. The plate is, optionally, centrifuged at 2000 RPM, 5 min. The lysate is carefully collected from each well of the plate and transferred to a fresh V-bottom storage 96-well plate, leaving the monolayer cells intact.

Alternatively, cell lysing solution may be prepared by addition of 3.0 mL Nonidet® P40, 1.0 mL CHAPS lysis buffer (see below), and 1.0 mL 10× TRAP buffer (see below) to 5.0 mL DNase-, RNase-free $H_2O$. (DNase-, RNase-free water may be generated by DEPC (diethylpyrocarbonate) treatment or purchased from vendors such as Sigma).

| CHAPS Lysis Buffer | | |
|---|---|---|
| Stock | For 1 mL | Final concn. |
| 1M Tris-HCl pH 7.5 | 10 μl | 10 mM |
| 1M $MgCl_2$ | 1 μl | 1 mM |
| 0.5M EGTA | 2 μl | 1 mM |
| 100 mM AEBSF | 1 μl | 0.1 mM |
| 10% CHAPS[a] | 50 μl | 0.5% |
| BSA | 1 mg | 1 mg/ml |
| 100% Glycerol | 100 μl | 10% |
| DNase-, RNase-free $H_2O$ | 936 μl (to 1 mL) | |

[a]The CHAPS detergent is added just before use of the lysis buffer. In addition, AEBSF (4-(2-aminoethyl)-benzenesulfonyl fluoride HCl) is added to the lysis buffer just prior to the extraction step.

The level of telomerase activity in the cell lysates is measured using a TRAP assay.

| 10X TRAP Buffer | |
|---|---|
| Stock | Final concn. |
| 1M Tris-HCl, pH 8.3 | 200 mM |
| 1M $MgCl_2$ | 15 mM |
| 1M KCl | 650 mM |
| Tween 20 (Boehringer Mannheim) | 0.5% |
| 0.1M EGTA | 10 mM |
| 20 mg/ml BSA | 1 mg/ml |

The following materials are combined to generate a master PCR Mix.

| Stock | Per Reaction (45 μl) | Final concn.[a] |
|---|---|---|
| 10X TRAP Buffer | 5.0 μL | 1X |
| 2.5 mM dNTPs | 1.0 μL | 50 μM |
| Cy5-TS Primer (0.5 mg/ml) | 0.1 μL | 1 ng/ml |
| ACX Primer (0.1 mg/ml) | 1.0 μL | 2 ng/ml |
| Taq Polymerase (5 U/μl) | 0.4 μL | 0.04 units/μl |
| Cell extract | 5-10 μL | |
| DNase-, RNase-free $H_2O$ | 32.5-37.5 μL (to 45 μL total) | |

[a]Based on final volume of 40 μl PCR mix plus 10 μl cell lysate = 50 μl.

The PCR mix includes the following components: Cy5-TS primer, a 5'-Cy5 labeled oligonucleotide having the sequence 5'-AAT CCG TCG AGC AGA GTT-3' (SEQ ID NO:1), is a telomerase substrate. Depending on the telomerase activity in the medium, telomere repeats (having the sequence (AGGGTT)$_n$ will be added to the substrate, to form telomerase extended products, also referred to as telomerase products. The ACX primer, having the sequence 5'-GCG CGG CTT ACC CTT ACC CTT ACC CTA ACC-3' (SEQ ID NO:2), is an anchored return primer that hybridizes to the telomerase extended products.

A sample of cell lysate (e.g., 5 μL) is added to the PCR mix in a reaction tube, and the telomere extension and PCR amplification is done in the bench top PCR machine at the following cycle profiles: 30° C. for 30 minutes, repeat 28 cycles of the following 3 step reaction: 94° C./30 sec, 60° C./30 sec, and 72° C./1 min, followed by 72° C./4 minutes and hold at 4° C.

Loading dye containing e.g. bromophenol blue and xylene cyanol is added, and the samples are subjected to 10-15% non-denaturing PAGE in 1×TBE, until the bromophenol blue runs off the gel. The TRAP reaction product is observed, e.g. by using a fluoroimager for detection of CY5-labeled telomerase products (maximal excitation at 650 nm; maximal emission at 670 nm).

Telomerase activity may be measured by captured total pixel vol. (DNA ladder bands) above background for each gel lane. The activity may be normalized by measuring the total RNA (ng/mL) by using Ribogreen® RNA Quantitation Kit from Molecular Probes, cat. # R-11490 and following commercially recommended conditions with an RNA standard range of 0.8-200 ng/mL, 1:200 dilution of RG dye, 100-250× dilution of sample.

Total Pixel Vol/RNA=Normalized Relative Telomerase Activity

Cells number (used to assess cytotoxicity) was directly proportional to the Alamar Blue reading Alternatively, a set of an internal standard and primer can be added for quantitation purposes. The TSU2 internal standard an oligonucleotide having the sequence 5'-AAT CCG TCG AGC AGA GTT AAA AGG CCG AGA AGC GAT-3'; SEQ ID NO:3), an extension of the TS primer sequence, is added in a small controlled quantity. The U2 primer, having the sequence 5'-ATC GCT TCT CGG CCT TTT (SEQ ID NO:4), is a return primer designed to hybridize to the 3' region of the internal standard.

The final amount of TSU2 internal standard after amplification is generally 5-10 pmol per 50 μl reaction mixture. This internal control gives a specific 36-mer PCR amplification product that appears as a distinct band on the gel below the first telomere addition product that appears as a distinct band on the gel below the first telomere addition product (that is, the product of one telomer addition to the TS oligonucleotide, followed by amplification with the ACX return primer). This internal control band can be used to normalize the PCR amplifications from different samples.

The relative number of telomerase product molecules (TM) generated in the assay is determined according to the formula below:

$$TM=(T_{TRAP\ Products}-T_{BKD1})/(T_{Int\ Std}-T_{BKD2})$$

where: $T_{TRAP\ Products}$ is the total intensity measured on the gel for all telomerase products, $T_{BKD1}$ is the background intensity measured in a blank lane for an area equivalent in size to that encompassed by the telomerase products, $T_{Int\ Std}$ is the intensity for the internal standard band, and $T_{BKD2}$ is the background intensity measured in a blank lane for an area equivalent in size to that encompassed by the internal standard band. The resulting number is the number of molecules of telomerase products generated for a given incubation time, which, for the purposes of determining TM, is designated herein as 30 minutes.

Compounds of formulas I as described above are able to produce, at a concentration of 1 μM or less, a level of telomerase activity in fibroblasts or keratinocytes at least 50% greater than seen in a solvent control. Even more potent activities may be appropriate for some applications, such as compounds that produce telomerase activities at least about 75%, 100% or 500% greater than the level of such activity seen in a solvent control, as measured in the described TRAP assay, at a concentration of 10 μM or less.

Effectiveness in increasing telomerase activity was evaluated for compounds of formula I above in various concentrations. Assays were carried out in HEKneoP cells (neonatal keratinocytes), according to the protocol described above. Concentrations typically ranged from approx. 0.001 μM to 10 μM in DMSO.

The ability of the compounds to increase the activity of telomerase as shown in Table 2.

B. Wound Healing Assay Protocol

The compounds of formula I can be used to promote healing of wounds, burns, abrasions or other acute or chronic conditions of the epidermis, as discussed further below. As used herein, "wound healing activity as measured in a scratch assay" refers to the activity as measured in keratinocytes or fibroblasts according to the following protocol, and expressed as the value of WH shown in the formula below.

Cells are plated in flasks (5×10$^5$ cells per flask) and cultured for two days in a humidified chamber at 5% $CO_2$, 37° C. To create the "wound", a 2 ml plastic pipette is gently dragged to "scratch" the cell surface. The ideal wound is approximately 2-3 mm wide and 50 mm long (along the long axis of the tissue culture flask). The cells are retreated with medium containing either vehicle (DMSO; control sample) or test compositions at multiple concentrations. A wound area is identified, the flask marked, and the appearance of the cells documented photographically over 3-4 days continued culturing of the cells.

Amount of wound closure is determined by measuring the width of the wound over time for compound-treated samples relative to vehicle-treated or other control cells. Measurements are made from the photographs taken for each of the samples on days 1 (immediately after scratching), 2, 3, and 4. Percentage of wound healing (also expressed as "wound healing activity") is calculated by the following formula:

$$WH=100-[100 \times W_n/W_0],$$

where $W_n$ is the width of the wound on day n and $W_0$ is the width of the wound on day one (i.e. immediately after scratching).

V. Therapeutic Indications and Treatment Methods

The present invention provides methods for increasing telomerase activity in a cell, by contacting a cell or tissue with a formulation of an isolated compound of formula I as disclosed in Section II above, in an amount effective to increase telomerase activity in the cell. The method may include the preliminary step of identifying a cell or tissue in which an increase telomerase activity is desired. The cell may be in culture, i.e. in vitro or ex vivo, or within a subject or patient in vivo.

Benefits to be realized from an increase in telomerase activity in a cell or tissue include, for example, enhancement of the replicative capacity and/or life span of the contacted cells and improved functional capacity of the cells (i.e. improved expression of the normal differentiated functions of the cells). The method may further comprise diagnosing a condition in a subject or patient wherein an increase in telomerase activity in cells or tissue of the patient is desired; e.g., diagnosing a disease subject to treatment by an increase in telomerase activity in cells or tissue. Accordingly, the invention provides methods of treating a condition in a patient, by increasing telomerase activity in cells or tissue of said patient, the method comprising administering to a subject in need of such treatment an effective amount of a compound of formula I as disclosed in Section II above. An "effective amount" refers to an amount effective to increase telomerase activity in the cells or tissue of the patient, such that a therapeutic result is achieved.

Such conditions or diseases for treatment or prevention may include, for example, conditions associated with cellular senescence or with an increased rate of proliferation of a cell in the absence of telomerase, which leads to accelerated telomere repeat loss. By "increased rate of proliferation" is meant a higher rate of cell division compared to normal cells of that cell type, or compared to normal cells within other individuals of that cell type. The senescence of those groups of cells at an abnormally early age can eventually lead to disease (see West et al., U.S. Pat. No. 6,007,989).

Various disease states exist in which an increase in telomerase activity in certain cell types can be beneficial. Accordingly, the invention provides methods of treating in a patient a condition or disease selected from the following, by increasing telomerase activity in the cells of the patient, comprising administering to a subject in need of such treatment, an effective amount of a compound of formula I as described above. In some cases, the condition may also be subjected to treatment by ex vivo cell therapy, as described further below, employing the associated cell types (indicated in parenthesis).

(a) Alzheimer's disease, Parkinson's disease, Huntington's disease, and stroke (cells of the central nervous system, including neurons, glial cells, e.g. astrocytes, endothelial cells, fibroblasts).

(b) age-related diseases of the skin, such as dermal atrophy and thinning, elastolysis and skin wrinkling, sebaceous gland hyperplasia or hypoplasia, senile lentigo and other pigmentation abnormalities, graying of hair and hair loss or thinning, or chronic skin ulcers (fibroblasts, sebaceous gland cells, melanocytes, keratinocytes, Langerhan's cells, microvascular endothelial cells, hair follicle cells), (c) degenerative joint disease (cells of the articular cartilage, such as chrondrocytes and lacunal and synovial fibroblasts), (d) osteoporosis and other degenerative conditions of the skeletal system (cells of the skeletal system, such as osteoblasts, bone marrow stromal or mesenchymal cells, osteoprogenitor cells), (e) age- and stress-related diseases of the vascular system including atherosclerosis, calcification, thrombosis, and aneurysms (cells of the heart and vascular system, including endothelial cells, smooth muscle cells, and adventitial fibroblasts), (f) age-related macular degeneration (cells of the eye, such as pigmented epithelium and vascular endothelial cells), (g) AIDS (HIV-restricted $CD8^+$ cells);

(h) age- and stress-related immune system impairment, including impairment of tissue turnover, which occurs with natural aging, cancer, cancer therapy, acute or chronic infections, or with genetic disorders causing accelerated cell turnover, and related anemias and other degenerative conditions (other cells of the immune system, including cells in the lymphoid, myeloid, and erythroid lineages, such as B and T lymphocytes, monocytes, circulating and specialized tissue macrophages, neutrophils, eosinophils, basophils, NK cells, and their respective progenitors); and (i) pulmonary fibrosis or liver cirrhosis or liver fibrosis;

(j) chronic inflammatory gastrointestinal diseases such as Barretts esophagus; and (k), bone marrow failure syndrome, aplastic anemia, myelodysplastic anemia or myelodysplastic syndrome.

In addition to the cell types noted above, further cell types in which an increase in telomerase activity can be therapeutically beneficial include, but are not limited to, cells of the liver, endocrine and exocrine glands, smooth musculature, or skeletal musculature.

As an example, in the case of HIV-infected individuals, $CD8^+$ cell turnover is increased as these cells attempt to control the level of HIV-infected $CD4^+$ cells. In AIDS (item (g) above), disease is believed to be caused by the early senescence of HIV-restricted $CD8^+$ cells. The aging of such cells is attributed not simply to abnormal amount of loss of telomere sequences per cell doubling, but, in addition, to the increased replicative rate of the cells, such that telomere attrition is greater than normal for that group of cells. The invention thus provides methods of treating an HIV infected subject, and more particularly of reducing early senseence of HIV-restricted $CD8^+$ cells in an HIV infected subject, by administering to a subject in need of such treatment an effective amount of a compound of formula I as disclosed in Section II above.

An increase in telomerase activity can benefit non-dividing cells as well as proliferating cells, e.g. in conditions associated with increased susceptibility to cell death due to stress, such as ischemia in heart failure or in stroke (see e.g. Oh and Schneider, *JMol Cell Cardiol* 34(7):717-24; Mattson, *Exp Gerontol.* 35(r):489-502). The invention thus provides methods of reducing stress- or DNA-damage-induced cell death in a subject, such as a subject experiencing ischemic conditions in tissue due to heart failure. or stroke, by increasing telomerase activity in cells of the subject, comprising administering to a subject in need of such treatment an effective amount of a compound of formula I as disclosed in Section II above. As noted above, the method may include the preliminary step of diagnosing in the subject the indicated condition.

In another aspect, the compositions may be used for the treatment of individuals in which one or more cell types are limiting in that patient, and whose life can be extended by extending the ability of those cells to continue replication or resist stress-induced cell death. One example of such a group of cells is lymphocytes present in Down's Syndrome patients. The invention thus provides a method of enhancing replicative capacity and/or life span of lymphocytes present in Down's Syndrome patient, by increasing telomerase activity in said cells of the patient, comprising administering to such a patient an effective amount of a compound of formula I as disclosed in Section II above. The compositions may also be used to improve resistance to stress-induced cell death occurring during normal aging.

In a further aspect of the invention, increasing telomerase activity is effective to prevent pulmonary fibrosis or to promote healing of pulmonary fibrosis. It has been determined that short telomeres are a signature of idiopathic pulmonary fibrosis and of cryptogenic liver cirrhosis (Alder et al., PNAS (2008) 105(35) 13051-13056). The present compounds may be used to treat pulmonary fibrosis or liver cirrhosis.

In a further aspect, the invention provides a method of enhancing transplantation of a tissue from a living donor or cadaver to a living patient or subject comprising contacting the transplantation tissue with an isolated compound of formula I as defined above. In a further aspect, the invention provides a method of enhancing transplantation of a tissue to a living patient or subject comprising administering the isolated compound of formula I as defined above to the patient either before, simultaneous with, or for a period of time after the transplantation of the tissue into the patient. The transplanted tissue may be solid tissue, such as a kidney, heart, lungs etc., or hematopoietic tissue such as, without limitation, blood cells such as leukocytes, lymphocytes or hematopoietic precursor cells which may be derived from bone marrow.

In a further aspect of the invention, increasing telomerase activity is effective to promote healing of wounds, burns, abrasions or other acute or chronic conditions of the epidermis. The invention thus provides a method of treating an acute or chronic condition of the epidermis, by administering to a patient in need of such treatment, topically to the affected area, an effective amount of a formulation of an isolated compound of formula I as disclosed in Section II above.

As used herein, an "acute or chronic condition of the epidermis" includes acute conditions such as lesions suffered in trauma, burns, abrasions, surgical incisions, donor graft sites, and lesions caused by infections agents, and chronic conditions such as chronic venous ulcer, diabetic ulcer, compression ulcer, pressure sores, and ulcers or sores of the mucosal surface. Also included are skin or epithelial surface lesions caused by a persistent inflammatory condition or infection, or by a genetic defect (such as keloid formation and coagulation abnormalities). See, for example, PCT Pubn. No. WO 02/91999.

Desirable effects of an increase in telomerase activity in such treatment include cell proliferation or migration at the treatment site, epithelialization of the surface, closure of a wound if present, or restoration of normal physiological function. By "epithelialization" or "reepithelialization" of a treatment site is meant an increase in density of epithelial cells at the site as a result of the applied therapy.

The method may also be used to enhance growth of engrafted cells. Desirable effects of an increase in telomerase activity in such treatment include coverage of the treatment site, survival of engrafted cells, lack of immune rejection, closure of a wound if present, or restoration of normal physiological function. Engrafted cells may participate in wound closure either by participating directly in the healing process (for example, becoming part of the healed tissue), or by covering the wound and thereby providing an environment that promotes healing by host cells.

The invention also contemplates manipulation of the skin and repair of any perceived defects in the skin surface.

In a further aspect, the methods and compositions of the invention can be used to enhance replicative capacity and/or extend life span of cells in culture, e.g. in ex vivo or in vitro cell therapy or in monoclonal antibody production, by increasing telomerase activity in the cells. Increasing telomerase activity increases the replicative capacity of such cells by slowing telomere repeat loss and/or improving resistance to stress-induced cell death during cell proliferation.

In the case of ex vivo application, an effective amount of a compound of formula I as described above is added to explant cells obtained from a subject. An "effective amount" refers to an amount effective to increase telomerase activity in the cells, thereby increasing the replicative capacity and/or life span of the cells.

The explant cells may include, for example, stem cells, such as bone marrow stem cells (U.S. Pat. No. 6,007,989), bone marrow stromal cells (Simonsen et al., *Nat Biotechnol* 20(6):592-6, 2002), or adrenocortical cells (Thomas et al, *Nat Biotechnol* 18(1):39-42, 2000). Disease conditions such as those noted in items (a)-(g) above may also be subject to ex vivo cell-based therapy. Examples include the use of muscle satellite cells for treatment of muscular dystrophy, osteoblasts to treat osteoporosis, retinal pigmented epithelial cells for age-related macular-degeneration, chondrocytes for osteoarthritis, and so on.

For example, the recognition that functional $CD8^+$ cells are limiting in AIDS patients to control the expansion of infected CD4+ cells allows a therapeutic protocol to be devised in which HIV-restricted $CD8^+$ cells are removed from an HIV-infected individual at an early stage, when AIDS is first detected, stored in a bank, and then reintroduced into the individual at a later stage, when that individual no longer has the required $CD8^+$ cells available. Thus, an individual's life can be extended by a protocol involving continued administration of that individual's limiting cells at appropriate time points. These appropriate points can be determined by following $CD8^+$ cell senescence, or by determining the length of telomeres within such $CD8^+$ cells, as an indication of when those cells will become senescent. In accordance with the invention, the stored cells can be expanded in number in the presence of an agent which slows telomere repeat loss, i.e. compound of formula I as disclosed in Section II above.

Accordingly, the invention provides methods of ex vivo cell based therapy, which include obtaining a cell population from a subject, and expanding the cell population ex vivo, wherein the cell population is treated with a compound of formula I as disclosed in Section II above, in an amount effective to increase telomerase activity and thereby enhance the replicative capacity and/or life span of the cell population. The method generally includes diagnosing in a subject a condition subject to a treatment by ex vivo cell based therapy, such as those noted above.

In a further embodiment, the invention provides a method of stem cell proliferation, wherein a stem cell population is treated with a compound of formula I as disclosed in Section II above, in an amount effective to increase telomerase activity and thereby enhance the replicative capacity and/or life span of the cell population.

VI. Formulations and Methods of Administration

The invention encompasses methods of preparing pharmaceutical compositions useful for increasing telomerase activity in a cell and/or promoting wound healing. Accordingly, an isolated compound of formula I as described in Section II is combined with a pharmaceutical excipient, and optionally with other medicinal agents, adjuvants, and the like, which may include active and inactive ingredients. The compositions may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, or the like. The formulations may be provided in unit dosage forms suitable for simple administration of precise dosages.

An isolated compound of formula I may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, polyethylene glycol, macrogol-15 hydroxystearate or for example water or normal saline. If desired, the composition may also contain minor amounts of non-toxic auxiliary substances such as wetting agents, emulsiyfing agents, or buffers.

For use in wound healing or treatment of other acute or chronic conditions of the epidermis, a compound of formula I is formulated for topical administration. The vehicle for topical application may be in one of various forms, e.g. a lotion, cream, gel, ointment, stick, spray, or paste. These product forms can be formulated according to well known methods. They may comprise various types of carriers, including, but not limited to, solutions, aerosols, emulsions, gels, and liposomes. The carrier may be formulated, for example, as an emulsion, having an oil-in-water or water-in-oil base. Suitable hydrophobic (oily) components employed in emulsions include, for example, vegetable oils, animal fats and oils, synthetic hydrocarbons, and esters and alcohols thereof, including polyesters, as well as organopolysiloxane oils. Such emulsions also include an emulsifier and/or surfactant, e.g. a nonionic surfactant, such as well known in the art, to disperse and suspend the discontinuous phase within the continuous phase.

The topical formulation typically contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components as known in the art, e.g. astringents, fragrances, pigments, skin penetration enhancing agents, sunscreens, etc.

The pharmaceutical compositions may also be formulated for administration parenterally, transdermally, or by inhalation. An injectable composition for parenteral administration typically contains the active compound in a suitable IV solution, such as sterile physiological saline. The composition may also be formulated as a suspension in a lipid or phospholipid, in a liposomal suspension, or in an aqueous emulsion.

For administration by inhalation, the active compound is formulated as solid or liquid aerosol particles. The formulation may also include a propellant and/or a dispersant, such as lactose, to facilitate aerosol formation. For transdermal administration, the active compound is included in a transdermal patch, which allows for slow delivery of a compound to a selected skin region, and which may also include permeation enhancing substances, such as aliphatic alcohols or glycerol.

Methods for preparing such formulations are known or will be apparent to those skilled in the art; for example, see *Remington's Pharmaceutical Sciences* (19th Ed., Williams & Wilkins, 1995). The composition to be administered will contain a quantity of the selected compound in a pharmaceutically safe and effective amount for increasing telomerase activity in the target cells or tissue.

The pharmaceutical composition contains at least 0.1% (w/v) of a compound of formula I as described above, greater than 0.1%, up to about 10%, up to about 5%, and up to about 1% (w/v). Choice of a suitable concentration depends on factors such as the desired dose, frequency and method of delivery of the active agent.

For treatment of a subject or patient, such as a mammal or a human patient, dosages are determined based on factors such as the weight and overall health of the subject, the condition treated, severity of symptoms, etc. Dosages and concentrations are determined to produce the desired benefit while avoiding any undesirable side effects. Typical dosages of the subject compounds are in the range of 1-50 mg/kg/day, 1-25 mg/kg/day, 1-20 mg/kg/day, 4-15 mg/kg/day. Typical dosages of the subject compounds are in the range of about 1 to 1,500 mg/day for a human patient, about 1-500 mg/day. In specific embodiments, for example, the compound designated herein as 4 is administered at a level of at least 1 mg/kg/day or at least 5 mg/kg/day.

Administration of the compounds of Formula I may be every other day, on a daily basis, twice daily or more often. Administration may be once, for 1-20 days, for 5-10 days or continuously for as long as necessary to prevent or treat the disease or condition being prevented or treated.

The following examples are offered by way of illustration and not by way of limitation.

EXAMPLES

Example 1

Conversion of Astragaloside IV (1) to 17-[5-(1-Hydroxy-1-methyl-ethyl)-2-methyl-tetrahydro-furan-2-yl]-4,4,13,14-tetramethyl-tetradecahydro-cyclopropa[9,10]cyclopenta[a]phenanthrene-3β,6α,16β-triol [cycloastragenol] (2)

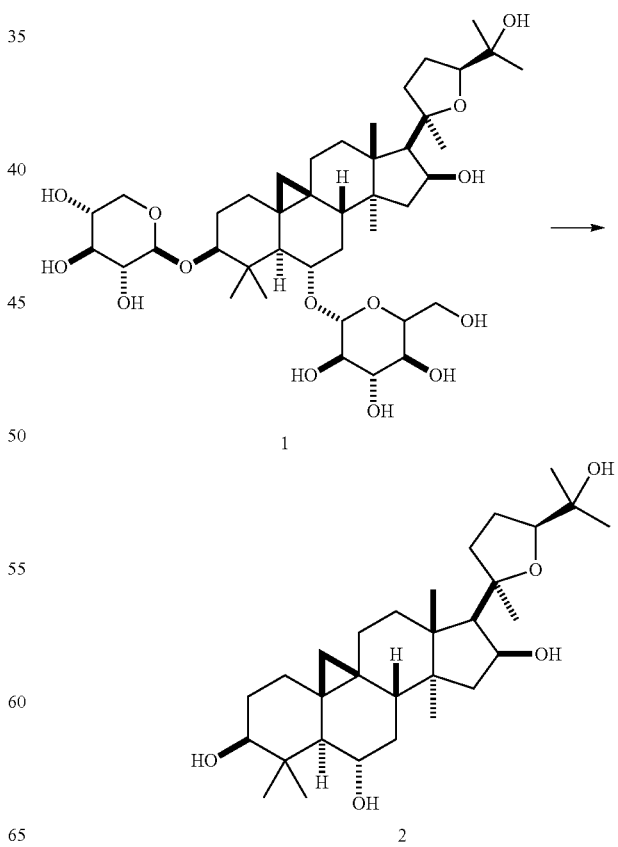

To astragaloside IV (1) (5.00 g, mmol) was added "HCl-MeOH 10" (TCI America) (500 mL) and the mixture was stirred at room temperature for 7 days. The reaction mixture was concentrated to about half volume under reduced pressure at 20° C. (do not heat). The mixture was partitioned into aqueous sodium bicarbonate and ethyl acetate. The aqueous layer was extracted with ethyl acetate again. The organic layers were combined, washed with saturated sodium chloride, dried on anhydrous sodium sulfate, and concentrated under reduced pressure. The residue was purified by column chromatography (20:1~14:1 chloroform/methanol). In order to replace the residual solvent with ethanol, the purified material was dissolved in ethanol and the solvent was removed under reduced pressure to afford 2 (2.1 g, 64%).

$^1$H NMR (CDCl$_3$) δ(ppm) 0.34 (d, J=4.7 Hz, 1H), 0.48 (d, J=4.3 Hz, 1H), 0.92 (s, 3H), 0.93 (s, 3H), 1.0-1.8 (m, 13H), 1.11 (s, 3H), 1.19 (s, 3H), 1.22 (s, 6H), 1.27 (s, 3H), 1.9-2.0 (m, 4H), 2.30 (d, J=7.8 Hz, 1H), 2.54 (q, J=11.8 Hz, 1H), 3.27 (m, 1H), 3.50 (m, 1H), 3.72 (t, J=7.4 Hz, 1H), 4.65 (q, J=7.4 Hz, 1H). ESI-MS m/z Positive 491 (M+H)$^+$, Negative 549 (M+AcO)$^-$. TLC (Merck, Kieselgel 60) Rf=0.33 (6:1 chloroform/methanol)

Example 2

Preparation of 2-(L)-Amino-3-methyl-butyric acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester, hydrochloride salt [C3-(L)-valyl-cycloastragenol](4)

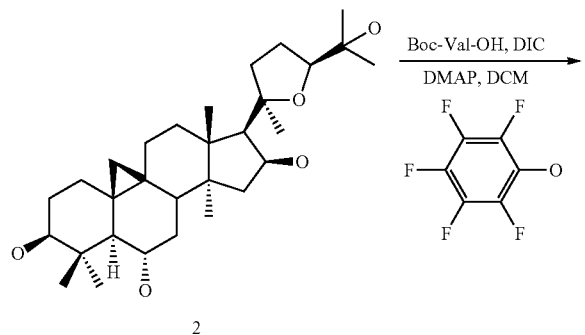

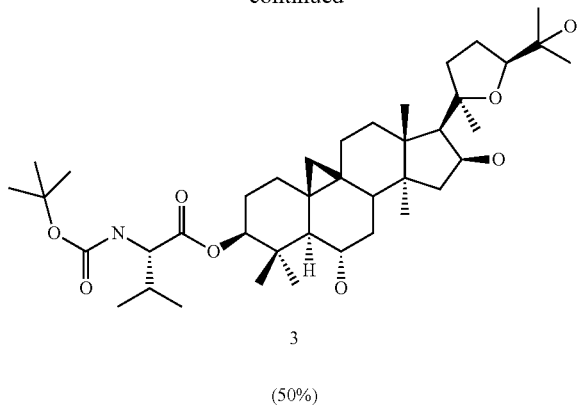

3

(50%)

Preparation of 3: Boc-L-Valine-OH (18 g, 81.63 mmols) (Bachem, Torrance, Calif.) was dissolved in 150 ml of dichloromethane (DCM). To this was added 15 g (81.63 mmol) of pentafluorophenol. The reaction was cooled in an ice-bath followed by slow addition of 12.8 ml (81.63 mmols) of 1,3-diisopropylcarbodiimide (DIC). After complete addition the reaction mixture was stirred at room temperature for 30 minutes at which time the reaction mixture turned turbid (diisopropylcabodimide-urea precipitation). To this mixture was then added 10 g (20.41 mmols) of (2) followed by 10 g (81.63 mmol) of dimethylaminopyridine (DMAP) and the reaction was stirred at room temperature for 24 hours. The reaction mixture was transferred into a sepratory funnel and washed with H$_2$O (2×) 1% aq. HCl (2×), 0.1 N aq. NaOH (2×), sat. NaHCO$_3$ (3×), H$_2$O (1×) and brine (1×), the organic layer was separated, dried over Na$_2$SO$_4$, filtered and the solvent was evaporated under vacuum. The residue was purified using flash chromatography with solvent gradient of 2%-5% MeOH in DCM to furnish 7.0 g (50%) of the target product 3 together with 6.0 g, (33%) of this bis product.

$^1$HNMR for 3: (CDCl$_3$) δ(ppm) 0.38 (1H, bs), 0.90-1.38 (m, 30H), 1.39-1.45(s,m 12H), 1.59-1.63 (m, 5H), 1.76-1.82 (m, 2H), 1.96-2.01(m, 4H), 2.16-2.20 (m, 1H), 2.30-2.35 (d, 1H), 2.49-2.54 (q, 1H), 3.45-3.57 (t, 1H), 3.71-3.76(t, 1H), 4.19-4.21(m, 1H), 4.53-4.61(m, 1H), 4.69-4.71(q, 1H), 5.0-5.2(d, 1H. MS (M+H) 690.

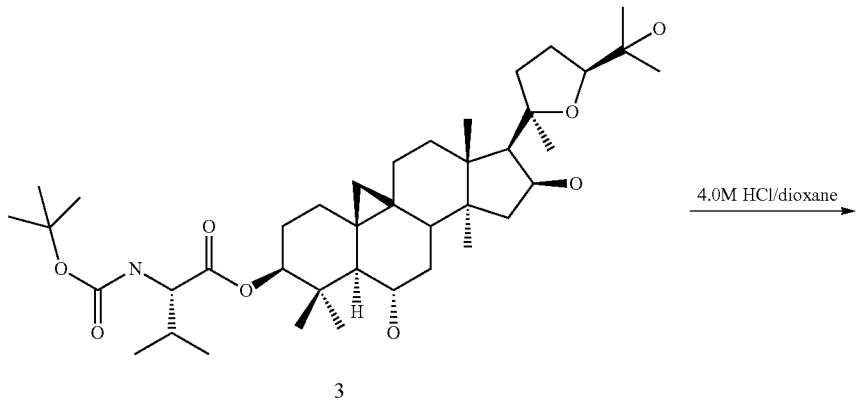

3

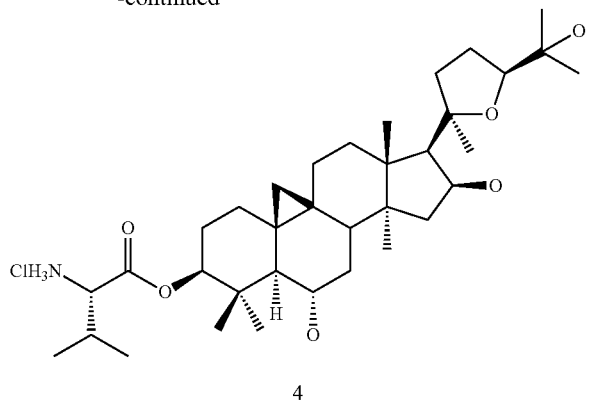

4

Preparation of 4: to 1 g (1.45 mmol) of 3 was added 1.8 ml of 4.0 M HCl/dioxane and stirred for 4 hrs. The solvents were evaporated and the product was precipitated in 10 ml of cold diethyl ether and the solids were filtered. The solids were then dried under high vacuum for overnight to yield 800 mg (88%) of the target product 4 (2-(L)-Amino-3-methyl-butyric acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester, hydrochloride salt as a white powder.

$^1$HNMR for 4 (DMSOd$_6$) δ(ppm): 0.36 (bs, 1H), 0.49 (bs, 1H), 0.80-1.39 (m, 29H), 1.44-1.60(m, 3H), 1.61-1.70 (m, 2H), 1.81-1.89 (m, 4H), 1.81-1.89 (m, 4H), 2.19-2.30(m, 2H), 2.41-2.60 (m, 2H), 3.29-3.41 (m, 2H), 3.58-3.61(t, 1H), 3.81-3.83(m, 1H), 4.18-4.39 (bs, 4H), 4.49-4.51 (q, 2H), 4.54-4.59 (m, 1H), 8.40-8.58(bs, 2H), MS (M+H) 590.

Example 3

Preparation of 2-(D)-Amino-3-methyl-butyric acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester, hydrochloride salt hydrochloride salt [C3-(D)-valyl-cycloastragenol](5)

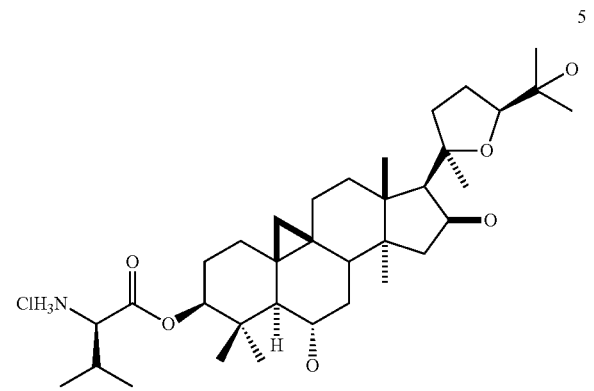

5

Using the procedure of Example 2 with Boc-(D) Valine-OH (Bachem, Torrance, Calif.) 18 g, 18.63 mmols) compound 5 was prepared.

$^1$HNMR for 5 (DMSOd$_6$) δppm: 0.30 (bs, 1H), 0.50 (bs, 1H), 0.80-1.39 (m, 29H), 1.46-1.58(m, 3H), 1.61-1.70 (m, 2H), 1.79-1.89(m, 4H), 2.16-2.32(m, 2H), 2.38-2.54 (m, 2H), 3.29-3.41(m, 2H), 3.58-3.61(t, 1H), 3.81-3.83(m, 1H), 4.13-4.24 (bs, 4H), 4.50-4.52(q, 2H), 4.54-4.59(m, 1H), 8.43-8.60 (bs, 2H). MS (M+H) 590.

Example 4

Preparation of 2-(L)-Amino-3-methyl-butyric acid 6α-(2-amino-3-methyl-butyryloxy)-16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester, hydrochloride salt [C3,C6-(L,L)-bisvalyl-cycloastragenol]-7

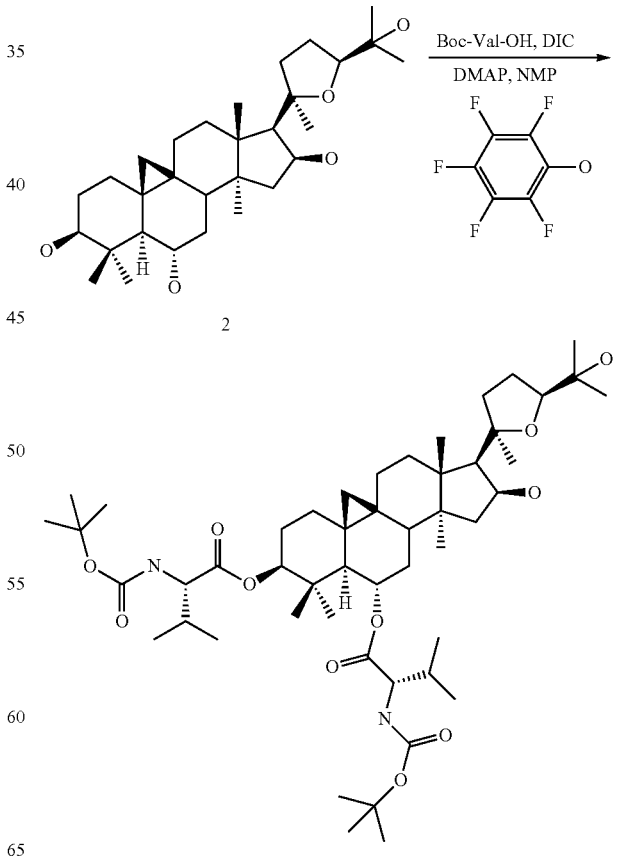

2

6

Preparation of 6: Boc-(L) Valine-OH (10 g, 46.08 mmols) was dissolved in 80 ml of N-methylpyrrolidone (NMP). To this was added 8.5 g (46.08 mmol) of pentafluorophenol. The reaction was cooled in an ice-bath followed by slow addition of 7.2 ml (46.08 mmols) of DIC. After complete addition the reaction mixture was stirred at room temperature for 30 minutes at which time the reaction mixture turned turbid (diisopropylcarbodimide-urea precipitation). To this mixture was then added 3.2 g (6.60 mmols) of 2 followed by 5.5 g (45 mmol) of DMAP and the reaction was stirred at room temperature for 24 hours. The reaction mixture was transferred into a sepratory funnel and washed successively with $H_2O$ (6×), 1% aq. HCl (2×), 0.1 N aq. NaOH (2×), sat. $NaHCO_3$ (3×), $H_2O$ (1×), and brine (1×), the organic layer was separated, dried over $Na_2SO_4$, filtered and the solvent was evaporated under vacuum. The residue was purified using flash chromatography with solvent gradient of 2%-5% MeOH in DCM to furnish 4.8 g (83%) of the traget product 6.

$^1$HNMR for 6: ($CDCl_3$) δppm: 0.38 (1H, bs), 0.60 (1H, bs), 0.80-1.0 (m, 24H), 1.15 (s,s, 6H), 120 (s,s 6H), 1.31 (s, 6H), 1.35 (s,s, 4H) 1.41 (s,s, 18H), 1.56-1.60(m, 4H), 1.79-1.83 (m, 3H), 3.71-3.76 (t, 1H), 4.08-4.21 (m, 2H), 4.58-4.60(m, 1H), 4.61-4.70(q, 1H), 4.72-4.80 (m, 1H), 4.82-4.84 (d, 1H), 4.9-5.0 (d, 1H). MS (M+H) 889.

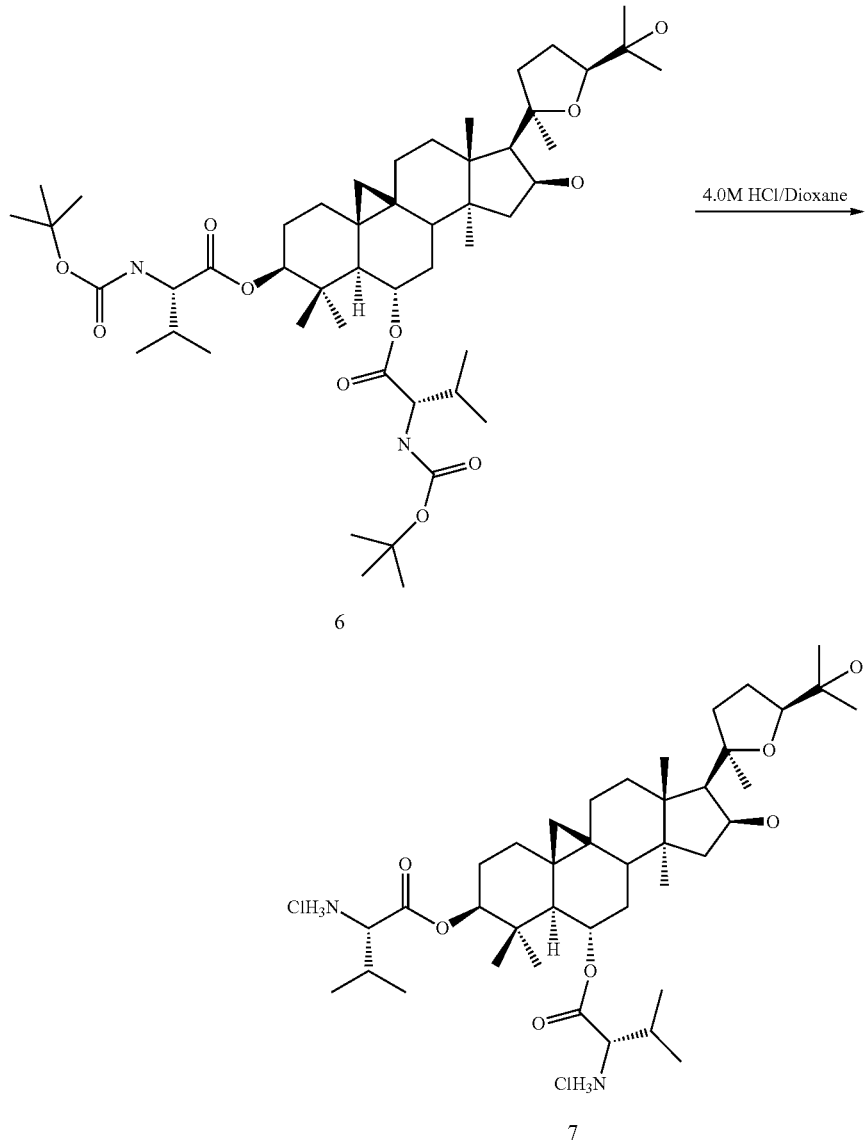

Preparation of 7: To a 4.5 g (5.06 mmol) of the 6 was added 13 ml of 4.0M HCl/dioxane and stirred for 4 hrs. The solvents were evaporated and the product was precipitated with 40 ml of cold diethyl ether and the solids filtered off. The solids were then dried under high vacuum for overnight to yield 3.1 g (91%) of the target product 7 as a white powder.

$^1$HNMR for 7 ($DMSOd_6$) δppm: 0.24 (bs, 1H), 0.80-1.20 (m, 35H), 1.41-1.85 (m, 12H), 2.10-2.22 (m, 2H), 2.32-2.42 (m, 4H), 2.19-2.30(m, 2H), 3.59-3.62(m, 1H), 3.81-3.83(m, 2H), 4.40-4.53 (m, 1H), 4.60-4.71 (m, 1H), 4.81-4.9 (m, 1H), 8.40-8.70(d, 4H). MS (M+H) 689.

Example 5

Preparation of 2-(D)-Amino-3-methyl-butyric acid 6α-(2-amino-3-methyl-butyryloxy)-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester, hydrochloride salt [C3,C6-(D,D)-bisvalyl-cycloastragenol]8

Using the same procedure of Example 4 and Boc-(D) Valine-OH (Bachem, Torrance, Calif.), compound 8 was prepared.

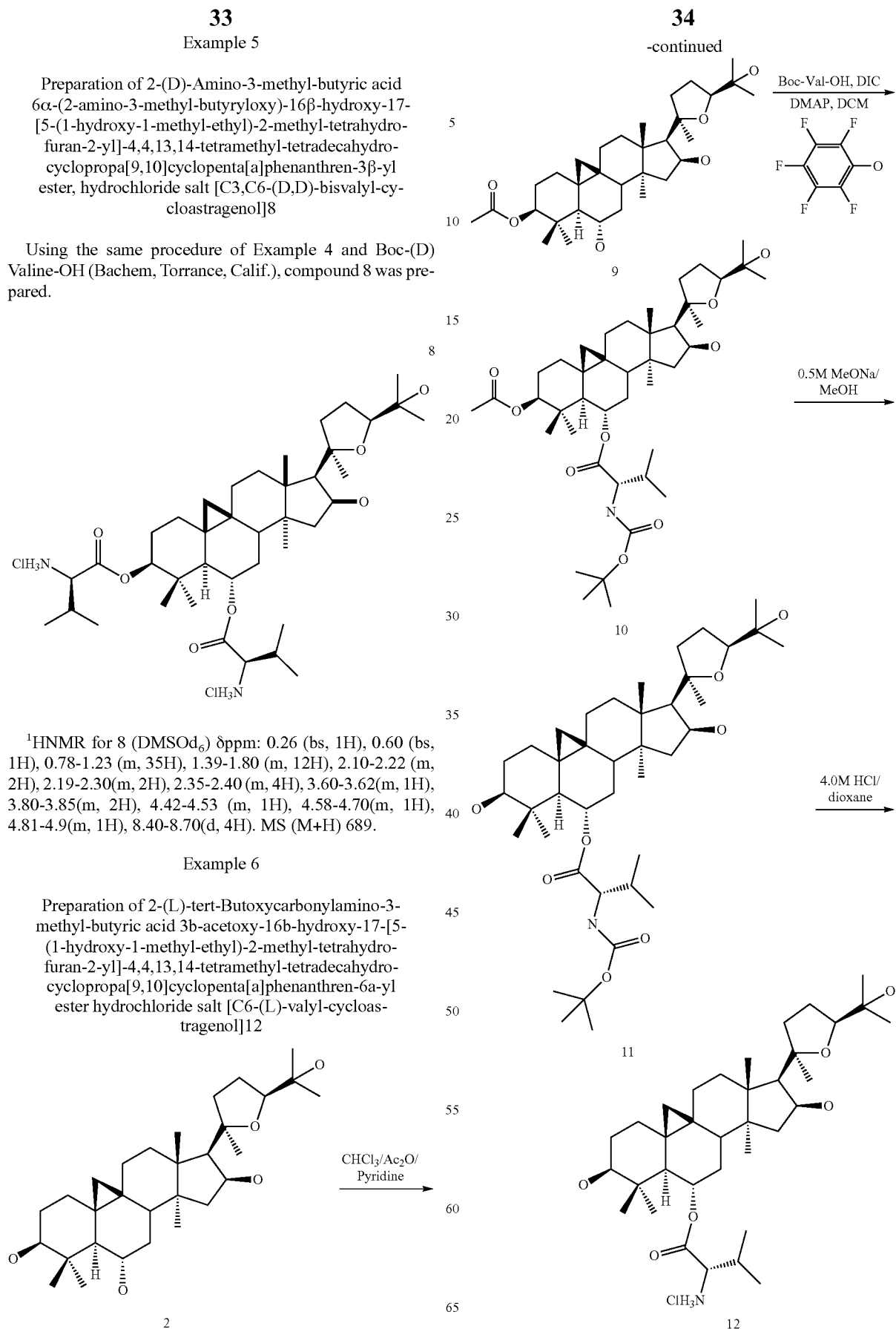

$^1$HNMR for 8 (DMSOd$_6$) δppm: 0.26 (bs, 1H), 0.60 (bs, 1H), 0.78-1.23 (m, 35H), 1.39-1.80 (m, 12H), 2.10-2.22 (m, 2H), 2.19-2.30(m, 2H), 2.35-2.40 (m, 4H), 3.60-3.62(m, 1H), 3.80-3.85(m, 2H), 4.42-4.53 (m, 1H), 4.58-4.70(m, 1H), 4.81-4.9(m, 1H), 8.40-8.70(d, 4H). MS (M+H) 689.

Example 6

Preparation of 2-(L)-tert-Butoxycarbonylamino-3-methyl-butyric acid 3b-acetoxy-16b-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-6a-yl ester hydrochloride salt [C6-(L)-valyl-cycloastragenol]12

Preparation of 9: To a 5 g (10.22 mmol) of 2 was added 40 ml of CHCl₃ and 2.1 ml (26 mmol) of pyridine. The reaction mixture was cooled in an ice-bath and to this was slowly added 2.5 ml (26 mmol) of acetic anhydride. After complete addition the reaction was stirred at 4° C. for 24 hrs. The TLC showed three spots corresponding to 9, monoacetylated and bis acetylated products. The reaction mixture was diluted with 100 ml of DCM and washed successively with the following: sat. aq. NaHCO₃, (2×), 1M HCl (1×), H₂O (1×) and brine (1×). The organic layer was separated, dried over Na₂SO₄, filtered and evaporated under vacuum. The crude was purified by flash chromatography with 2% MeOH in DCM to furnish 2.3 g (42%) of 9 as white solids.

¹HNMR for 9: (CDCl₃) δppm: 0.38 (1H, bs), 0.90-1.25 (m, 32H), 1.39-1.45(m, 2H), 1.50-1.60 (m, 2H), 1.70-1.82(m, 2H), 1.96-2.01 (m, 4H), 2.18-2.20 (m, 3H), 2.30-2.35 (d, 1H), 3.45-3.57 (m, 1H), 3.71-3.76(m, 1H), 4.49-4.59(m, 1H), 4.69-4.72(m, 1H). MS (M+H) 533.

Preparation of 10: 1.08 g (5.0 mmol) of Boc-(L)-Valine was dissolved in 5 ml of DCM. To this was added 920 mg (5.0 mmols) of pentafluorophenol. The reaction was cooled in an ice-bath followed by slow addition of 0.78 ml (5.0 mmols) of DIC. After complete addition the reaction mixture was stirred at room temperature for 30 minutes. To this mixture was then added 532 mg (1.0 mmol) of 9 followed by 490 mg (4.0 mmol) of DMAP and the reaction was stirred at room temperature for 24 hours. The reaction mixture was transferred into a sepratory funnel and washed with sat. NaHCO₃ (3×), 0.1N HCl (1×), H₂O (3×), and brine (1×), the organic layer was separated, dried over Na₂SO₄, filtered and the solvent was evaporated under vacuum. 20 ml of Et₂O was added to the residue and the white precipitate was filtered under suction. This operation was repeated once more and the filtrate was evaporated and the residue was purified using flash chromatography with solvent gradient of 2%-5% MeOH in DCM to furnish 590 mg (81%) of 10.

¹HNMR for 3: (CDCl₃) δppm: 0.35 (1H, bs), 0.53 (1H, bs), 0.75-1.30 (m, 38H), 1.45(s, 9H), 1.50-1.60 (m, 2H), 1.70-1.82(m, 2H), 1.96-2.01(m, 4H), 2.18-2.20 (s, 3H), 2.30-2.35 (d, 1H), 3.71-3.76(m, 1H), 4.13-4.19 (m, 1H), 4.40-4.41 (m, 1H), 4.51-4.53 (m, 1H), 4.60-4.63 (m, 1H), 4.69-4.72(m, 1H), 4.81-4.83(m, 1H). MS (M+H) 731.

Preparation of 11: 500 mg (0.68 mmols) of 10 was dissolved in 5.0 ml of dry MeOH and 2.8 ml of 0.5 M MeONa/MeOH was added to it. The reaction was stirred at room temperature for 24 hrs. The reaction was carefully neutralized (monitoring with pH meter) by dropwise addition of 1M HCl/MeOH and the solvents were evaporated under vacuum. The residue was dissolved in 30 ml of DCM and successively washed with sat. NaHCO₃ (1×), H₂O (1×), and brine (1×), dried over Na₂SO₄, filtered and the solvents were evaporated under vacuum. The crude product was purified using flash chromatography to furnish 403 mg (86%) of 11 as white solids. The crude was carried over to the next step without any purification.

¹HNMR for 11: (CDCl₃) δppm: 0.39 (1H, bs), 0.58 (1H, bs), 0.86-1.35 (m, 38H), 1.47(s, 9H), 1.53-1.61 (m, 2H), 1.70-1.82(m, 2H), 1.96-2.01(m, 4H), 2.30-2.35 (d, 1H), 3.19-3.22 (m, 1H), 3.71-3.76(m, 1H), 4.13-4.19 (m, 1H), 4.40-4.41 (m, 1H), 4.60-4.63 (m, 1H), 4.69-4.72(m, 1H), 4.81-4.83 (m, 1H). MS (M+H) 690.

Preparation of 12: To 400 mg (0.58 mmol) of 10 was added 0.73 ml of 4.0M HCl/dioxane and stirred for 4 hrs. The solvents were then evaporated under vacuum and the residue was washed with 5 mL of cold diethyl ether. The solids were filtered off and dried at high vacuum for overnight to furnish 290 mg (80%) of 12 as white solids.

¹HNMR for 12 (DMSOd₆) δppm: 0.30 (bs, 1H), 0.45 (bs, 1H), 0.80-1.19 (m, 29H), 1.47-1.58(m, 3H), 1.61-1.70 (m, 2H), 1.81-1.89(m, 4H), 2.19-2.30(m, 2H), 2.43-2.60 (m, 2H), 3.03-3.05 (m, 1H), 3.56-3.60 (t, 1H), 3.73-3.75 (m, 1H), 3.80-4.09 (bs, 4H), 4.40-4.51 (m, 1H), 4.71-4.79(m, 1H), 8.40-8.58(bs, 2H). MS (M+H) 590.

Example 7

Preparation of 2-(L),3-Dimethyl-pentanoic acid 6α,16β-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester Hydrochloride salt [C3-(L)-isoleucyl-cycloastragenol]14

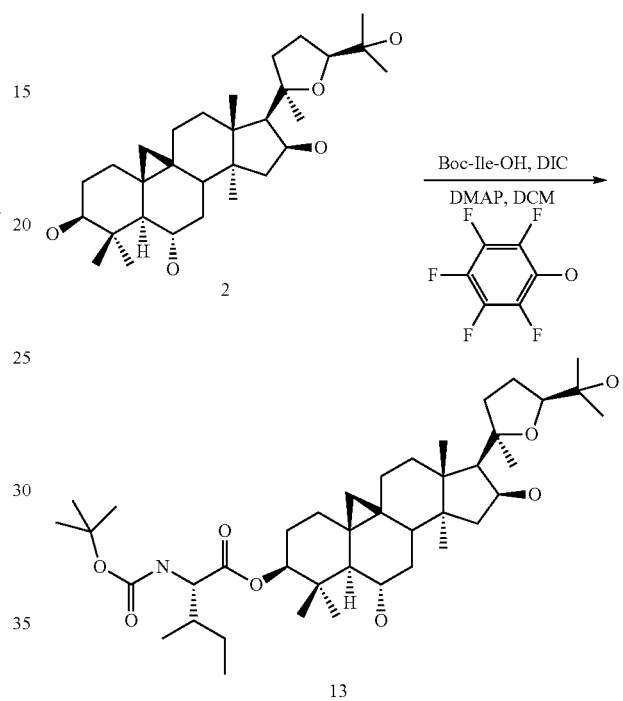

Preparation of 13: Boc-(L) Isoleucine-OH (Bachem, Torrance, Calif.) (1.9 g. 8.16 mmols) was dissolved in 25 ml of DCM. To this was added 1.5 g (8.16 mmol) of pentafluorophenol. The reaction was cooled in an ice-bath followed by slow addition of 1.3 ml (8.16 mmols) of DIC. After complete addition the reaction mixture was stirred at room temperature for 30 minutes at which time the reaction mixture turned turbid (diisopropylcarbodimide-urea precipitation). To this mixture was then added 1.0 g (2.04 mmols) of 2 followed by 976 mg (7.0 mmol) of DMAP and the reaction was stirred at room temperature for 24 hours. The reaction mixture was transferred into a sepratory funnel and washed with H₂O (2×) 1% aq. HCl (2×), 0.1N aq. NaOH (2×), sat. NaHCO₃ (3×), H₂O (1×) and brine (1×), the organic layer was separated, dried over Na₂SO₄, filtered and the solvent was evaporated under vacuum. The residue was purified using flash chromatography with solvent gradient of 2%-5% MeOH in DCM to furnish 943 mg (67%) of the target product 13 together with 330 mg of the bis product.

¹HNMR for 13: (CDCl₃) δppm: 0.38 (1H, bs), 0.52 (1H, bs), 0.93-1.28 (m, 33H), 1.39-1.45(s,m, 12H), 1.59-1.63 (m, 5H), 1.76-1.82(m, 2H), 1.96-2.01(m, 4H), 2.16-2.20 (m, 1H), 2.30-2.35 (d, 1H), 2.49-2.54 (q, 1H), 3.45-3.57 (m, 1H), 3.71-3.76(t, 1H), 4.19-4.21(dd, 1H), 4.53-4.61(m, 1H), 4.69-4.71(q, 1H), 5.0-5.2(d, 1H. MS (M+H) 704.

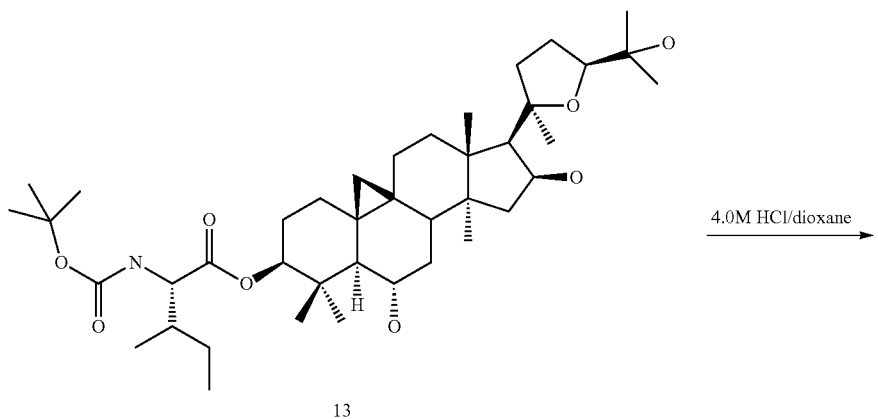

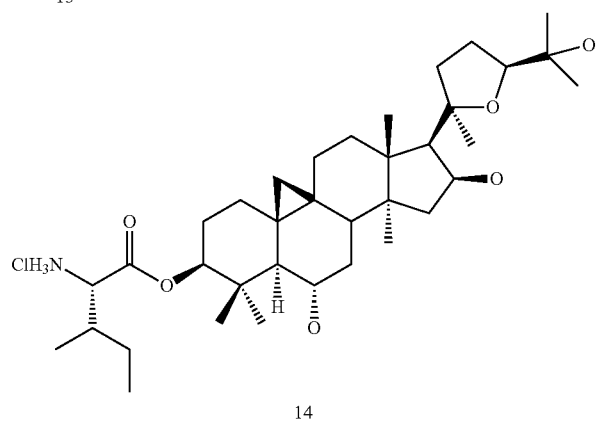

Preparation of 14: To a 700 mg (1.0 mmol) of the 11 was added 1.25 ml of 4.0M HCl/dioxane and stirred for 4 hrs. The solvents were evaporated and the product was precipitated in 10 ml of cold diethyl ether and the solids were filtered. The solids were then dried under high vacuum for overnight to yield 512 mg (80%) of the target product 12 as a white powder.

$^1$HNMR for 12 (DMSOd$_6$) δppm: 0.36 (bs, 1H), 0.49 (bs, 1H), 0.80-1.39 (m, 32H), 1.44-1.60(m, 3H), 1.61-1.70 (m, 2H), 1.81-1.89(m, 4H), 2.19-2.30(m, 2H), 2.41-2.60 (m, 2H), 3.29-3.41 (m, 1H), 3.58-3.61 (t, 1H), 3.86-3.90(m, 1H), 4.18-4.39 (bs, 4H), 4.51-4.53(m, 2H), 4.54-4.59(m, 1H), 8.40-8.58 (bs, 2H). MS (M+H) 604.

Example 8

Preparation of a Mixture 2-(L)-Amino-hexanoic acid 6a,16b-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3b-yl ester, hydrochloride salt [C3-(L)-ornithinyl-cycloastragenol]16a; 2-(L),5-Diamino-pentanoic acid 3b,16b-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-6a-yl ester, hydrochloride salt [C6-(L)-ornithinyl-cycloastragenol]16b and 2-(L),5-Diamino-pentanoic acid 3b,6a-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-16b-yl ester, hydrochloride salt [C16-(L)-ornithinyl-cycloastragenol]16c

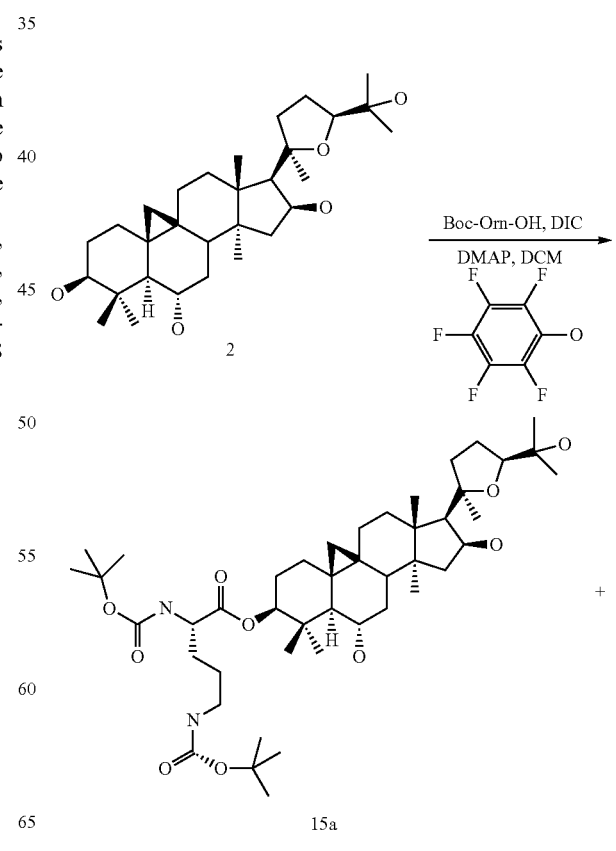

-continued

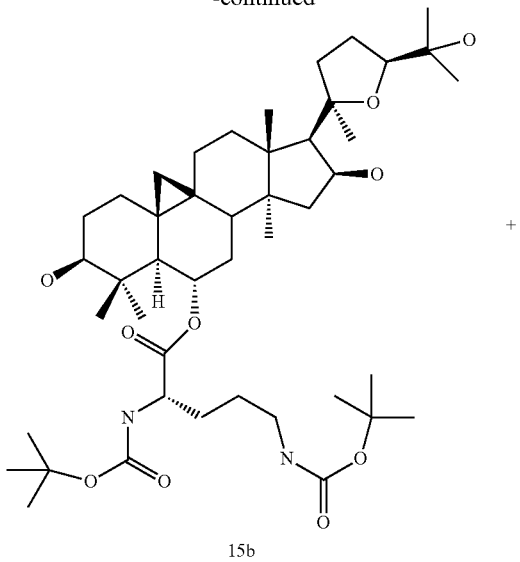

15b

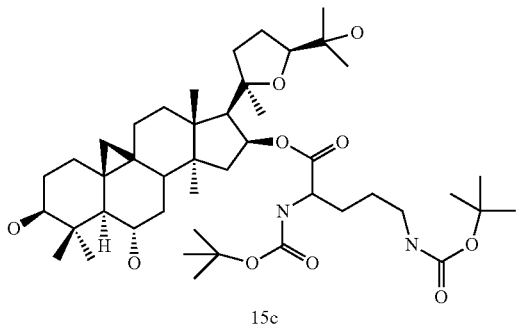

15c

Preparation of 15a, 15b, 15c: (Boc)$_2$-(L)-Ornithine-OH (4.5 g, 13.6 mmols) (Bachem, Torrance, Calif.) was dissolved in 15 ml of DCM. To this was added 2.5 g (13.6 mmol) of pentafluorophenol. The reaction was cooled in an ice-bath followed by slow addition of 2.2 ml (13.6 mmols) of DIC. After complete addition the reaction mixture was stirred at room temperature for 30 minutes at which time the reaction mixture turned turbid (diisopropylcarbodimide-urea precipitation). To this mixture was then added 700 mg (1.43 mmols) of 2 followed by 1.6 g (13.6 mmol) of DMAP and the reaction was stirred at room temperature for 24 hours. The reaction mixture was transferred into a separatory funnel and washed with H$_2$O (2×) 1% aq. HCl (2×), 0.1N aq. NaOH (2×), sat. NaHCO$_3$ (3×), H$_2$O (1×) and brine (1×), the organic layer was separated, dried over Na$_2$SO$_4$, filtered and the solvent was evaporated under vacuum. To the residue was then added 25 ml of diethylether and the urea was precipitated out. The filtrate was evaporated and the residue was purified using flash chromatography with solvent gradient of 2%-5% MeOH in DCM to furnish 690 mg (60%) of a mixture of products 15a, 15b, 15c, and 120 mg (8%) of the C3, C6 bis product.

The $^1$HNMR showed major amounts of 15a and 15b products with 2% of the regioisomer 15c.

$^1$HNMR of the mixture (15a, 15b and 15c): (CDCl$_3$) δppm: 0.38 (1H, bs), 0.52 (1H, bs), 0.90-1.38 (m, 26H), 1.39-1.45 (s,m, 27H), 1.59-1.63 (m, 5H), 1.76-1.82(m, 2H), 1.96-2.01 (m, 4H), 2.16-2.20 (m, 1H), 2.30-2.35 (d, 1H), 2.49-2.54 (q, 1H), 3.10-3.19 (m, 6H), 3.19-3.22 (m, 1H), 3.45-3.57 (t, 1H), 3.71-3.76(m, 1H), 4.19-4.21(m, 1H), 4.22-4.30 (m, 1H), 4.52-4.60(m, 1H), 4.61-4.65(m, 1H), 4.79-4.81 (m, 1H), 4.95-5.01(m, 1H), 5.13-5.21(m, 1H), 5.38-5.41 (m, 1H). MS (M+H) 804

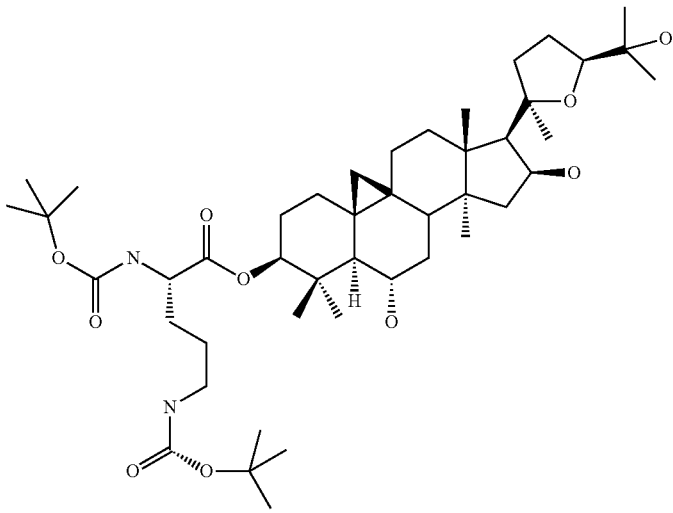

15a

-continued
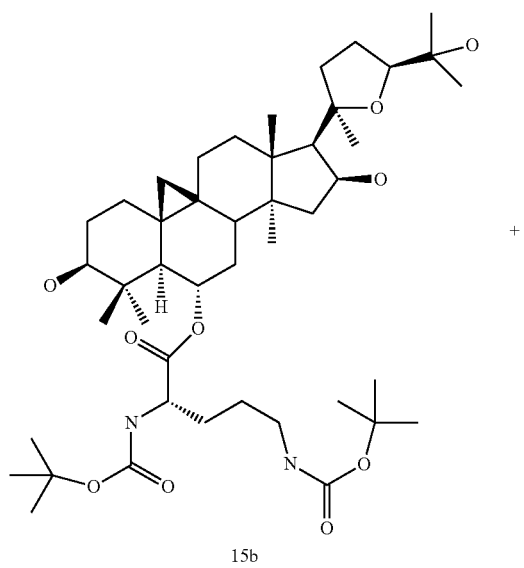
15b
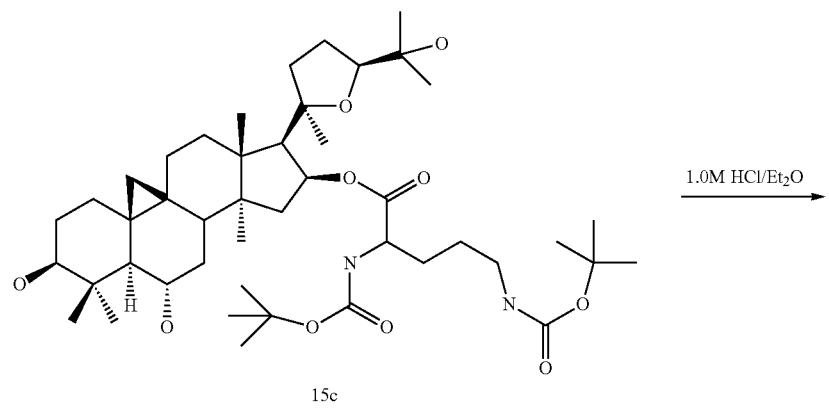
15c
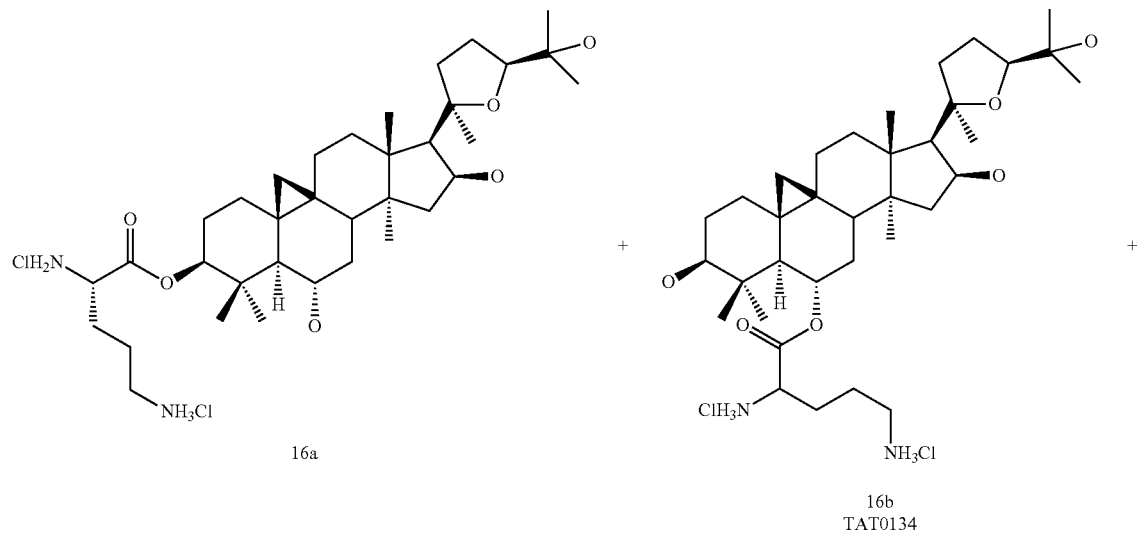
16a
16b
TAT0134

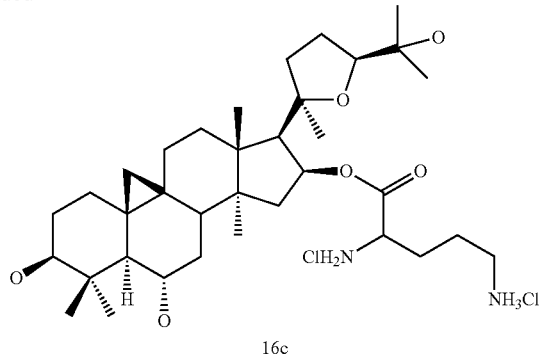

16c

Preparation of 16a, 16b, 16c To a 200 mg (0.25 mmol) of the mixture of 15a, 15b, 15c, was added 10 ml of 1.0M HCl/diethylether and stirred for 16 hrs. The white solids were filtered and washed with 10 ml of Et$_2$O (4×). The solids were then dried under high vacuum for overnight to yield 160 mg (95%) of the target products 16a, 16b, 16c, as a white powder. The $^1$HNMR showed major amounts of 16a and 16b products with 2% of the C-16 (16c) regioisomer.

The $^1$HNMR of the mixture (16a, 16b and 16c): (D$_2$O) δppm: 0.26 (1H, bs), 0.52 (1H, bs), 0.90-1.18 (m, 26H), 1.49-1.74 (m, 5H), 1.83-2.10(m, 2H), 2.20-2.31 (m, 4H), 2.81-2.92 (m, 2H), 3.19-3.20 (m, 1H), 3.39-3.42 (m, 1H), 3.62-3.71 (m, 1H), 3.88-4.00(m, 1H), 4.08-4.12 (m, 1H), 4.52-4.57(m, 1H), 4.61-4.65(m, 1H), 4.79-4.81 (m, 1H). MS (M+H): 605.

Example 9

Preparation of a mixture of 2-(L)-Amino-pentanedioic acid 1-{6a,16b-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3b-yl} ester Hydrochloride salt [C3(L0)-valyl-cycloastragenol] 18a; 2-(L)-Amino-pentanedioic acid 1-{3b,16b-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-6a-yl}ester. Hydrochloride salt[C6-(L)-glutamate-cycloastragenol]18b 2-(L)-Amino-pentanedioic acid 1-{3b,6a-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-16b-yl} ester. Hydrochloride salt [C16-(L)-glutamate-cycloastragenol](18c)

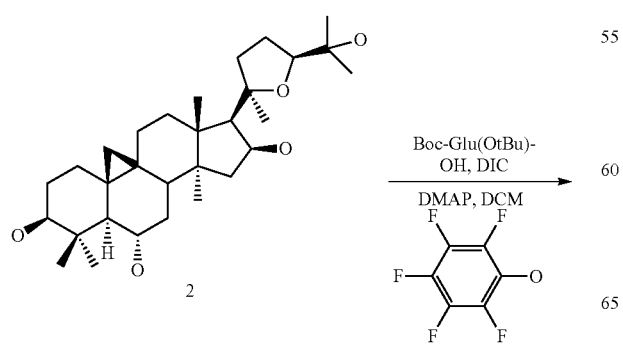

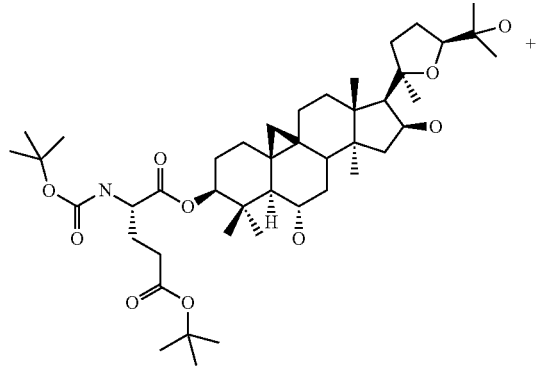

17a

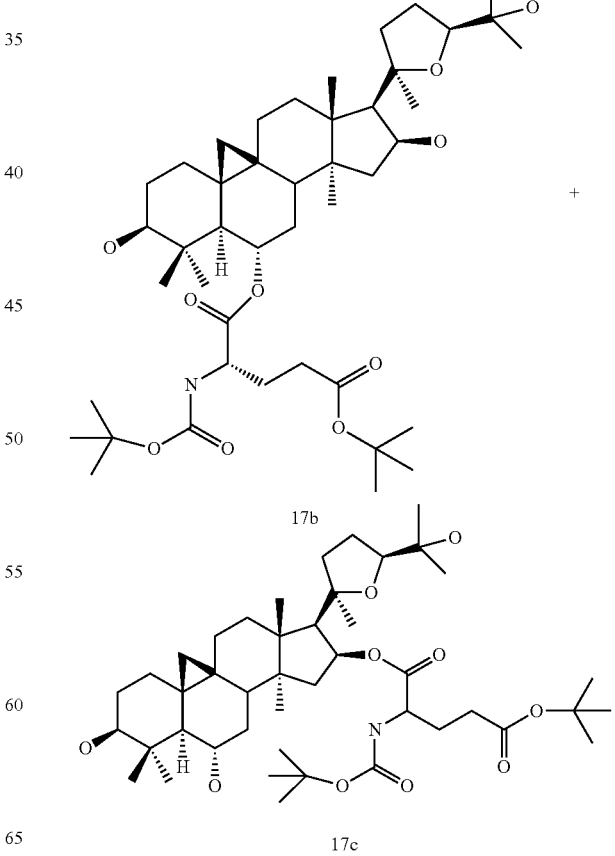

Preparation of 17a, 17b, 17c: Boc-(L)-Glutamic acid (Bachem, Torrance, Calif.) (O-tBu)-OH (4.5 g, 14.82 mmols) was dissolved in 15 ml of DCM. To this was added 2.73 g (14.82 mmol) of pentafluorophenol. The reaction was cooled in an ice-bath followed by slow addition of 2.3 ml (14.82 mmols) of DIC. After complete addition the reaction mixture was stirred at room temperature for 30 minutes at which time the reaction mixture turned turbid (diisopropylcarbodimide-urea precipitation). To this mixture was then added 765 mg (1.56 mmols) of cycloastragenol 2 followed by 1.8 g (14.82 mmol) of DMAP and the reaction was stirred at room temperature for 24 hours. The reaction mixture was transferred into a sepratory funnel and washed with $H_2O$ (2×) 1% aq. HCl (2×), 0.1N aq. NaOH (2×), sat. $NaHCO_3$ (3×), $H_2O$ (1×) and brine (1×), the organic layer was separated, dried over $Na_2SO_4$, filtered and the solvent was evaporated under vacuum. To the residue was then added 50 ml of diethylether and the urea was precipitated out. To filterate was evaporated and the residue was purified using flash chromatography with solvent gradient of 2%-5% MeOH in DCM to furnish 714 mg of (60%) of in-separable mixture of products 17a, 17b, 17c, and 140 mg, (9%) of the bis product (C3, C6). The $^1$HNMR showed major amounts of 17a and 17b products with 2% of the regioisomer (17c).

$^1$HNMR of the mixture (17a, 17b and 17c): $(CDCl_3)$ δppm: 0.29 (1H, bs), 0.56 (1H, bs), 0.90-1.20 (m, 26H), 1.30-1.40 (s,m, 25H), 1.48-1.65 (m, 3H), 1.82-1.92 (m, 2H), 2.16-2.22 (m, 2H), 2.42-2.50 (m, 2H), 3.20-3.40 (m, 1H), 3.55-3.61 (m, 1H), 3.82-3.96(m, 1H), 4.42-4.50 (m, 1H), 4.62-4.71 (m, 1H), 4.79-4.81 (m, 1H), 4.95-5.01(m, 1H), 5.13-5.21(m, 1H), 5.38-5.41 (m, 1H). MS (M+H) 776.

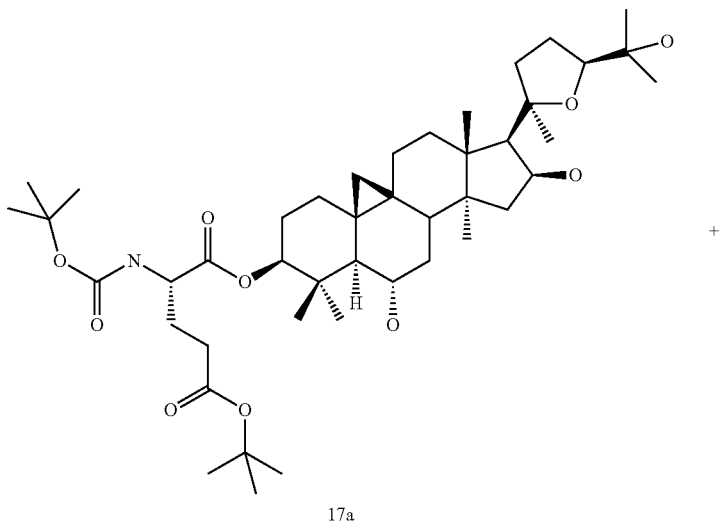

17a

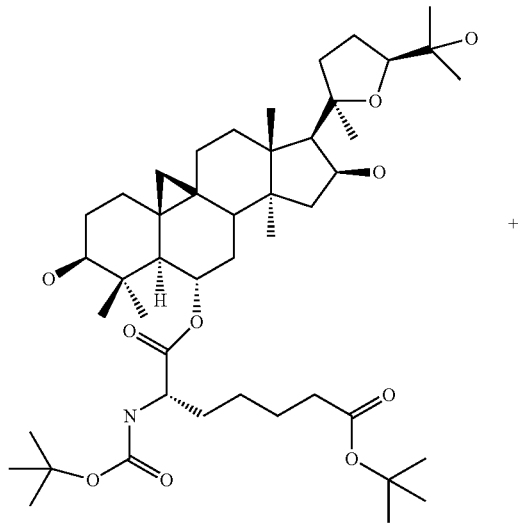

17b

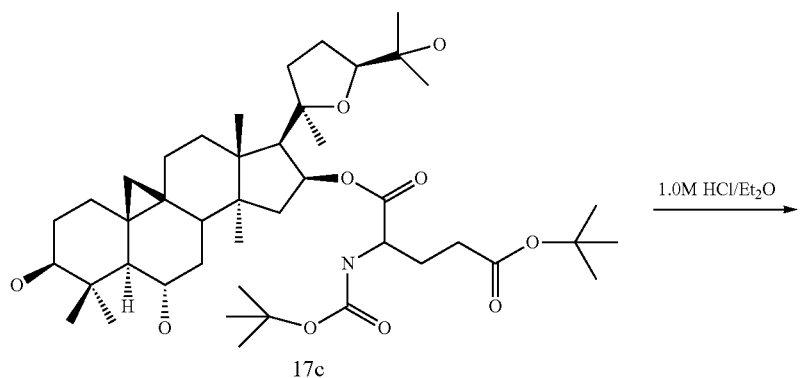

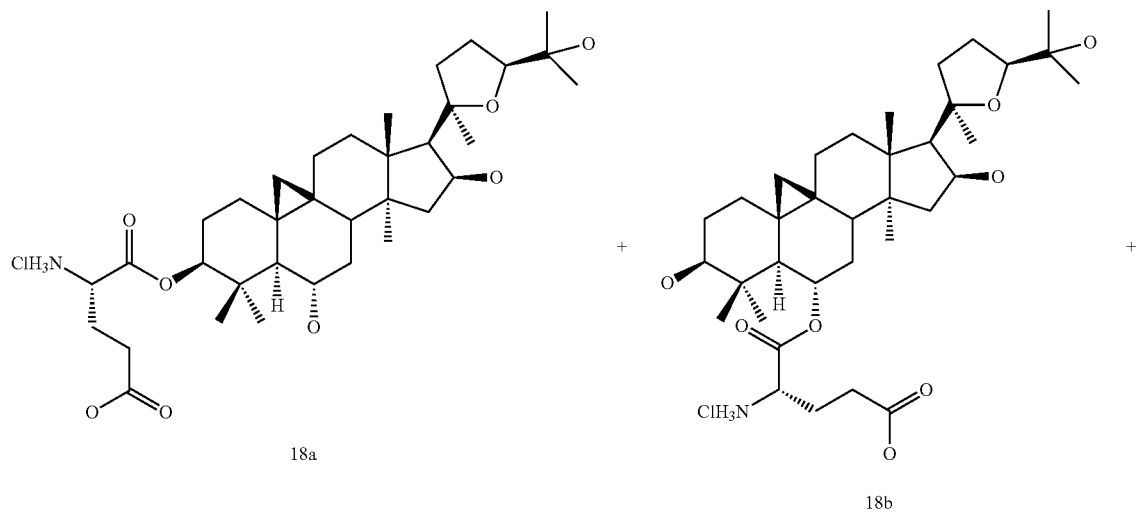

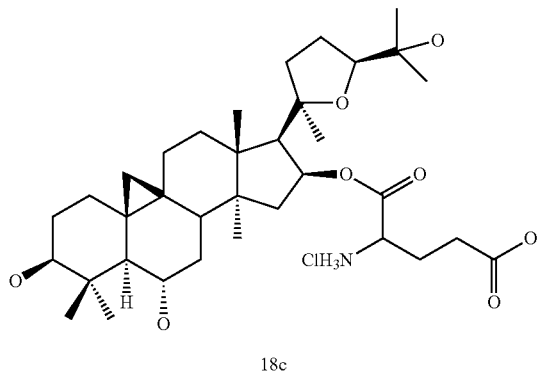

Preparation of 18a, 18b, 18c: To a 260 mg (0.34 mmol of the mixture of 17a, 17b and 17c was added 10 ml of 1.0M HCl/diethylether and stirred for 16 hrs. The white solids were filtered and washed with 10 ml of Et$_2$O (4×). The solids were then dried under high vacuum for overnight to yield 210 mg (95%) of the target products 18 as a white powder. The $^1$HNMR showed major amounts of C-3 (18a) and C-6 (18b) products with less than 2% of the C-16 (18c) regioisomer.

$^1$HNMR of the mixture (18a, 18b and 18c): (D$_2$O) δppm: 0.26 (1H, bs), 0.49 (1H, bs), 0.90-1.18 (m, 26H), 1.49-1.74 (m, 4H), 1.83-2.10(m, 2H), 2.20-2.31(m, 4H), 2.39-2.50 (m, 4), 2.81-292 (m, 2H), 3.29-3.30 (m, 1H), 3.39-3.42 (m, 1H), 3.62-3.71 (m, 1H), 3.88-4.02(m, 3H), 4.52-4.57 (m, 1H), 4.61-4.65(m, 1H), 4.79-4.81 (m, 1H). MS (M+H): 620.

Example 10

Preparation of 2-(L)-Amino-3-phenyl-propionic acid 6a,16b-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3a-yl ester. Hydrochloride salt [C3-(L)-phenylalanyl-cycloastragenol]20a; 2-(L)-Amino-3-phenyl-propionic acid 3,16b-dihydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-6a-yl ester. Hydrochloride salt [C6-(L)-phenylalanyl-cycloastragenol]20b

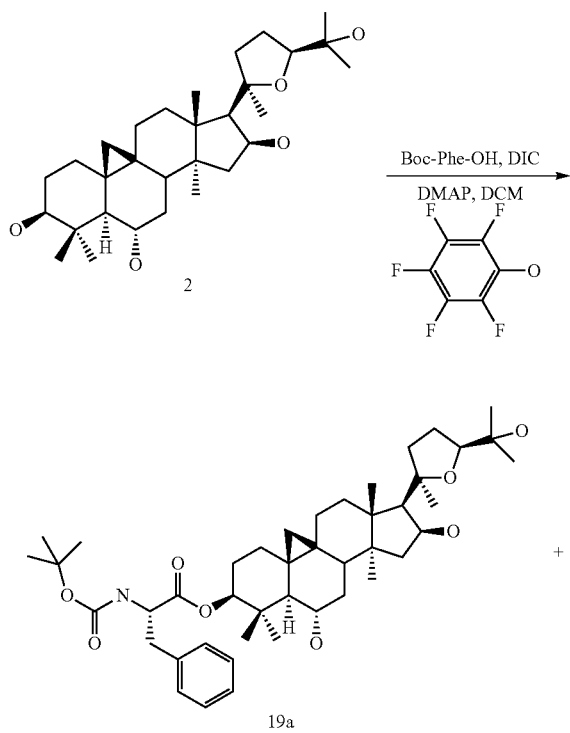

Preparation of 19a, 19b: Boc-(L)-Phenylalanine-OH (Bachem, Torrance, Calif.) (5.0 g, 18.84 mmols) was dissolved in 30 ml of DCM. To this was added 3.5 g (18.84 mmol) of pentafluorophenol. The reaction was cooled in an ice-bath followed by slow addition of 2.9 ml (1.9 mmols) of DIC. After complete addition the reaction mixture was stirred at room temperature for 30 minutes at which time the reaction mixture turned turbid (diisopropylcarbodiimide-urea precipitation). To this mixture was then added 1.0 g (1.56 mmols) of cycloastragenol 2 followed by 1.8 g (15 mmol) of DMAP and the reaction was stirred at room temperature for 24 hours. The reaction mixture was transferred into a sepratory funnel and washed with $H_2O$ (2×) 1% aq. HCl (2×), 0.1N aq. NaOH (2×), sat. $NaHCO_3$ (3×), $H_2O$ (1×) and brine (1×), the organic layer was separated, dried over $Na_2SO_4$, filtered and the solvent was evaporated under vacuum. To the residue was then added 50 ml of diethylether and the urea was precipitated out. The filterate was evaporated and the residue was purified using flash chromatography with solvent gradient of 1%-2% MeOH in DCM to furnish 950 mg of (68%) of in-separable mixture (C-3 and C-6) of products and 290 mg (30%) of the bis product (C3 and C6). The $^1$HNMR showed major amounts of C-3 (19a) and C-6 product (19b).

$^1$HNMR of the mixture (19a and 19b): ($CDCl_3$) δppm: 0.32 (1H, bs), 0.60 (1H, bs), 0.70-1.20 (m, 14H), 1.30-1.40(s,m 12H), 1.48-1.65 (m, 2H), 1.76-1.92(m, 4H), 2.22-2.32 (m, 1H), 2.52-2.58 (m, 1H), 2.86-2.91(m, 1H), 3.0-3.18(m, 1H), 3.20-3.24 (m, 1H), 3.55-3.61 (m, 1H), 3.72-3.80(m, 1H), 4.0-4.10 (m, 1H), 4.42-4.58 (m, 2H), 4.61-4.63 (m, 1H), 4.77-4.78 (m, 1H), 4.81-4.90 (m, 1H), 7.08-7.25 (m, 5H). MS (M+H) 738.

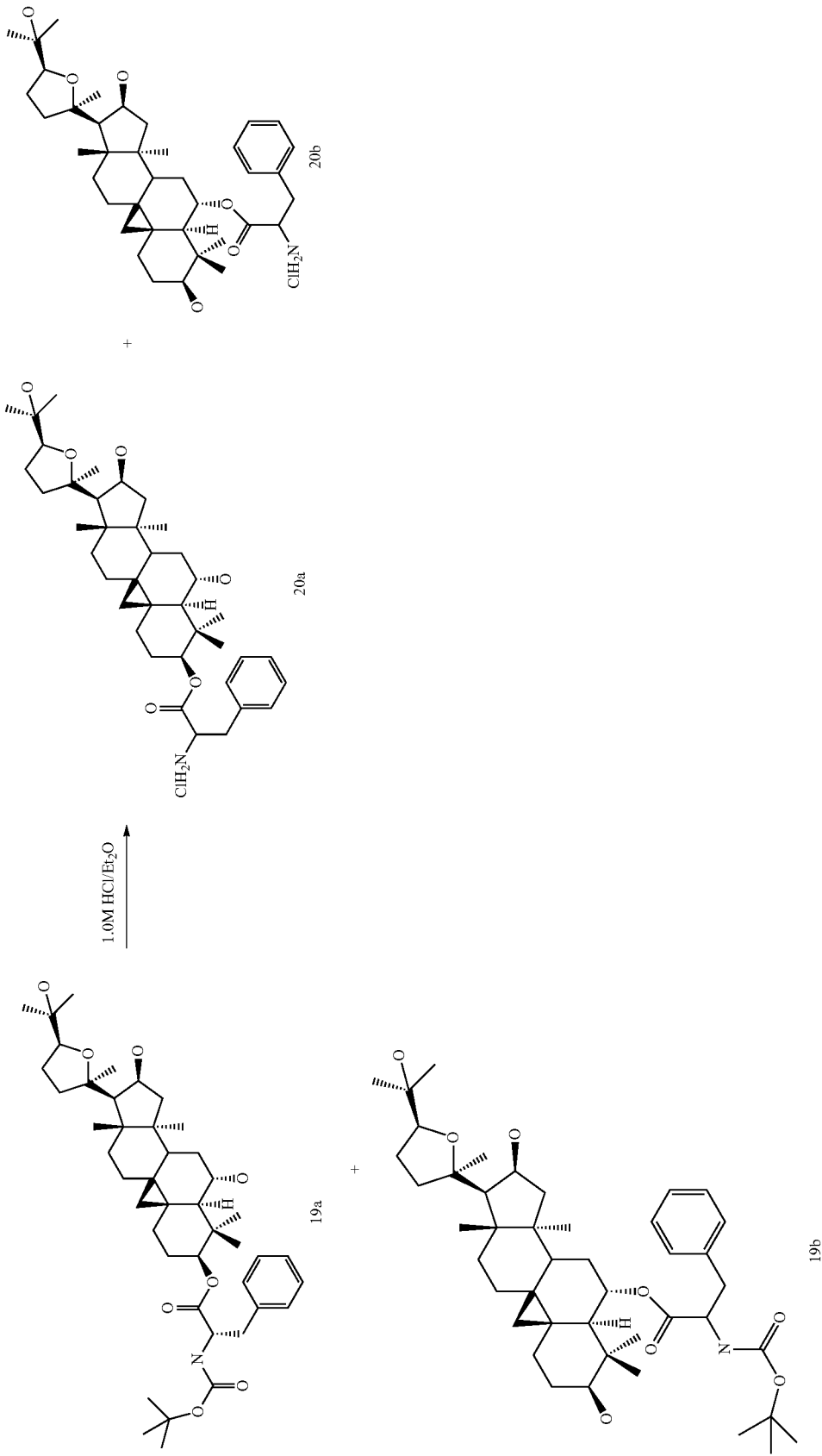

Preparation of 20a, 20b: To a 330 mg (0.45 mmol) of the mixture of 19a and 19b was added 10 ml of 1.0M HCl/diethylether and stirred for 8 hrs. The white solids were filtered and washed with 10 ml of cold Et$_2$O (3×). The solids were then dried under high vacuum for overnight to yield 260 mg (86%) of the target products 20a and 20b as a white powder.

$^1$HNMR of the mixture (20a and 20b): (DMSOd$_6$) δppm: 0.22 (1H, bs), 0.55 (1H, bs), 0.70-1.10 (m, 24H), 1.20-1.30 (m, 3H), 1.42-1.55 (m, 2H), 1.61-1.80(m, 2H), 1.87-1.89(m, 2H), 2.19-2.20 (d, 1H), 2.42-2.50 (m, 1H), 2.92-3.10 (m, 2H), 3.20-3.21 (m, 2H), 3.30-3.34 (m, 1H), 3.55-3.61 (m, 1H), 3.78-3.88 (m, 1H), 4.12-4.20 (m, 2H), 4.42-4.45 (m, 1H), 4.48-4.53 (m, 1H), 4.80-4.82 (m, 1H), 7.08-7.25 (m, 5H), 8.62-8.80(bs, 3H). MS (M+H) 638

Example 11

Preparation of 3-Methyl-2-(L)-methylmino-butyric acid 16β-dihydroxy-17-[5-(1-hydroxy-1-methyl-ethyl)-2-methyl-tetrahydro-furan-2-yl]-6α-methoxy-4,4,13,14-tetramethyl-tetradecahydro-cyclopropa[9,10]cyclopenta[a]phenanthren-3β-yl ester, hydrochloride salt [C3-(L)-valyl-C6-cycloastragenol] (22)

This analog was made starting from intermediate 3 by the following procedure

Preparation of 21: 280 mg (0.41 mmols) of 3 was dissolved in 1.5 mL of NMP and 33 mg (0.82 mmols) of NaH (60% dispersion in oil) was added to it. The reaction was stirred for 10 minutes followed by addition of 80 μL of dimethylsulfate and stirred at the ambient temperature for 16 hrs. The reaction mixture was diluted with 25 mL of DCM and washed with H2O (4×5 mL) and brine (1×5 mL), dried over Na2SO4 and filtered. The filterate was concentrated under reduced pressure. The crude was purified purified using flash chromatography with solvent gradient of 1%-3% MeOH in DCM to furnish 170 mg (58% of 21.

$^1$HNMR for 21: (CDCl$_3$) δppm: 0.38 (1H, bs), 0.52 (1H, bs), 0.90-1.38 (m, 30H), 1.39-1.45(s,m, 12H), 1.59-1.63 (m, 5H), 1.76-1.82(m, 2H), 1.96-2.01(m, 4H), 2.16-2.20 (m, 1H), 2.30-2.35 (d, 1H), 2.49-2.54 (q, 1H), 2.70-2.73 (s,s, 3H), 3.20-3.22 (s,s, 3H), 3.26-3.28 (t, 1H), 3.70-3.75 (t, 1H), 4.19-4.21 (m, 1H), 4.53-4.61 (m, 1H), 4.70-4.73 (q, 1H). MS (M+H) 718.

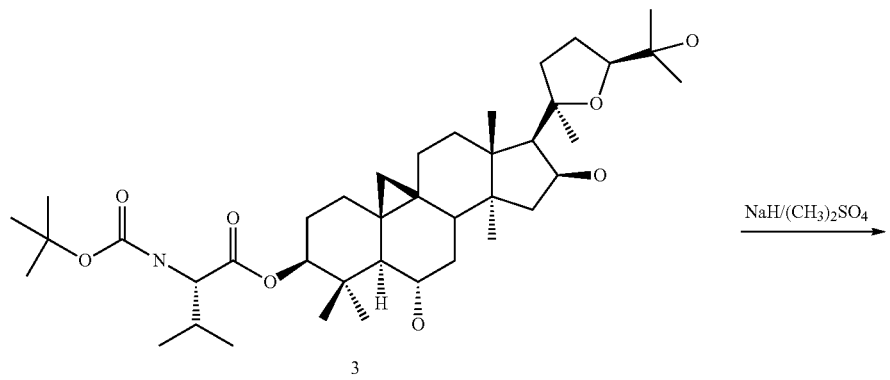

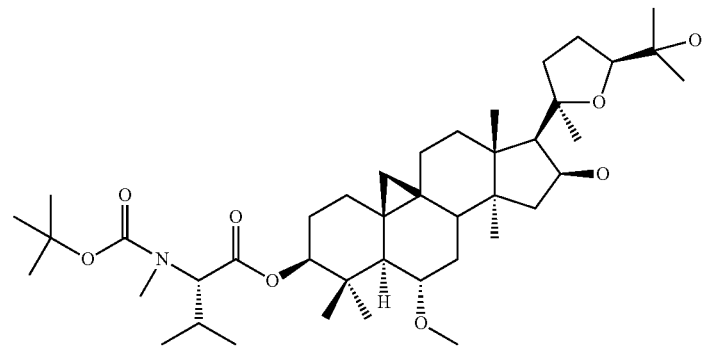

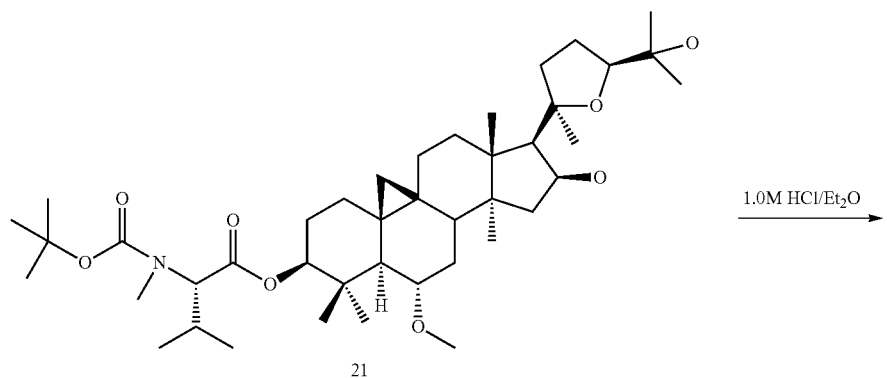

Preparation of 22: To 150 mg (0.21 mmol) of the 21 was added 8 ml of 1.0M HCl/diethylether and stirred for 24 hours. The white solids were filtered and washed with diethyl ether (2×5 ml). The solids were then dried under high vacuum for overnight to yield 115 mg (85%) of the target product 22 as a white powder.

¹HNMR for 22 (DMSOd₆) δppm: 0.35 (bs, 1H), 0.48 (bs, 1H), 0.81-1.40 (m, 29H), 1.45-1.60(m, 3H), 1.61-1.70 (m, 2H), 1.81-1.89(m, 4H), 2.19-2.30(m, 2H), 2.41-2.70 (m, 5H), 3.0-3.18 (m, 3H), 3.20-3.28 (m, 2H), 3.58-3.61(t, 1H), 3.81-3.83(m, 1H), 4.0-4.12 (bs, 4H), 4.49-4.51(m, 1H), 4.62-4.70 (m, 1H), 9.20-9.42 (bs, 2H). MS (M+H) 618.

Example 12

Preparation of 2-(L)-Amino-3-methyl butyric acid 6α,16β-dimethoxy-17-[5-(1-methoxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester. Hydrochloride salt [C3-(L)-valyl-C6,C16-dimethoxy-cycloastragenol] 27

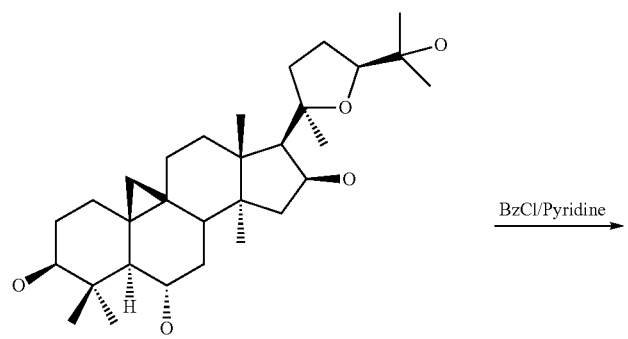

-continued
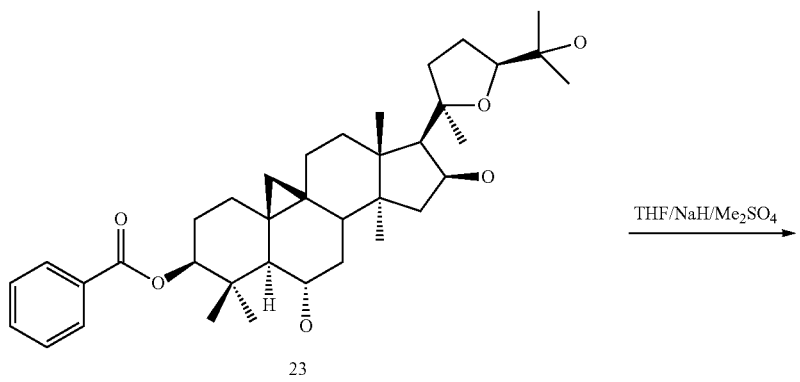
23
THF/NaH/Me₂SO₄ →
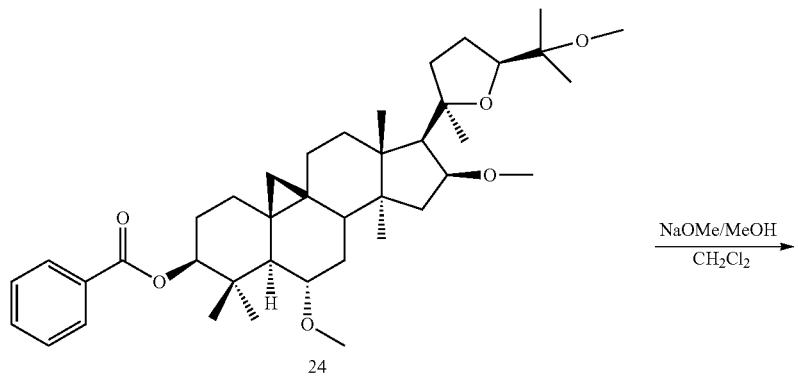
24
NaOMe/MeOH / CH₂Cl₂ →
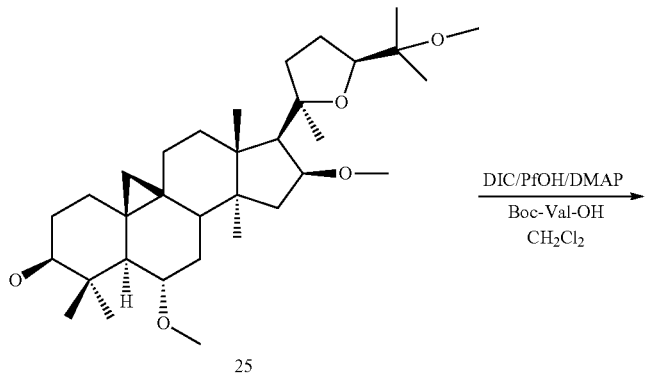
25
DIC/PfOH/DMAP
Boc-Val-OH
CH₂Cl₂ →
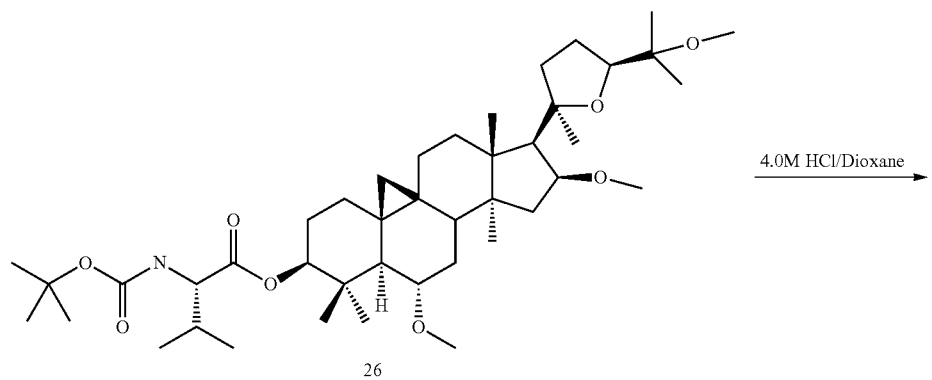
26
4.0M HCl/Dioxane →

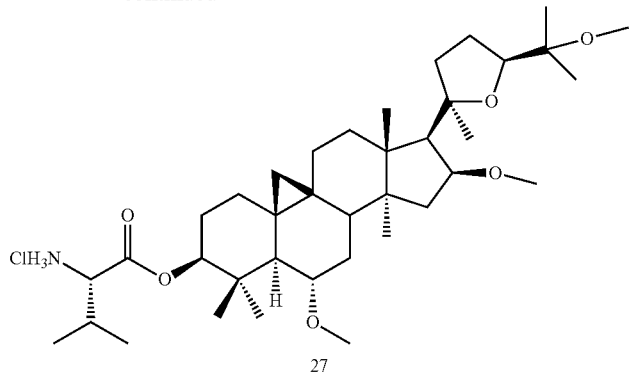

27

Preparation of 23: 5.0 g (10.2 mmols) of 2 was dissolved in pyridine (50 ml) and cooled to 0° C. Benzoyl chloride (2.35 ml, 20.4 mmols) was added and the reaction mixture was stirred at room temperature for 24 hrs. The reaction mixture was diluted with 200 ml of diethyl ether and washed with sat. NaHCO$_3$ (2×), H$_2$O (2×) and brine (1×). Dried over MgSO$_4$, filtered and the solvents evaporated under vacuum. The crude was purified by column chromatography using 1%-2% MeOH in DCM to furnish 1.6 g (26%) of 23 as white solids.

$^1$HNMR for 23: (CDCl$_3$) δppm: 0.38 (bs, 1H), 0.55 (bs, 1H), 0.90-2.0 (m, 37H), 1.70-1.82(m, 2H), 2.30-2.35 (m, 1H), 2.50-2.6 (m, 1H), 3.45-3.57 (m, 1H), 3.71-3.76(m, 1H), 4.69-4.71 (m, 1H), 4.79-4.81 (m, 1H), 7.41 (t, 2H), 7.52 (t, 1H), 8.03 (d, 2H). MS (M+H) 595.

Preparation of 24: 600 mg (1.01 mmols) of 23 was dissolved in THF (10 ml) and NaH (323 mg, 8.08 mmols) was added and the reaction mixture was stirred for 20 minutes. Dimethyl sulfate (509 mg, 4.04 mmols) was added and the reaction mixture was stirred at room temperature for 16 hrs. The reaction mixture was diluted with 100 ml of diethyl ether and quenched with H$_2$O and successively washed with H$_2$O (2×) and brine (1×), dried over MgSO$_4$, filtered and the solvents evaporated under vacuum. The crude was purified by column chromatography using 1%-2% MeOH in DCM to furnish 460 mg of (72%) of 24 as white solids.

$^1$HNMR for 24. (CDCl$_3$) δppm: 0.30 (bs, 1H), 0.53 (bs, 1H), 0.90-2.0 (m, 37H), 2.40-2.45 (m, 2H), 2.92-2.96 (m, 1H), 3.10-3.14 (s, 3H), 3.22-3.24(s, 3H), 3.80-3.82(m, 1H), 3.9-4.10(m, 1H), 4.69-4.70(m, 1H), 7.43 (t, 2H), 7.52 (t, 1H), 8.04 (d, 2H). MS (M+H) 637.

Preparation of 25: 460 mg (0.72 mmols) of 24 was dissolved in DCM (10 ml) and to this was added 10 ml of 0.5M solution of NaOMe in MeOH and the reaction mixture was stirred at 40° C. for 48 hrs. The reaction mixture was quenched with a solution of sat. NaHCO$_3$ and the solvents were then evaporated under reduced pressure. The crude was purified by column chromatography using 1%-2% MeOH in DCM to furnish 210 mg of (55%) of 25 as white solids.

$^1$HNMR for 25: (CDCl$_3$) δppm: 0.24 (bs, 1H), 0.49 (bs, 1H), 0.90-2.0 (m, 37H), 2.40-2.45 (m, 2H), 2.92-2.96 (m, 1H), 3.10-3.14 (m, 3H), 3.22-3.24(m, 3H), 3.26-3.28 (m, 1H), 3.80-3.82(m, 1H), 3.9-4.10 (m, 1H). MS (M+H) 533.

Preparation of 26: Boc-Val-OH (685 mg, 3.16 mmols) was dissolved in 3 ml of DCM. To this was added 581 mg (3.16 mmol) of pentafluorophenol. The reaction was cooled in an ice-bath followed by slow addition of 0.49 ml (3.16 mmols) of DIC. After complete addition the reaction mixture was stirred at room temperature for 10 minutes at which time the reaction mixture turned turbid (diisopropylcarbodimide-urea precipitation). To this mixture was added 210 mg (0.395 mmols) of 25 followed by 385 mg (3.16 mmol) of DMAP and the reaction was stirred at room temperature for 48 hours. The reaction mixture was transferred into a separatory funnel and washed with H$_2$O (2×) 1% aq. HCl (2×), 0.1N aq. NaOH (2×), sat. NaHCO$_3$ (3×), H$_2$O (1×) and brine (1×), the organic layer was separated, dried over Na$_2$SO$_4$, filtered and the solvent was evaporated under vacuum. To the residue was then added 10 ml of diethylether and the urea was precipitated out. The filtrate was evaporated and the residue was purified using flash chromatography with solvent gradient of 2%-5% MeOH in DCM to furnish 277 mg (96%) of the target product 26.

$^1$HNMR for 26: (CDCl$_3$) δppm: 0.23 (bs, 1H), 0.49 (bs, 1H), 0.90-2.0 (m, 52H), 2.20-2.25 (m, 1H), 2.32-2.45 (m, 1H), 2.92-3.0 (m, 1H), 3.08-3.10 (s, 3H), 3.19-3.20 (s, 3H), 3.22-3.25(s, 3H), 3.82-3.84 (m, 1H), 3.90-3.92 (m, 1H), 4.10-4.21(m, 1H), 4.50-4.58(m, 1H), 4.91-5.01 (m, 1H). MS (M+H) 732.

Preparation of 27 To 100 mg (0.14 mmol) of the 26 was added 8 ml of 1.0M HCl/diethylether and stirred for 8 hrs. The white solids were filtered and washed with diethyl ether (2×5 ml). The solids were then dried under high vacuum for overnight to yield 65 mg (70%) of the target product 27 as a white powder.

$^1$HNMR for 27 (DMSOd$_6$) δppm: 0.20 (bs, 1H), 0.38 (bs, 1H), 0.75-1.90 (m, 43H), 2.10-2.15 (m, 1H), 2.20-2.25 (m, 1H), 2.82-2.88 (m, 1H), 2.93-3.03 (m, 3H), 3.19-3.20 (s, 3H), 3.22-3.25 (s, 3H), 3.70-3.79 (m, 1H), 3.90-3.92 (m, 1H), 4.10-4.21 (m, 1H), 4.50-4.58 (m, 1H), 8.14-8.24 (bs, 3H). MS (M+H) 632.

Example 13

Preparation of 2-(L)-Amino-3-methyl butyric acid 16β-hydroxy-17-[5-(1-hydroxy-1-methyl-ethyl)-2-methyl-tetrahydro-furan-2-yl]-4,4,13,14-tetramethyl-3-oxo-tetradecahydro-cyclopropa[9,10]cyclopenta[a]phenanthren-6α-yl ester, hydrochloride salt [C6-(L)-valyl-cycloastragenol](30): Preparation of C3-(L)-valyl-cycloastragenone

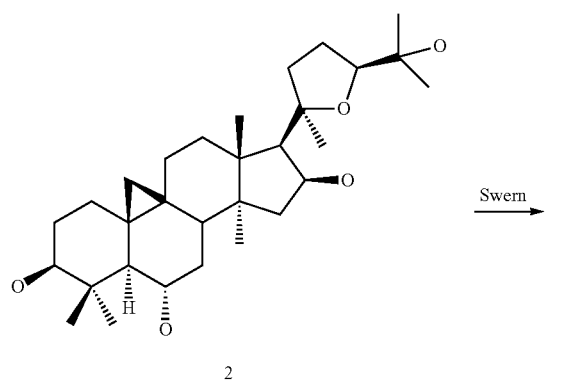

2

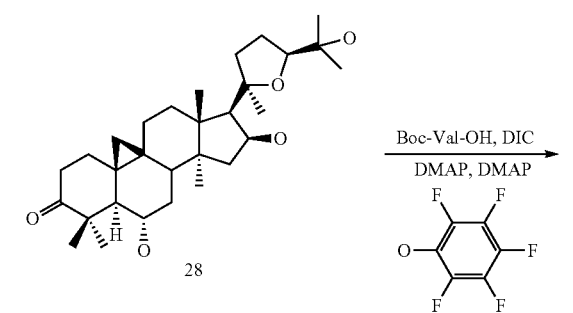

28

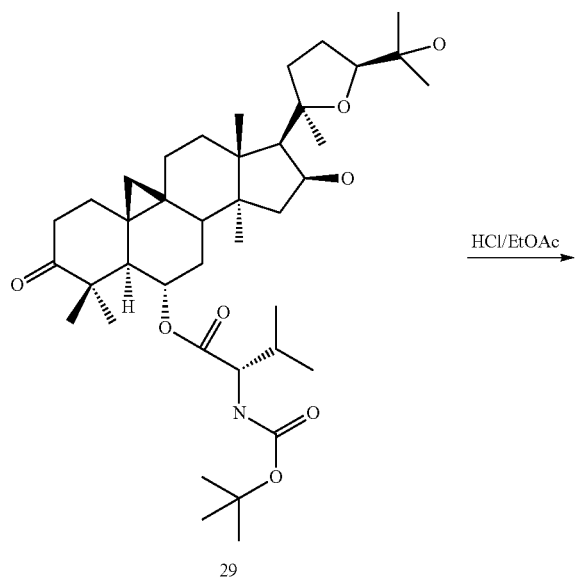

29

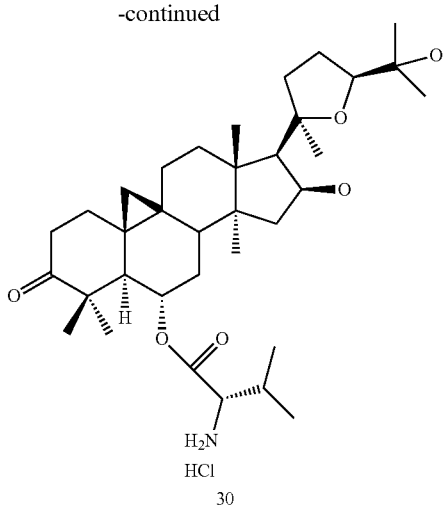

30

Preparation of 28: To a stirred solution of DMSO (6.4 g, 4 equ, 100 mL of DCM) at −60 to −70° C., oxalyl chloride (5.2 g in 10 mL of DCM) was added and it was stirred for 10 minutes. Compound 2 (10 g in 200 mL of DCM) was added over a period of 10 minutes and the reaction mixture was stirred for 30 minutes followed by addition of triethylamine (10.3 g over 5 min). The reaction was stirred at −60 to −70° C. for 1-2 hrs until the reaction was complete. The crude product 28 was purified by column chromatography. Eluted with Petroleum ether:ethyl acetate=4:1 to get 8 g of mono-oxidation product.

$^1$HNMR for 28: (CDCl$_3$) δppm: 0.38 (bs, 1H), 0.58 (bs, 1H), 0.80-1.32 (m, 25H), 1.50-2.20(m, 12H), 2.30-2.70 (m, 4H), 2.50-2.6 (m, 1H), 3.45-3.52 (m, 1H), 3.71-3.76(m, 1H), 4.69-4.72(m, 1H), MS (M+H) 489.

Preparation of 29: Boc-(L) Val-OH (0.54 g) was dissolved in 15 ml of DCM. To this solution 0.45 g of pentafluorophenol was added. The reaction was cooled in an ice-bath followed by slow addition of 0.4 ml of DIC. After complete addition the reaction mixture was stirred at room temperature for 30 minutes at which time the reaction mixture turned turbid (diisopropylcarbodiimide-urea precipitation). To this mixture was then added 0.3 g of compound 28 followed by 0.3 g of DMAP and the reaction was stirred at room temperature for 24 hours. The reaction mixture was transferred into a separatory funnel and washed with 0.1N aq. NaOH (2×), H$_2$O (3×) and brine (1×), the organic layer was separated, dried over Na$_2$SO$_4$, filtered and the solvent was evaporated under vacuum. The residue including compound 29 was not purified but taken to the next step of deprotection.

Preparation of 30: The above crude product was treated with HCl in ethyl acetate for 12 hrs. The product was then isolated by extraction with water and upon drying provided the crude HCl salt which was purified by prep-HPLC with petroleum ether and ethyl acetate mixture. The pure fractions were pooled to provide 120 mg of the final product 30.

$^1$HNMR for 30. (DMSOd$_6$) δppm: 0.40 (bs, 1H), 0.80 (bs, 1H), 0.80-1.32 (m, 29H), 1.50-2.20(m, 12H), 2.30-2.32 (m, 2H), 2.40-2.45 (m, 2H), 3.60-3.62 (m, 1H), 3.93-4.01 (m, 1H), 4.49-4.51(m, 1H), 4.79-4.81 (m, 1H). MS (M+H) 588.

Example 14

Preparation of 2-(L)-Amino-3-methyl-pentanoic acid 6α-(2-amino-3-methyl-pentanoyloxy-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-3β-yl ester hydrochloride salt [C3,C6-(L,L)-bis-isoleucine-cycloastragenol]-32

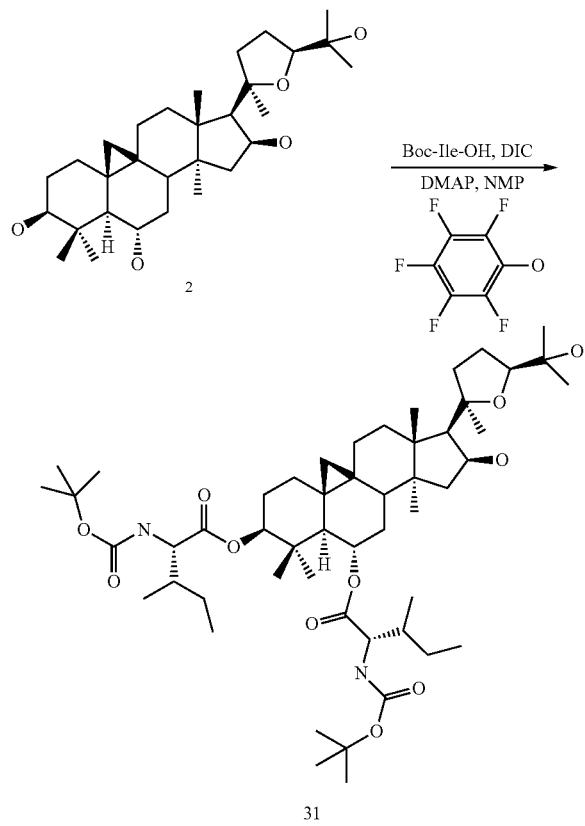

Preparation of 31: Boc-(L)-Ile-OH (4.6 g, 20 mmols) was dissolved in 25 ml of N-methylpyrrolidone (NMP). To this was added 3.7 g (20 mmol) of pentafluorophenol. The reaction was cooled in an ice-bath followed by slow addition of 3.1 ml (20 mmols) of DIC. After complete addition in the reaction mixture was stirred at room temperature for 30 minutes at which time the reaction mixture turned turbid (diisopropylcarbodiimide-urea precipitation). To this mixture was then added 1.0 g (2.04 mmols) of 2 followed by 1.7 g (14 mmol) of DMAP and the reaction was stirred at room temperature for 24 hours. The reaction mixture was transferred into a sepratory funnel and washed successively with $H_2O$ (6×), 1% aq. HCl (2×), 0.1N aq. NaOH (2×), sat. $NaHCO_3$ (3×), $H_2O$ (1×) and brine (1×), the organic layer was separated, dried over $Na_2SO_4$, filtered and the solvent was evaporated under vacuum. The residue was purified using flash chromatography with solvent gradient of 2%-5% MeOH in DCM to furnish 1.4 g (80%) of the target product 31.

$^1$HNMR for 31: ($CDCl_3$) δppm: 0.38 (1H, bs), 0.60 (1H, bs), 0.80-1.0 (m, 24H), 1.13 (s,s, 6H), 1.20 (s,s, 6H), 1.32(s, 6H), 1.35 (s,s, 4H), 1.41 (s,s, 18H), 1.55-1.60(m, 6H), 1.79-1.83 (m, 3H), 3.71-3.75 (t, 1H), 4.08-4.20 (m, 2H), 4.58-4.60 (m, 1H), 4.61-4.71 (q, 1H), 4.72-4.80 (m, 1H), 4.82-4.84 (d, 1H), 4.9-5.0 (d, 1H). MS (M+H) 915.

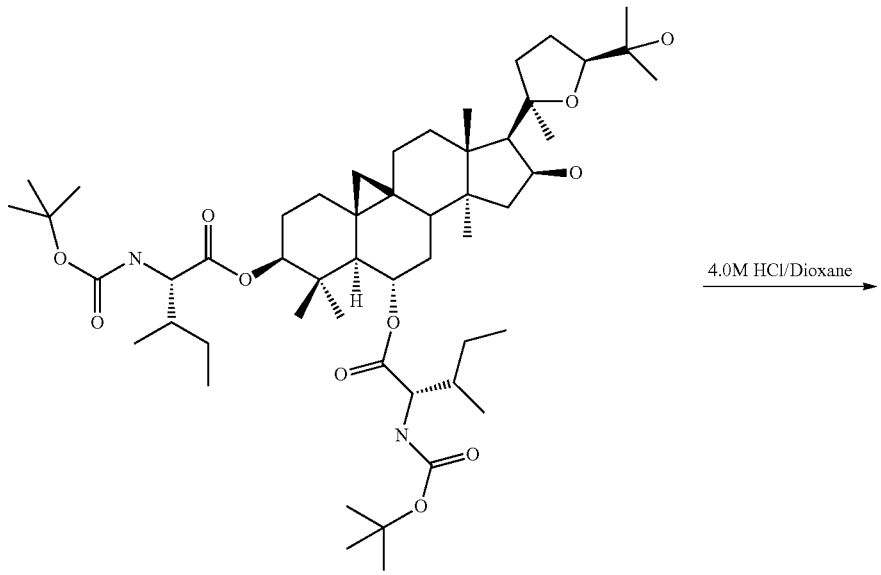

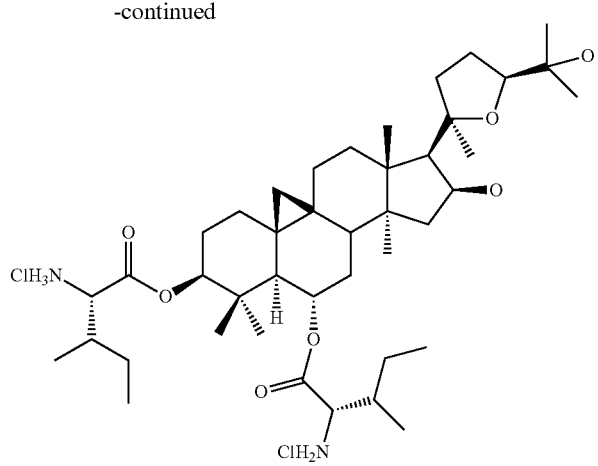
32

Preparation of 32: To a 1.5 g (1.6 mmol) of the 31 in 4 ml of dry Et$_2$O was added 3.5 ml of 4.0M HCl/dioxane and stirred for 4 hrs. The solvents were evaporated and the product was precipitated with three times of 40 ml of cold diethyl ether and the solids filtered off. The solids were then dried under high vacuum for overnight to yield 3.1 g (91%) of the target product 32 as a white powder.

$^1$HNMR for 32 (DMSOd$_6$) δppm: 0.22 (bs, 1H), 0.57 (bs, 1H), 0.80-1.20 (m, 35H), 1.41-1.80 (m, 14H), 2.10-2.21 (m, 2H), 2.34-2.42 (m, 4H), 2.20-2.30 (m, 2H), 3.59-3.62 (m, 1H), 3.81-3.83 (m, 2H), 4.42-4.53 (m, 1H), 4.61-4.71(m, 1H), 4.81-4.9 (m, 1H), 8.40-8.70(d, 4H). MS (M+H) 717.

Example 15

Preparation of 2-(L)-Amino-3-methyl-butyric acid 3β,6α-dihydroxy-16β-hydroxy-17-[5-(1-hydroxy-1-methyl-ethyl)-2-methyl-tetrahydro-furan-2-yl]-4,4,13,14-tetramethyl-tetradecahydro-cyclopropa[9,10]cyclopenta[a]phenanthren-16β-yl ester hydrochloride salt [C16-(L)-Valyl-cycloastragenol]-36

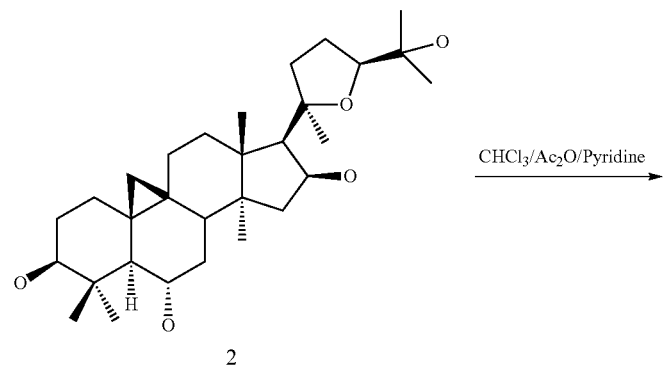
2

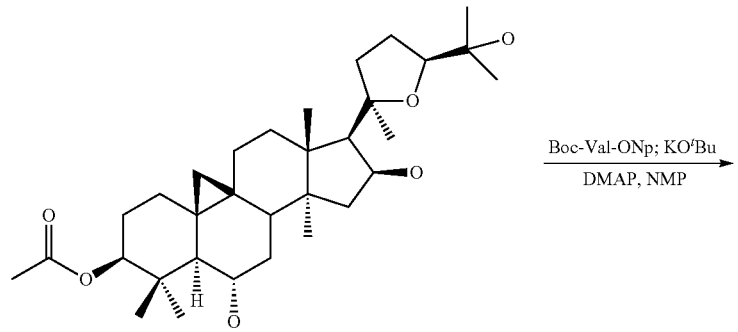
33

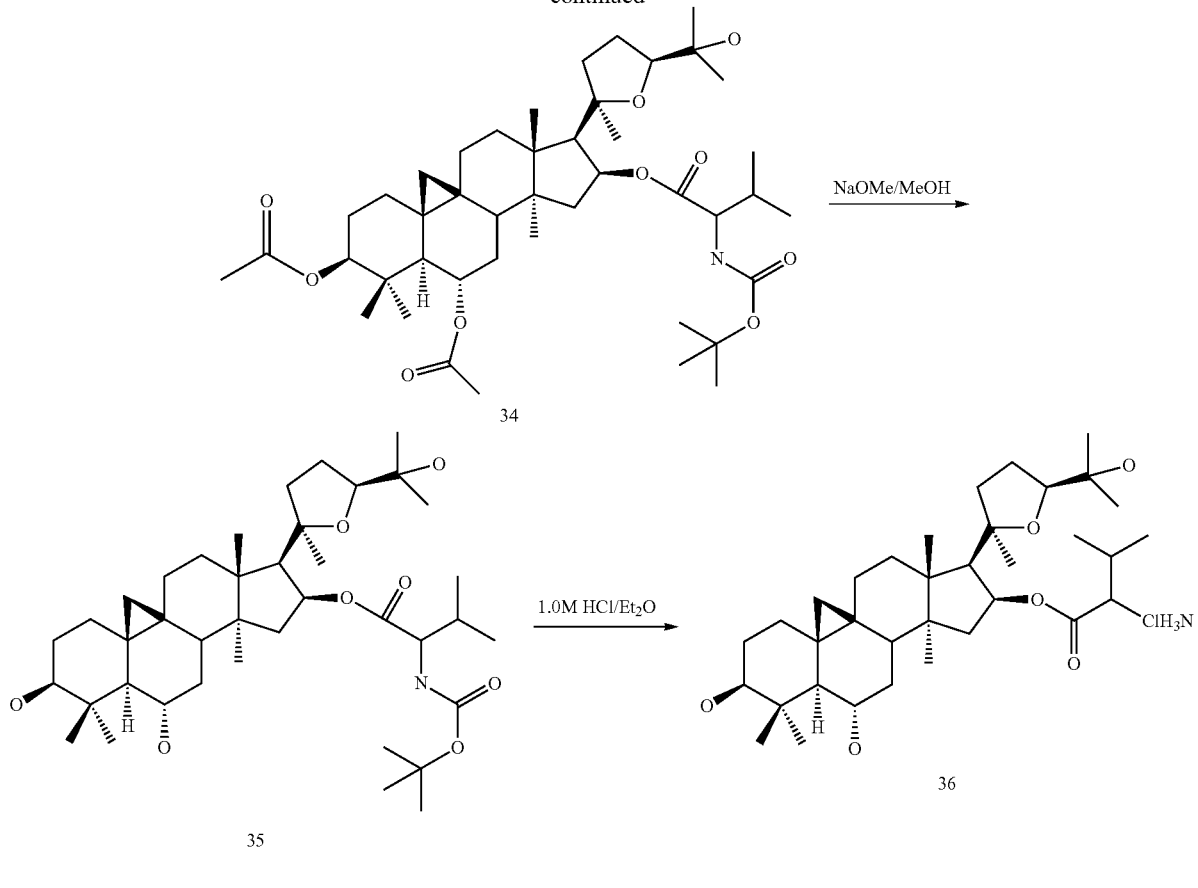

35

Preparation of 33: To 4 g (8.2 mmol) of 2 was added 100 ml of pyridine and cooled in an ice-bath. To this was slowly added 77 ml (820 mmol) of acetic anhydride followed by 100 mg (0.81 mol) of DMAP. The reaction mixture was stirred at for 16 hrs. The reaction mixture was cooled in an ice bath and quenched with 3% aq. HCl and diluted with 200 ml of DCM and washed successively with the following: sat. aq. NaHCO$_3$, (2×), H$_2$O (3×) and brine (1×). The organic layer was separated, dried over Na$_2$SO$_4$, filtered and evaporated under vacuum. The crude was purified by flash chromatography with 1% MeOH in DCM to furnish 4.2 g (89%) of 33 as white solids.

$^1$HNMR for 33: (CDCl$_3$) δppm: 0.38 (1H, bs), 0.49 (1H, bs), 0.90-1.25 (m, 32H), 1.39-1.45(m, 2H), 1.50-1.60 (m, 2H), 1.70-1.82(m, 2H), 1.96-2.01(m, 4H), 2.18-2.20 (s,s, 6H), 2.30-2.35 (d, 1H), 3.71-3.76(m, 1H), 4.49-4.59(m, 1H), 4.69-4.72(m, 2H). MS (M+H) 575.

Preparation of 34: 1.54 g (2.7 mmol) of 33 was dissolved in 8.0 ml of NMP. To the clear solution was added 800 mg (8.3 mmol) of potassium tert-butoxide and stirred for 45 mins. To this was added 3.0 g (8.9 mmols) of Boc-Val-ONp followed by 245 mg (2 mmol) of DMAP and stirred for 24 hrs. The reaction mixture was diluted with 100 ml of DCM and washed successively with the following: H$_2$O (4×), 1% aq. HCl (1×), (sat. aq. NaHCO$_3$, (2×), H$_2$O (3×) and brine (1×). The organic layer was separated, dried over Na$_2$SO$_4$, filtered and evaporated under vacuum. The crude was purified by flash chromatography with petroleum ether/ethyl acetate to furnish 1.0 g (48% of 34 as white solids.

$^1$HNMR for 34: (CDCl$_3$) δppm: 0.38 (1H, bs), 0.49 (1H, bs), 0.90-1.25 (m, 38H), 1.39-1.45(m,s, 11H), 1.50-1.60 (m, 2H), 1.70-1.82(m, 2H), 1.96-2.01(m, 4H), 2.18-2.20 (s,s, 6H), 2.30-2.35 (d, 1H), 3.71-3.76(m, 1H), 4.13-4.18 (m, 1H), 4.49-4.59(m, 1H), 4.62-4.72 (m, 1H), 5.12-5.17 (m, 1H), 5.38-5.42 (m, 1H). MS (M+Na$^+$) 796

Preparation of 35: To 700 mg (0.91 mmol) of 34 was added 20 ml of 0.5M solution of MeOH/MeONa and stirred for 16 hrs. The reaction was cooled in an ice bath and quenched with a solution of 1% aq. HCl to a pH of 5. The methanol was evaporated under reduced pressure and to the aq. layer was added a solution of saturated aq. NaHCO$_3$ and extracted with DCM (4×), the combined organic layer was dried over Na$_2$SO$_4$, filtered and evaporated under vacuum. The crude was purified by flash chromatography with a gradient of 2% to 3% MeOH/DCM to furnish 360 mg (58%) of 35 as white solids.

$^1$HNMR for 35: (CDCl$_3$) δppm: 0.38 (1H, bs), 0.49 (1H, bs), 0.90-1.25 (m, 38H), 1.39-1.45(m,s, 11H), 1.50-1.60 (m, 2H), 1.70-1.82(m, 2H), 2.10-2.20 (m, 2H), 2.30-2.35 (d, 1H), 3.20-3.25 (m, 1H), 3.41-3.50 (m, 1H), 3.71-3.76(m, 1H), 4.13-4.18 (m, 1H), 5.12-5.17 (m, 1H), 5.38-5.42 (m, 1H). MS (M+Na$^+$) 712

Preparation of 36: To 350 mg (0.51 mmol) of 35 was added 10 ml of 1.0 M solution of HCl/Et$_2$O and stirred for 5 hrs. The solvents were evaporated under reduced pressure and the residue was washed with dry 10 ml of Et2O (3×) and filtered under vacuum. The white solids were dried under high vacuum to furnish 25 mg (78%) of 36 as white solids.

$^1$HNMR for 36: (DMSOd$_6$) δppm: 0.38 (1H, bs), 0.49 (1H, bs), 0.80-1.25 (m, 29H), 1.39-1.83 (m, 4H), 2.10-2.20 (m, 2H), 2.30-2.40 (m, 4H), 3.18-3.21 (m, 1H), 3.38-3.40 (m, 1H), 3.71-3.76 (m, 1H), 4.13-4.17 (m, 1H), 5.40-5.42 (m, 1H), 8.38-8.53 (bs, 3H). MS (M+H) 590

Biological Example 1

Keratinocyte Cell/Telomerase Repeat Amplification Protocol (TRAP) Assay

The ability of a compound to increase telomerase activity in a cell can be determined using the TRAP (Telomeric Repeat Amplification Protocol) assay, which is known in the art (e.g. Kim et al., U.S. Pat. No. 5,629,154; Harley et al., U.S. Pat. No. 5,891,639). The activity is typically compared to the activity similarly measured in a control assay of such cells (e.g., a telomerase activity 50% greater than observed in a solvent control).

Cell lines suitable for use in the assay, normal human fibroblasts (NHF) or normal human keratinocytes (NHK), can be obtained from commercial sources, such as Cascade Biologics, Portland, Oreg. or 4C Biotech, Seneffe, Belgium, or from the ATCC (American Type Culture Collection). ATCC normal human fibroblast cell lines, which can be located on the ATCC web site, include, for example, CCL135, CCL137, and CCL 151.

Human epidermal keratinocyte (neonatal HEK) from three individual donors (Cascade Biologics, Portland, Oreg.) were pooled together and a Work Cell Bank generated. the cells were cultured in EpiLife Medium (Cascade Biologics, Cat.#M-EPI-500, Portland, Oreg.) supplemented with HKGS (Human Keratinocyte Growth Supplement) (Cascade, Cat.#S-001-5). HEKneo-P cells were seeded in 96-well plate 24 hr before treatment by trypsinizing the cells and neutralizing the digestion by neutralization buffer TN® (Cascade Biologics, Portland, Oreg.) to make a cell suspension. The cells were seeded at 5000 cells/100 uL/well in growth medium and the plate incubated at a 37° C., 5% $CO_2$/95% air, in a humidified tissue culture incubator. When the cells reach 75-80% confluence, seeding density should be around 2.5× $10^3/cm^2$.

Compounds to be tested were formulated in 10% DMSO with desired concentrations. 11 µL of the formulated compound in a concentration of 0.01 to 10 µM was added to the 96-well culture along with a control of 11 µL 10% DMSO. Non-treatment control (NT) was also included. Cells were harvested at 24 hr+/−1 hr by removing the growth medium and washing once with PBS (phosphate buffered saline) removing as much medium as possible. The cells were lysed by adding 50 µL of M-Per buffer (Pierce Cat# 78503 & 78501) and incubating on ice for 1 hr+/−15 min. The plate was, optionally, centrifuged at 2000 RPM, 5 min. The lysate was carefully collected from each well of the plate and transferred to a fresh V-bottom storage 96-well plate, leaving the monolayer cells intact.

A cytotoxicity assay was performed in parallel with the cell lysis by preparing a duplicate cell culture plate treated with the same compounds. After 24 hours+/−1 hour of incubation with compounds, 11 µL 1× Alamar Blue was added to the duplicate plate and the plate was incubated at 37° C. The plate was read at 1 and 3 hr with a fluorescence plate reader with excitation wavelength at 530 nm and emission wavelength at 590 nm. Cell viability (cytotoxicity) was directly proportional to the Alomar Blue reading.

| Tris-HCl pH | 8.3200 mM |
| MgCl2 | 15 mM |
| KCl | 650 mM |
| Tween 20 | 0.5% |
| EGTA | 10 mM |
| BSA | 1 mg/ml |

Primers:
Cy5-TS primer (AAT CCG TCG AGC AGA GTT) 5' end labeled (SEQ ID NO:1)
ACX primer (GCGCGCCTTACCCTTACCCTTAC-CCTAACC) (SEQ ID NO:2)
Taq polymerase was AmpliTaq DNA Polymerase, (Applied Biosystems, cat. # N8080171) and dNTP (Invitrogen, cat. # R72501).

TABLE 1

TRAP assay set up

| | Stock concentration | Per Reaction (µL) | Final con. |
|---|---|---|---|
| 10x TRAP buffer w/ BSA | | 5 | 1x |
| dNTP | 2.5 mM | 1 | 50 uM |
| Cy5-TS Primer | 0.5 mg/ml, 83 µM | 0.1 | 1 ng/µL |
| ACX | 0.1 mg/ml, 11 µM | 1 | 2 ng/µL |
| Taq polymerase | 5 U/ul | 0.4 | 0.04 U/µL |
| cell extract | | 5-10 | |
| $H_2O$ | | 32.5-37.5 | |
| Total | | 45 | |

The PCR mix includes the following components: Cy5-TS primer, a 5'-Cy5 labeled oligonucleotide have the sequence 5'-AAT CCG TCG AGC AGA GTT-3' (SEQ ID NO:1), is a telomerase substrate. Depending on the telomerase activity of the medium, telomer repeats (having the sequence . . . AGGGTT . . . ) will be added to the substrate, to form telomerase extended products, also referred to as telomerase products or TRAP products. The ACS primer, having the sequence 5'-GCG CGG CTT ACC CTT ACC CTT ACC CTA ACC-3' (SEQ ID NO:2), is an anchored return primer that hybridizes to the telomerase extended products.

A sample of cell lysate (5-10 µL) was added to the PCR mix in a reaction tube, and telomere extension/amplification is carried out by incubating the mixture at the following temperatures for the times indicated 30° C. 30 min; then 28 cycles of the 3-step PCR reaction; 94° C. for 30 seconds, 60° C. for 30 seconds, 72° C. for 1 minute, followed by 72° C. for 4 minutes, and hold at 4° C. The PCR reaction products are ready to subject to run polyacrylamide gel electrophoresis.

Loading dye containing e.g. bromophenol blue and xylene cyanol was added to the reaction mixture, and the samples are subjected to 10-15% non-denaturing Polyacrylamide gel electrophoresis (PAGE) in 1×TBE. The TRAP reaction products are observed, e.g. by using a fluoroimager for detection of CY5-labeled telomerase products (maximal excitation at 650 nm; maximal emission at 670 nm)

Telomerase activity was measured by captured total pixel vol. (DNA ladder bands) above background for each gel lane. The activity was normalized by measuring the total RNA (ng/mL) by using Ribogreen® RNA Quantitation Kit from Molecular Probes, cat. # R-11490 and following commercially recommended conditions with an RNA standard range of 0.8-2300 ng/mL, 1:2000 dilution of RG dye, 100-250× dilution of sample.

Total Pixel Vol/RNA=Normalized Relative Telomerase Activity

Cells viability (cytotoxicity) was directly proportional to the AB reading.

The results are shown in table 2.

TABLE 2

| Compound # | Name | Structure | Activity in in vitro HEK assay | $EC_{50}$ and fold increase of activity |
|---|---|---|---|---|
| 2 | cycloastragenol | 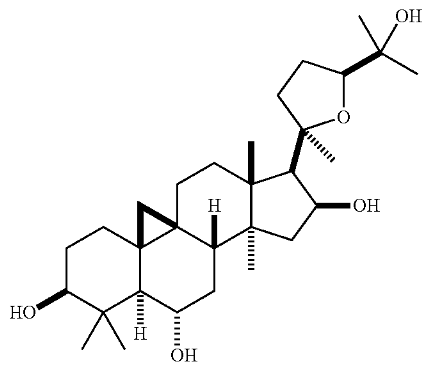 | + | $EC_{50}$ 30 nM Max: 3.3 fold |
| 4 | C3-(L)-Valyl-cycloastragenol MW = 624.5 | 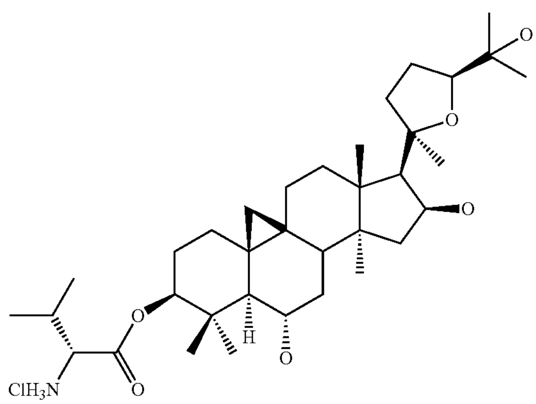 | + | $EC_{50}$ 6-22 nM Max 4.5 fold |
| 7 | C3,C6-(L,L)-bisvalyl-cycloastragenol MW = 761 | 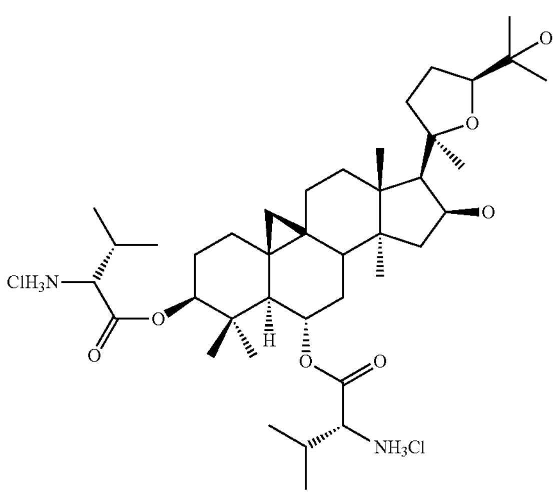 | + | $EC_{50}$ 41-50 nM; Max. 4.8 fold |

TABLE 2-continued

| Compound # | Name | Structure | Activity in in vitro HEK assay | EC$_{50}$ and fold increase of activity |
|---|---|---|---|---|
| 12 | C6-(L)-Valyl-cycloastragenol MW = 624.5 | 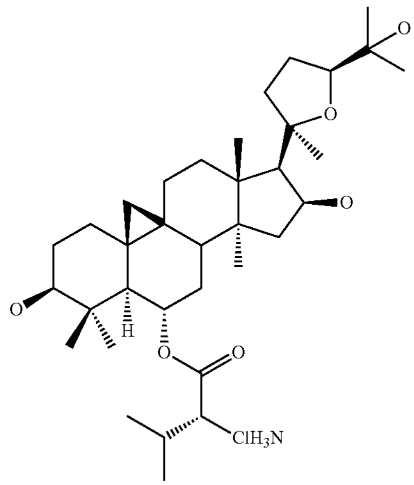 | + | EC$_{50}$ 28-32 nM: Max. 4.1 fold |
| 14 | C3-(L)-Isoleucyl-cycloastragenol MW = 639 | 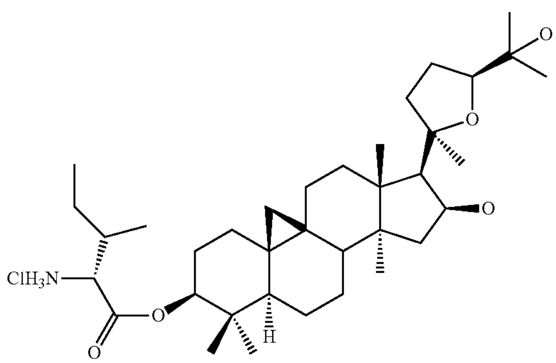 | + | EC$_{50}$ 9-21 nM; Max. 4.0 fold |
| 18a, 18b, 18c | C3-(L)-Glutamate-cycloastragenol, C6-(L)-Glutamate-cycloastragenol, L-Glutamate-C16-cycloastragenol MW = 654.5 | 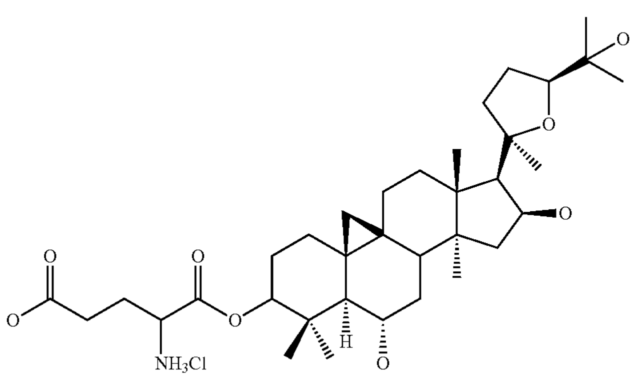 | | Active in PBMC |

TABLE 2-continued

| Compound # | Name | Structure | Activity in in vitro HEK assay | EC$_{50}$ and fold increase of activity |
|---|---|---|---|---|
| 16a, 16b, 16c | C3-(L)-Ornithinyl-cycloastragenol, C6-(L)-Ornithinyl-cycloastragenol, C16-(L)-Ornithinyl-cycloastragenol MW = 677 | 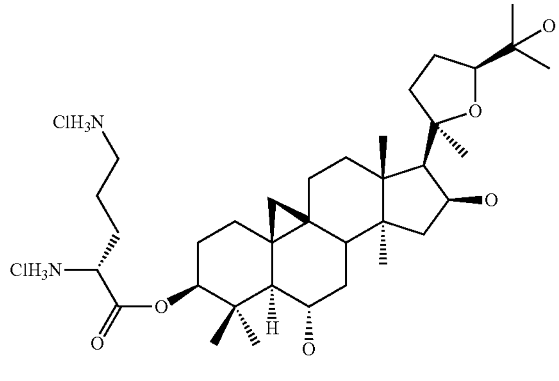 | – | |

TABLE 2-continued

| Compound # | Name | Structure | Activity in in vitro HEK assay | EC$_{50}$ and fold increase of activity |
|---|---|---|---|---|
| | | | | |
| | | | | |
| 20a, 20b | C3-(L)-phenylalanyl-cycloastragenol, C6-(L)-phenylalanyl-cycloastragenol MW = 637.5 | 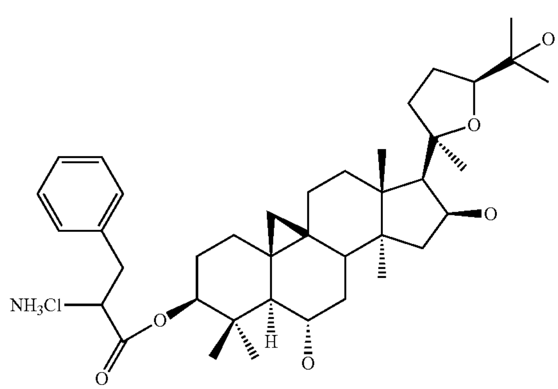 | Active in PBMC | |

TABLE 2-continued

| Compound # | Name | Structure | Activity in in vitro HEK assay | EC$_{50}$ and fold increase of activity |
|---|---|---|---|---|
| | | | | |
| 32 | C3,6 (L)-isoleucyl-cycloastragenol | 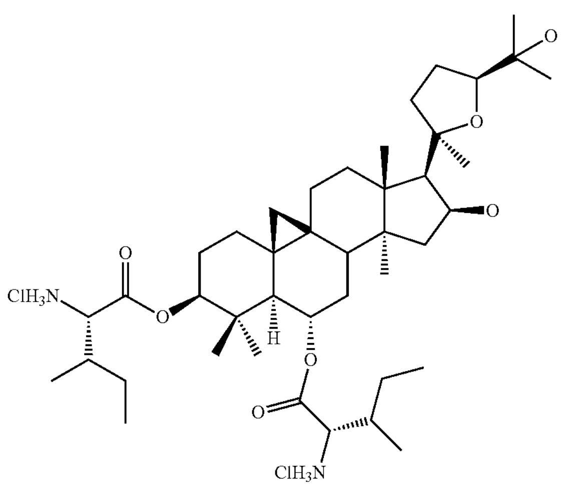 | + | Max 3 fold at 0.37-1.1 µM |
| 36 | C16-(L)-valyl-cycloastragenol MW = 624.5 | 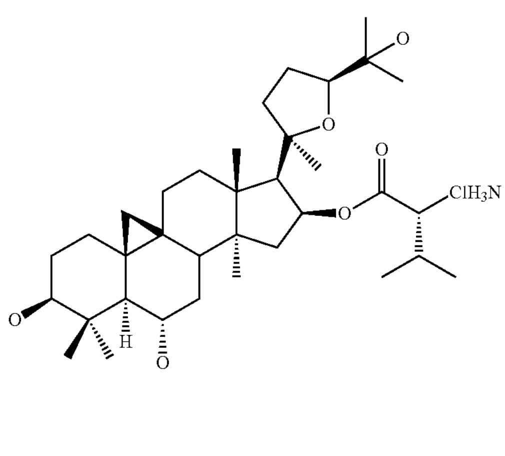 | + | Max. 3.0 fold at 0.01-0.12 µM |

TABLE 2-continued

| Compound # | Name | Structure | Activity in in vitro HEK assay | EC$_{50}$ and fold increase of activity |
|---|---|---|---|---|
| 30 | C6-(L)-valyl-C3-cyclo astragenone | 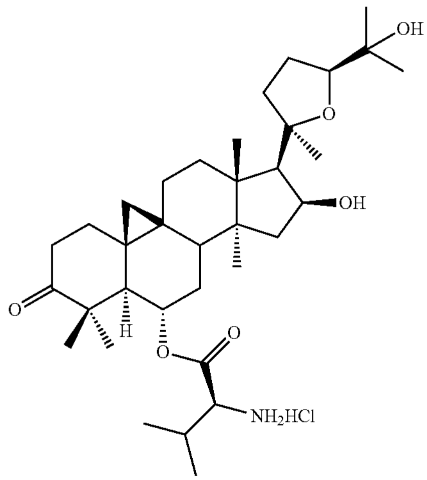 | + | EC$_{50}$ 31 μM Max 3.5 |
| 22 | C3-(L)-N-Methyl Valyl-C6 Methoxy-cycloastragenol MW = 652.5 | 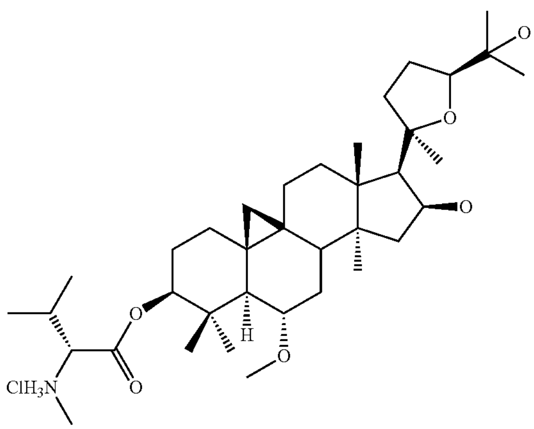 | − | |
| 8 | C3,C6-(D,D)-bisvalyl-cycloastragenol MW = 761 | 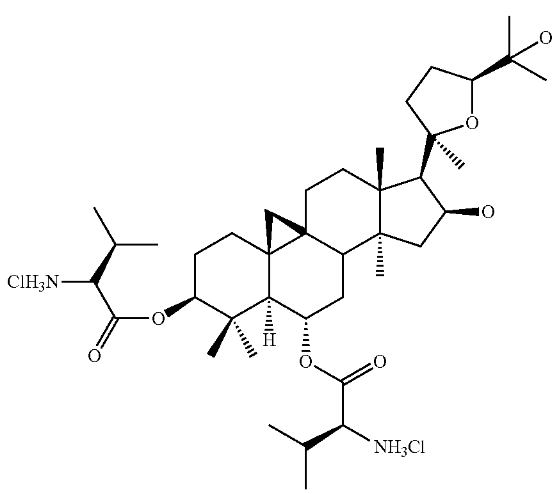 | − | |

TABLE 2-continued

| Compound # | Name | Structure | Activity in in vitro HEK assay | EC$_{50}$ and fold increase of activity |
|---|---|---|---|---|
| 5 | C3-(D)-valyl-cycloastragenol MW = 624.5 | 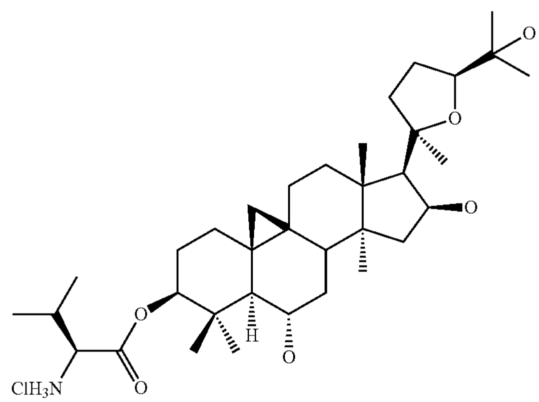 | — | |
| | C16-(L)-valyl-C3,6-diacyl-cycloastragenol MW = 710.5 | | — | |
| | C6-(L)-valyl-C3-acyl-cycloastragenol MW = 667.5 | | — | |

TABLE 2-continued

| Compound # | Name | Structure | Activity in in vitro HEK assay | EC$_{50}$ and fold increase of activity |
|---|---|---|---|---|
| 27 | C3-(L)-valyl-C6,16-dimethoxy-cycloastragenol MW = 652.5 | 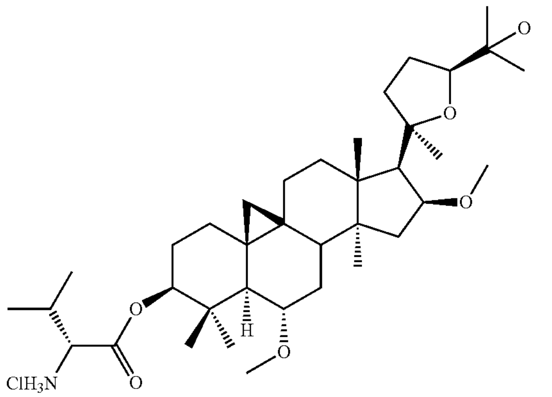 | — | |

+ telomerase activation is 2 fold or more in comparison with vehicle control at the peak of the full dose curve.

Biological Example 2

Peripheral Blood Monocyte Cell/Telomerase Repeat Amplification Protocol (TRAP) Assay PBMC Isolation. Blood was collected in sodium heparin vacutainers and pooled into a single 50 mL polypropylene tube. Blood was diluted 1:1 with 1×PBS and mixed thoroughly by inversion. 25 mL of diluted blood was layered over 12 mL of Lympholyte-H (Cedarlane Laboratories) and centrifuged at room temperature for 20 min at 800 g. Using a pipette, lymphocyte layer at interface of Lympholyte-H was carefully removed and transferred to a new 50 mL tube. The transferred cells were diluted 1:1 with 1×PBS and centrifuged at 800 g for 10 min to pellet the lymphocytes. The lymphocytes were washed 2 times with "complete" media, which consists of RPMI (Sigma, cat. No. R8758) that has been supplemented with 10% heat-inactivated FBS and 10 mM Hepes.

Culture Conditions. The cells were counted using Trypan Blue exclusion and resuspended in complete media that is supplemented with 50 Units of hIL-2/mL so that final concentration of cells is 1×10$^6$/mL. To cell suspension, CD2/3/28 Ab-coated beads from the T cell activation/expansion kit (Miltenyi, cat. No. 130-091-441) was added at a ratio of 1:2 (bead:cell). Cells were grown in a flask and half of the media is changed every 2-3 days (along with 20 Units of hIL-2/mL). At least once a week, cells are counted and media level is adjusted to keep cells around 5—10$^5$/mL.

Formulation of Analogs. Analogs were formulated in pure culture-grade DMSO at a concentration of 1 mM. From this stock, analogs are diluted to 100 µM in complete RPMI medium. A portion of the 100 uM formulation was diluted to 10 µM in complete RPMI medium containing 10% DMSO. Also, vehicle control was formulated by diluting DMSO in complete RPMI media to obtain a 10% solution (this is equivalent to the amount of DMSO in the analog dilutions).

Treatment with Analogs. After 10-14 days in culture, cells were counted and resuspended in conditioned media at a concentration of 1×10$^6$/mL. 0.5 mL of this cell suspension was plated into wells of a 24-well plate. Analog was diluted in fresh complete RPMI media 1:50 as to obtain concentrations of 2 µM (from 100 µM stock) and 0.2 µM (from 10 µM stock). Also, dilute the vehicle control (10% DMSO in RPMI medium) 1:50 in fresh complete RPMI media. Each well that contains 0.5 mL of cell suspension (should be 5×10$^5$ per well) receives 0.5 mL of diluted analog or DMSO vehicle control. Final concentrations of analogs were therefore 1 µM and 0.1 µM and final concentration of DMSO in all wells (including the vehicle control) is 0.1%.

Cell Harvesting and Preparation of cell Lysate. 24 hours after addition of analogs and DMSO vehicle control to culture, cells were removed from wells and added to microfuge tubes. Cells were centrifuged at 14,000 rpm for 2 minutes and media was aspirated, followed by resuspension in 0.5 mL of cold 1×PBS. Cells were centrifuged again for 2 minutes and PBS was aspirated. Cell pellet was resuspended in 100 µL of M-PER (mammalian protein extraction reagent) and incubated on ice for 30 minutes. After incubation, suspension was centrifuged at 14,000 rpm for 20 mm at 4° C. Following spin, 80 µL of lysate was transferred to a pre-chilled microfuge tube, being careful not to transfer any cellular debris. Final concentration of cell lysate was 5000 cells/µL.

TRAP Reaction and Gel. Samples were analyzed using a 1-step TRAP PCR reaction. Before conducting the reaction, samples were diluted 1:5 in M-PER buffer (1000 cells/µL). For each reaction the following mixture was used: 37.5 µL of H$_2$O, 5 µL of 10×TRAP buffer with BSA, 1 µL of 2.5 mM dNTP, 1 µL of 0.1 mg/mL ACX primer, 0.1 µL of 0.5 mg/mL Cy5-labeled TS primer, 0.4 µL of 5 U/µL Taq Polymerase, and 5 µL of diluted sample (50 µL total reaction). PCR reaction was as follows: 30° C. for 30 minutes, 28 cycles of 94° C. for 30 seconds, 60° C. for 30 seconds, 72° C. for 1 minutes, followed by 72° C. for 4 minutes. PCR products were separated on a 12.5% polyacrylamide gel and analyzed using a STORM phosphorimager.

| Compound | Name | Activity in PBMC | Fold increase at 1 μM |
|---|---|---|---|
| 2 | cycloastragenol | ++ | 1.6-20.7 |
| 4 | C3-(L)-Valyl-cycloastragenol MW = 624.5 | ++ | 1.4-19.4 |
| 16a, 16b, 16c mixture | C3-(L)-Ornithinyl-cycloastragenol, C6-(L)-Ornithinyl-cycloastragenol, C16-(L)-Ornithinyl-cycloastragenol MW = 677 | + | 1.2-8.1 |
| 18a, 18b, 18c mixture | C3-(L)-Glutamate-cycloastragenol, C6-(L)-Glutamate-cycloastragenol, L-Glutamate-C16-cycloastragenol MW = 654.5 | + | 0.9-6.8 |
| 20a, 20b mixture | C3-(L)-phenylalanyl-cycloastragenol, C6-(L)-phenylalanyl-cycloastragenol MW = 637.5 | −/+ | 2.0-4.1 |

Biological Example 3

Administration of Compounds to Mice and Analysis of Plasma Levels and Telomerase Activity in Tissues The plasma levels of a compound following a single intravenous, oral, intra-peritoneal, or sub-cutaneous administration in male C57BL/6 mice was determined. Plasma samples were collected and used to determine the plasma concentration of the compound and metabolites. In addition tissue samples, including whisker samples, and peripheral blood mononuclear cells (PBMC) cells were collected for telomerase activity analysis.

C57BL16 mice were divided into treatment groups. The mice were provided ad libitum SLAC-MO1 #W080208 (Shanghai Laboratories Animal Center, Shanghai, China) throughout the in-life portion of the study with the exception of the overnight fasting period prior to oral dosing. Water was available ad libitum.

Environmental controls for the animal room were set to maintain a temperature of 23±2° C., humidity of 50-70%, and a 12-hour light/12-hour dark cycle. The 12-hour dark cycle may be temporarily interrupted to accommodate study procedures. Animals were acclimated to study procedures for 1-7 days prior to initial dose administration.

Animals used in this study were selected based on body weights that fall within ±20% of the mean body weight, overall health and acclimation to caging. Animals were given free access to both food and water during the whole course of study with the exception of the overnight fasting period prior to oral dosing.

Doses were administered intravenously via tail vein, orally, sub-cutaneously, or intra-peritoneally as indicated in Table 3. Body weights were taken on the day of dose administration. Dose volume was determined based on individual body weight taken on day of dosing.

Blood samples (approximately 300 μL) were collected via cardiac puncture or via retro-orbital puncture after anesthesia into tubes containing K2-EDTA anticoagulant and 1 mg/ml NaF at the various time points after dosing. Blood was stored on ice and then plasma separated via centrifugation (8000 rpm×6 minutes). The plasma was stored at 20° C. until LC-MS/MS analysis.

Euthanasia was done by carbon dioxide inhalation followed by exsanguination. Whisker and peripheral blood mononuclear cells (PBMC) were collected in some animals at 30 hrs and were stored at −80° C. after processing.

PBMCs were harvested from blood using $K_2EDTA$ as the anticoagulant. After collection, the tube was gently inverted 8-10 times to mix. The tube was centrifuged at 12000 rpm for 30 sec. to pellet cells, the supernatant was removed and the resulting PBMC pellets were flash frozen in dry ice/methanol and were stored at −80° C. Cells were processed as indicated in Biological Example 2. FIG. 1 shows the telomerase activity in PBMCs over time after treatment with compound 4.

Figure 2:
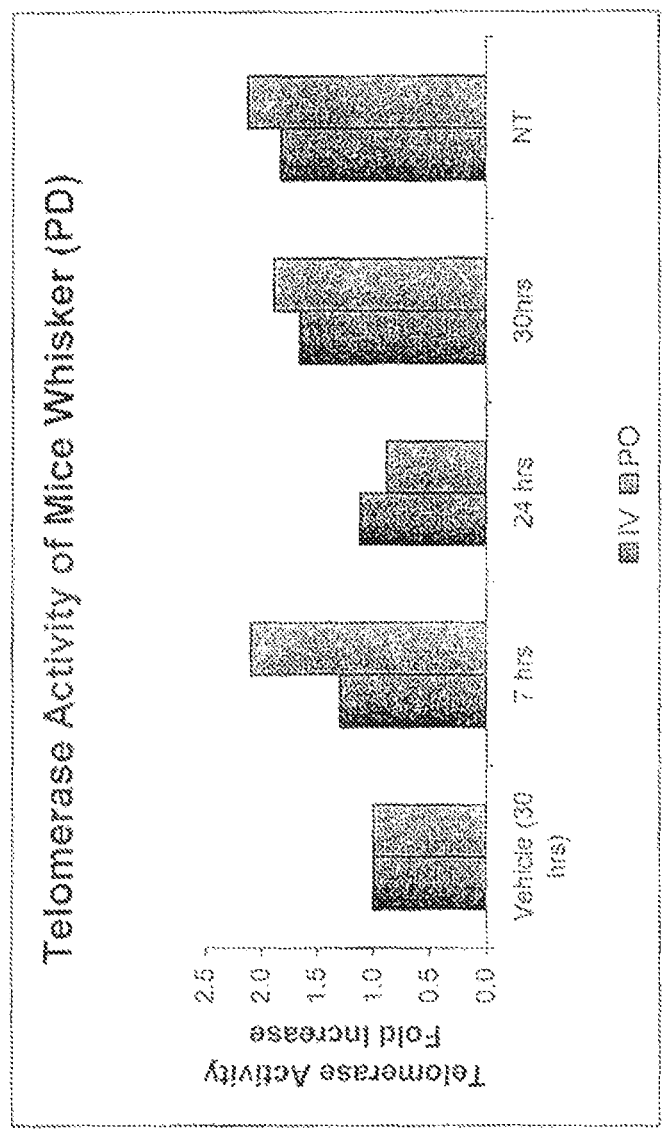
FIG. 2 shows an increase of telomerase activity in mice whiskers after one dose of compound 4 C3-(L)-valyl-cycloastragenol, as measured in a TRAP assay.

A single or group of whiskers were plucked and 10-20 whiskers/animal were placed in 200 μL of M-Per buffer (Pierce catalog #:78503/78501/78505, submerging the follicles). The samples were frozen in dry ice/methanol within 1 hour of plucking. FIG. 2 shows the telomerase activity in whiskers over time after treatment with compound 4.

It was determined that the mono-amino acid substituted compounds of Formula I when administered to mice show some conversion to cycloastragenol and the di-amino acid substituted compounds may show a minor amount of conversion to monosubstituted compounds.

The positional isomer mixtures, C3-(L)-Ornithinyl-cycloastragenol, C6-(L)-Ornithinyl-cycloastragenol, C16-(L)-Ornithinyl-cycloastragenol, (16a, 16b, 16c mixture) and C3-(L)-Glutamate-cycloastragenol, C6-(L)-Ornithinyl-cycloastragenol, L-Glutamate-G16-cycloastragenol (18a, 18b, 18c mixture) were not bioavailable in mice.

The bioavailability of the compounds is shown in Table 3.

TABLE 3

Study and bioavailability in Mice

| Test compound | Dose Level (mg/kg) | Vehicle | Dosing route | Bioavailability % F |
|---|---|---|---|---|
| 4 | 10 | 2% EtOH/98% water | PO | 48 |
| 4 | 10 | 2% EtOH/98% water | SC | 66 |
| 7 | 10 | 2% EtOH/98% water | PO | 25 |
| 7 | 10 | 2% EtOH/98% water | SC | 61 |
| 12 | 5 | 2% EtOH/98% water | PO | 8 |
| 12 | 5 | 2% EtOH/98% water | IP | 42 |
| 14 | 10 | 5% PEG400/5% solutol HS-15/90% water | PO | 42 |

Biological Example 4

Administration of Compounds to Male Rats and Analysis of Plasma Levels and Telomerase Activity in Tissues The plasma levels of a compound following a single intravenous and oral administration in carotid artery-cannulated male Sprague Dawley rats was determined. Plasma samples were collected and used to determine the plasma concentration of the compound and metabolites. In addition tissue samples, including whisker samples and PBMC cells were collected for telomerase activity analysis.

Carotid artery-cannulated male Sprague Dawley rats were divided into treatment groups according to Table 6. The rats were provided ad libitum SLAC-MO1 #YY080208 (Shanghai Laboratories Animal Center, Shanghai, China) throughout the in-life portion of the study with the exception of the overnight fasting period prior to oral dosing. Water was available ad libitum.

Environmental controls for the animal room were set to maintain a temperature of 23±2° C., humidity of 50-70%, and a 12-hour light/12-hour dark cycle. The 12-hour dark cycle may be temporarily interrupted to accommodate study procedures. Animals were acclimated to study procedures for 1-7 days prior to initial dose administration.

Animals used in this study were selected based on body weights that fall within ±20% of the mean body weight, overall health and acclimation to caging. Animals were given free access to both food and water during the whole course of study with the exception of the overnight fasting period prior to oral dosing.

The compounds were dissolved in 2% EtOH/98% water to yield a final concentration of 2.5 mg/ml and 1 mg/ml for both intravenous and oral administration, respectively. The concentration of each compound was confirmed by HPLC analysis.

Doses were administered intravenously via tail vein and orally as indicated in Table 4. Body weights were taken on the day of dose administration. Dose volume was determined based on individual body weight taken on day of dosing.

Blood samples (approximately 250 μL) were collected via cannulae into tubes containing K2-EDTA anticoagulant and 1 mg/ml NaF at the various time points. Blood was stored on ice and then plasma separated via centrifugation (8000 rpm×6 minutes). The plasma was stored at 20° C. until LC-MS/MS analysis.

Tissue samples: Whisker samples were collected in some animals at 30 hrs after dosing by hemostats and 10-20 whiskers/animal were placed in a 1.5 mL eppendorf tube that contains 200 μL of M-Per buffer (Pierce catalog # 78503/78501/78505). The samples were frozen in dry ice/methanol within 1 hour of plucking.

It was determined that the mono-amino acid substituted compounds of Formula I when administered to rats show some conversion to cycloastragenol and the di-amino acid substituted compounds may show a minor amount of conversion to monosubstituted compounds.

Percentage of bioavailability was calculated.

TABLE 4

Study and Bioavailability in Rats

| Test compound | Dose Level (mg/kg) | Vehicle | Dosing route | Bioavailability % F |
|---|---|---|---|---|
| 2 | 10 | 2% EtOH/98% water | PO | 22.6 |
| 4 | 10 | 2% EtOH/98% water | PO | 36 |
| 7 | 10 | 2% EtOH/98% water | PO | 44 |
| 12 | 10 | 2% EtOH/98% water | PO | 27 |
| 14 | 10 | 5% PEG400/5% solutol HS-15/90% water | PO | 93 |
| 20a, 20b | 10 | 2% EtOH/98% water | PO | 0.68 |

Biological Example 5

Administration of Compounds to Male Beagle Dogs and Analysis of Plasma Levels and Telomerase Activity in Tissues The plasma level of a compound following a single intravenous and oral administration in male Beagle dogs was determined. Plasma samples were collected and used to determine the plasma concentration of the compound and metabolites. In addition tissue samples, including whisker samples and PBMC cells were collected for telomerase activity analysis.

Male Beagle dogs were divided into treatment groups according to Table 5. The dogs were provided ad libitum SLAC-MO1 #W080701 (Shanghai Laboratories Animal Center, Shanghai, China) throughout the in-life portion of the study with the exception of the overnight fasting period prior to oral dosing. Water was available ad libitum.

Environmental controls for the animal room were set to maintain a temperature of 23±2° C., humidity of 50-70%, and a 12-hour light/12-hour dark cycle. The 12-hour dark cycle may be temporarily interrupted to accommodate study procedures. Animals were acclimated to study procedures for 1-7 days prior to initial dose administration.

Animals used in this study were selected based on body weights that fall within ±20% of the mean body weight, overall health and acclimation to caging. Animals were given free access to both food and water during the whole course of study with the exception of the overnight fasting period prior to oral dosing.

The compounds were dissolved in 2% EtOH/98% water of a solution of 5% PEG400, 5% solutol HS-15 (BASF, TX) 90% water to yield a final concentration of 2.5 mg/ml and 1 mg/ml for both intravenous and oral administration, respectively. The concentration of each compound was confirmed by HPLC analysis.

Doses were administered intravenously via the left femoral vein and then by oral dosing one week later. Body weights were taken on the day of dose administration. Dose volume was determined based on individual body weight taken on day of dosing.

Blood samples (approximately 250 μL) were collected via right femoral vein into tubes containing K2-EDTA anticoagulant and 1 mg/ml NaF at appropriate time points. Blood was stored on ice and then plasma separated via centrifugation (8000 rpm×6 minutes). The plasma was stored at 20° C. until LC-MS/MS analysis.

Percentage of bioavailability was calculated and is shown in Table 5.

TABLE 5

Study and Bioavailability in Dogs

| Test compound | Dose Level (mg/kg) | Vehicle | Dosing route | Bioavailability % F |
|---|---|---|---|---|
| 2 | 10 | 2% EtOH/98% water | PO | 3 |
| 4 | 10 | 2% EtOH/98% water | PO | 47 |
| 14 | 10 | 5% PEG400/5% solutol HS-15/90% water | PO | 55 |

Biological Example 6

Upregulation of Bone Marrow Hematopoietic Stem/Progenitor Cell Telomerase and Cell Proliferation Human bone marrow-derived CD34+ hematopoietic progenitor cells were obtained from a 47 year old healthy donor.
i) Telomerase Activation by Compound 4 in Short-Term Liquid Human Cell Culture Human bone marrow-derived CD34+ hematopoietic progenitor cells were grown in Iscove's Modified Dulbecco's Medium (IMDM) (Invitrogen, CA)+10% fetal bovine serum (FBS) for 3 days in the presence of compound 4 (1 uM, 100 nM, 10 nM), vehicle (1% DMSO), or nothing. Telomerase activity increased by ~60-70% in the 100 nM compound 4 sample relative to the vehicle control (as assessed by traditional gel-TRAP assay).

TABLE 6

Telomerase activity of huCD34+ cells: (Fold of Vehicle Control)

| | Telomerase activity increase |
|---|---|
| 1 uM compound 4 | 1.3-fold |
| 100 nM compound 4 | 1.8-fold |
| 10 nM compound 4 | 1.4-fold | ii) Increase in Number of Colony Forming Units in Compound 4-Treated Human Cell Cultures (14 Days of Treatment)

Human hematopoietic progenitor CD34+ cells (47 year old healthy donor) were plated into a standard colony formation assay in the presence of compound 4 (100 nM), vehicle (0.1% DMSO), or nothing. After 14 days, hematopoietic colonies were enumerated (CFU-E, BFU-3, CFU-GM, and CFU-GEMM). The plates containing compound 4 had 17% more colony forming units than vehicle alone. (Total colony counts were: untreated, 106.5; vehicle-treated, 103.5; compound 4-treated, 121.5)

TABLE 7

Colony formation of huCD34+ cells:

| | CFU-E | BFU-E | CFU-GM | CFU-GEMM | Total |
|---|---|---|---|---|---|
| 0.1% DMSO vehicle | 5.5 | 16 | 79.5 | 2.5 | 103.5 |
| 100 nM compound 4 | 11 | 25.5 | 80 | 5 | 121.5 |

Mouse bone marrow-derived lineage-depleted cells (enriched for hematopoietic stem and progenitor cells but not a pure population) were obtained.

i) Increase in Number of Colony Forming Units in Compound 4-Treated Mouse Bone Marrow Derived Cell Cultures from Normal Wild-Type Mice HSC (112 Days of Treatment)

Wild-type mouse lineage-depleted bone marrow cells from two separate mice were plated into a standard colony formation assay in the presence of compound 4 (100 nM and 500 nM), vehicle (0.1% DMSO), or nothing. After 12 days, hematopoietic colonies were enumerated (BFU-E, CFU-GM, and CFU-GEMM).

In Mouse 1, total colony counts were: untreated, 136; vehicle-treated, 122; 100 nM compound 4, 161; 500 nM compound 4, 162.

In Mouse 2, total colony counts were untreated, 107; vehicle-treated, 117; 100 nM compound 4, 121; 500 nM compound 4, 129.

TABLE 8

Colony formation of mouse cells:

| | | BFU-E | CFU-GM | CFU-GEMM | Total |
|---|---|---|---|---|---|
| Mouse 1 | 0.1% DMSO vehicle | 41 | 80 | 1 | 122 |
| Mouse 1 | 100 nM compound 4 | 50 | 111 | 0 | 161 |
| Mouse 1 | 500 nM compound 4 | 38 | 124 | 1 | 162 |
| Mouse 2 | 0.1% DMSO vehicle | 26 | 89 | 2 | 117 |
| Mouse 2 | 100 nM compound 4 | 31 | 90 | 1 | 121 |
| Mouse 2 | 500 nM compound 4 | 29 | 98 | 2 | 129 |

An increase in total colony counts was observed with administration of compound 4.

ii) Telomerase Activity by Compound 4 in Short-Term Liquid Culture in Mouse Bone Marrow-Derived Lineage-Depleted Cells from mTERT Heterozygous Mice and Wild-Type control (from the same parents)

Lineage-depleted bone marrow cells from mTERT heterozygous and wild type mice were grown in IMDM+15% FBS containing stem cell factor (Kitl), IL-3, and IL-11 for three days in the presence of compound 4 (1 uM, 100 nM, or 10 nM), vehicle (0.1% DMSO), or nothing. Telomerase activity in the wild-type cells increased by 40-50% when treated with 100 nM and 1 uM compound 4, relative to the vehicle-treated control.

Telomerase activity in the mTERT heterozygous cells increased by 50% when treated with 1 uM compound 4, relative to the vehicle-treated control.

iii) Increase in Number of Colony-Forming Units in Control 4-Treated Cultures of mTERT Heterozygous Mouse Cells (12 Days of Treatment).

mTERT heterozygous mouse lineage-depleted bone marrow cells were plated into a standard colony formation assay in the presence of compound 4 (100 nm and 500 nM), vehicle (0.1% DMSO), or nothing. After 12 days, hematopoietic colonies were enumerated (BFU-E, CFU-GM, and CFU-GEMM). Total colony counts were: untreated, 67; vehicle-treated, 64; 100 nM compound 4, 68; and 500 nM compound 4, 77.

TABLE 9

Compound 4 promotes colony-forming units in Lineage-depleted bone marrow cells from mTERT +/− mice

| | BFU-E | CFU-E | CFU-GEMM | Total |
|---|---|---|---|---|
| 0.1% DMSO | 26 | 37 | 1 | 64 |
| 100 nM compound 4 | 22 | 43 | 3 | 68 |
| 500 nM compound 4 | 27 | 48 | 1 | 77 |

Biological Example 7

Effect of Compound 4 Administration to BALB/c Mice on Telomerase Activity and Capillary Density in Matrigel Plugs and Telomerase Activity in Bone Marrow Stem/Progenitor Cells BALB/c mice (2-3 months) were dosed with compound 4 in 2% ethanol at 10 mg/kg/day PO (BID). Mice were pre-dosed for 1 day (Day −1). Matrigel™ (BDBiosciences, California) was injected subcutaneously in the abdomen on Day 0, and the Matrigel™ plugs were harvested on Day 12.

One half of the plug was analyzed for telomerase activity (RBC cell buffer extraction, followed by M-PER extraction) using the TRAP assay. A 1.9-fold increase ($p<0.2$) n=5/group in telomerase activity was observed in the Matrigel™ plug after treatment with compound 4.

Total RNA, which reflects cell number, was increased 1.6-fold ($p<0.2$) n=5/group in Matrigel™ plugs after treatment with compound 4.

The other half of the Matrigel™ plug was used for histology and CD31 immunostaining to analyze capillary density (CD31 is a marker for endothelial cells, which line the capillaries). A 1.3-fold increase in capillary density in (CD-31 immuno staining) ($p<0.5$) n=5/group was observed after treatment with compound 4.

ii) Bone Marrow Cells Harvested

Bone marrow stem and progenitor cells were purified from the treated mice using lineage depletion magnetic sorting technology (Miltenyi MACS columns). A 1.3 to 1.5-fold increase in telomerase activity as determined by the TRAP assay was observed in bone marrow stem and progenitor cells ($p<0.1$) n=3/group which had been treated with compound 4 as compared to the control.

Biological Example 8

Effect of Compound 4 Administration to C57BL/6 Aging TERT (+/−) Mice on Telomerase Activity and Capillary density in Matrigel™ Plugs and Telomerase Activity and Number of Bone Marrow Stem/Progenitor Cells Aging Tert (+/−) mice on a C57BL/6 background (8-9 months) were dosed with compound 4 at 10 mg/kg/day PO (BID) in 2% ethanol. Mice were pre-dosed for 1 day (Day −1). Matrigel™ was injected subcutaneously in the abdomen on Day 0, and plugs were harvested on Day 12.

One half of the plug was analyzed for telomerase activity and hemoglobin content, which is indicative of blood vessel formation (RBC cell buffer extraction, followed by M-PER extraction). The other half of the plug was processed for histology.

The Matrigel™ plug has a 1.8-fold increase ($p<0.02$) or a 2.6-fold increase ($p<0.01$), in telomerase activity as determined by 2 repeat TRAP experiments n=15/group for mice treated with compound 4.

The Matrigel™ plug has a 1.2-fold increase in hemoglobin levels ($p<0.2$) n=15/group for mice treated with compound 4.

Total RNA, which reflects cell number, was increased 1.5-fold ($p<0.1$) n−15/group in Matrigel™ plugs after treatment with compound 4.

Bone marrow stem and progenitor cells were purified using lineage depletion magnetic sorting technology (Miltenyi MACS columns). The bone marrow showed a 1.3-fold increase ($p<0.18$) or a 1.9-fold increase ($p<0.03$) in telomerase activity as determined by 2 repeat TRAP experiments n=6/group in the mice treated with compound 4.

The number of purified bone marrow stem/progenitor cells increased 1.5-fold ($p<0.1$) n=6/group in mice treated with compound 4.

Biological Example 9

Effect of Compound 4 and Compound 7 Administration on Human Brain Pericytes

Human brain pericytes (27 year old female donor) at PD 10 were cultured for a total of 30 hr in 0.5 µM compound 7 dissolved in water. Telomerase activity and tube formation were analyzed.

Brain pericytes were first cultured for 24 hr in a T-75 flask in 0.5 µM compound 7, and then split onto a 24 well plate coated with Matrigel in order to promote tube formation (done in triplicate). 0.5 µM compound 7 was again included in the medium. After 6 hr the samples were fixed and branch points were counted using a microscope, 5 fields/well, with 3 wells/condition. Compound 7 treated pericytes had 1.9 times more branch points than the control ($p<0.15$).

Cells were prepared and treated like above, but the 24 well plate was not coated with Matrigel. After 6 hr the cells were harvested for TRAP analysis (M-PER extract). A 2.8-fold increase in telomerase activity was observed in compound 7 treated pericytes.

Human brain pericytes (27 year old female donor) at PD 10 were plated and treated with 0.1 and 0.5 µM compound 4 in 0.1% DMSO 24 hr after seeding. Cells were incubated with drug for 30 hr and harvested for TRAP analysis (M-PER extract). A 1.8 and 1.9-fold increase in telomerase activity was observed with treatment of 0.1 and 0.5 µM, compound 4 respectively. Duplicate samples were tested.

Biological Example 10

Effect of Compounds 4 and 12 Administration on Human Small Airway Epithelial Cells Human small airway epithelia cells (SAECs) and airway derived fibroblasts (including the fetal lung fibroblast cell line IMR-90) were used for in vitro experiments to test the effect of compounds on telomerase activity.

SAECs and airway derived fibroblast cell line IMR-90 were seeded in 24 well plates. They were treated with 1 µM or 0.1 µM of compound 12 for 48 hours in a final concentration of 0.2% ethanol in the medium. The cells were washed with PBS and lysed with M-Per lysis buffer. Gel TRAP assay was performed to evaluated telomerase activity. It was found the compound 12 selectively up-regulated telomerase activity 2-4 fold in the epithelium derived cells (SAEC) but not in the fibroblast derived cell IMR-90. Replicate experiments confirmed these findings. In similar studies Compound 4 had similar properties and potency to compound 12.

SAECs were treated continuously with 0.1 µM of compound 4 in a final concentration of 0.004% ethanol for 60 days in continuous culture. Compound 4 increased the long-term replicative capacity of SAECs by about 2 population doublings (4× increase in calculated cell number). No effect was seen in lung fibroblasts in the long-term culture with compound 4.

Human SAECs or human fibroblasts were grown in the presence of different concentrations of compound 4 in a final concentration of 1% DMSO in the medium. After 3 days the cells were harvested and proliferation was measured using the Alamar Blue Proliferation Assay. The SAECs showed increased proliferation by about 50% in short term culture experiments. No effect was seen with compound 4 treatment in lung fibroblasts on short-term proliferation. The senescence markers p16 and p21 were significantly reduced in SAECs that were treated with compound 4 for only 3 days, and the reduction of these markers in fibroblasts was very small.

SAECs were seeded in a 24 well plate and treated with compound 12 at 1 μM and 0.1 μM in a final concentration of 0.2% ethanol in the medium. After 24 hours, media was changed and cells were again treated with compound 12. In addition a portion of the cells were treated with bleomycin (10 ug/ml) and TGFβ (10 ng/ml). Forty-eight hours after the second treatment, cells were washed and lysed with M-Per lysis buffer. A gel TRAP assay was run to evaluate the telomerase activity in the cells. In an in vitro model of fibrosis using TGFβ and bleomycin treated SAECs, myofibroblast/fibrosis biomarker alpha-smooth muscle actin (aSMA) increased and the epithelial biomarker E-cadherin (E-CAD) expression decreased. Both TGFβ and bleomycin suppressed SAEC telomerase activity and addition of compound 4 partially restored or protected telomerase activity against effects of these compounds in culture.

Although the invention has been described with respect to particular embodiments and applications, those skilled in the art will appreciate the range of applications and method of the invention disclosed herein.

It is claimed:

1. A method of increasing telomerase activity in a cell or tissue comprising contacting said cell or tissue with an isolated compound of formula I:

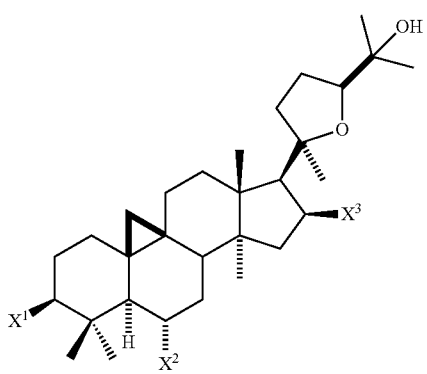

I wherein $X^1$, is selected from keto, hydroxy, and

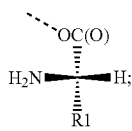

wherein $X^2$ is selected from keto, hydroxy, and

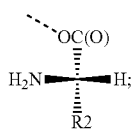

wherein $X^3$ is selected from keto, hydroxy, and

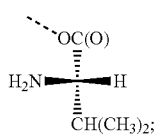

wherein at least one of $X^1$, $X^2$, and $X^3$ are

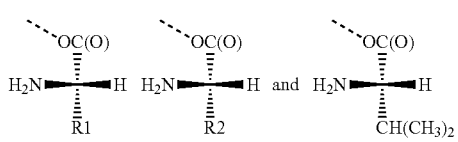

respectively;
wherein $R^1$ or $R^2$ are independently selected from —CH(CH$_3$)$_2$, and —CH(CH$_3$)CH$_2$CH$_3$ and pharmaceutically acceptable salts thereof, wherein the cell or tissue is identified as requiring increased telomerase activity to treat or prevent a condition or disease in a subject.

2. The method of claim 1, wherein $X^1$ is

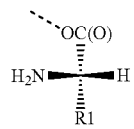

wherein $R^1$ is selected from the group consisting of —CH(CH$_3$)$_2$ or —CH(CH$_3$)CH$_2$CH$_3$.

3. The method of claim 1, wherein $X^2$ is

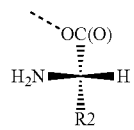

wherein $R^2$ is selected from the group consisting of —CH(CH$_3$)$_2$ or —CH(CH$_3$)CH$_2$CH$_3$.

4. The method of claim 1, wherein $X^3$ is

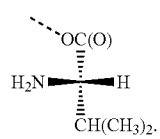

5. The method of claim 1, wherein at least one of $X^1$, $X^2$ or $X^3$ is

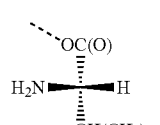

6. The method of claim 1, wherein both $X^1$ and $X^2$ are

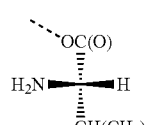

7. The method of claim 1, wherein at least one of $X^1$ or $X^2$ is —OC(O)CH(NH$_2$)CH(CH$_3$)CH$_2$CH$_3$.

8. The method of claim 1, wherein both $X^1$ and $X^2$ are —OC(O)CH(NH$_2$)CH(CH$_3$)CH$_2$CH$_3$.

9. The method of claim 1, wherein $X^1$ is a —OC(O)CH(NH$_2$)CH(CH$_3$)$_2$ and $X^2$ and $X^3$ are OH.

10. The method of claim 1, wherein $X^1$ is a —OC(O)CH(NH$_2$)CH(CH$_3$)CH$_2$CH$_3$ and $X^2$ and $X^3$ are OH.

11. The method of claim 1, wherein $X^2$ is a —OC(O)CH(NH$_2$)CH(CH$_3$)$_2$ and $X^1$ and $X^3$ are OH.

12. The method of claim 1, wherein $X^2$ is a —OC(O)CH(NH$_2$)CH(CH$_3$)CH$_2$CH$_3$ and $X^1$ and $X^3$ are OH.

13. The method of claim 1, wherein the disease or condition is selected from the group consisting of viral infections, opportunistic infections, HIV, degenerative diseases, neurodegenerative disease, degenerative diseases of the bones or joints and connective tissues, diabetic retinopathy, macular degeneration, cardiovascular diseases, central and peripheral vascular disease, Crohn's disease, immunological conditions, liver diseases, fibrosis, cirrhosis, lung diseases, pulmonary fibrosis, asthma, emphysema, COPD, hematopoietic disorders, anemia, thrombocytopenia, neutropenia, cytopenias, chronic inflammatory gastrointestinal diseases, Barretts esophagus, disorders related to loss of proliferative capacity in stem cell or progenitor cell populations, bone marrow failure syndrome, aplastic anemia, myelodysplastic anemia, myelodysplastic syndrome, wounds, acute or chronic conditions of the skin, burns, abrasions, incisions, grafts, lesions, chronic venous ulcers, diabetic ulcers, compression or decubitus ulcers, mucosal ulcers, keloid formation, hair loss, pigment loss, structural aberrations of the skin and its appendages, cancer, precancerous conditions in which low telomerase or shortened telomeres are associated with genomic instability, or increased mutation rates, or loss of tumor suppressor functions, and combinations thereof.

* * * * *